(12) United States Patent
Flanagan et al.

(10) Patent No.: US 11,786,687 B2
(45) Date of Patent: Oct. 17, 2023

(54) CANNULA FOR MINIMIZING DILUTION OF DOSING DURING NITRIC OXIDE DELIVERY

(71) Applicant: Mallinckrodt Hospital Products IP Limited, Mulhuddart (IE)

(72) Inventors: Craig Flanagan, Belmar, NJ (US); Simon Freed, Providence, RI (US); John Klaus, Cottage Grove, WI (US); Thomas Kohlmann, McFarland, WI (US); Martin D. Meglasson, Bloomsbury, NJ (US); Manesh Naidu, Randolph, NJ (US); Parag Shah, Morristown, NJ (US)

(73) Assignee: Mallinckrodt Hospital Products IP Limited, Dublin (IE)

( * ) Notice: Subject to any disclaimer, the term of this patent is extended or adjusted under 35 U.S.C. 154(b) by 584 days.

(21) Appl. No.: 16/785,978

(22) Filed: Feb. 10, 2020

(65) Prior Publication Data
US 2020/0171259 A1 Jun. 4, 2020

Related U.S. Application Data

(63) Continuation of application No. 15/412,348, filed on Jan. 23, 2017, now Pat. No. 10,556,082, which is a
(Continued)

(51) Int. Cl.
*A61M 16/06* (2006.01)
*A61M 16/10* (2006.01)
(Continued)

(52) U.S. Cl.
CPC ...... *A61M 16/0677* (2014.02); *A61M 16/009* (2013.01); *A61M 16/0666* (2013.01);
(Continued)

(58) Field of Classification Search
CPC .......... A61M 16/0677; A61M 16/0672; A61M 16/1005; A61M 16/122; A61M 16/0666;
(Continued)

(56) References Cited

U.S. PATENT DOCUMENTS 5,099,836 A * 3/1992 Rowland ........... A61M 16/0051
128/207.18
6,098,617 A * 8/2000 Connell ............ A61M 16/0486
128/207.14
(Continued)

FOREIGN PATENT DOCUMENTS

CN 101696752 A * 4/2010 ............. B29C 47/92

*Primary Examiner* — Samchuan C Yao
*Assistant Examiner* — Nathan M Le
(74) *Attorney, Agent, or Firm* — Servilla Whitney LLC

(57) ABSTRACT

The present invention generally relates to, amongst other things, systems, devices, materials, and methods that can improve the accuracy and/or precision of nitric oxide therapy by, for example, reducing the dilution of inhaled nitric oxide (NO). As described herein, NO dilution can occur because of various factors. To reduce the dilution of an intended NO dose, various exemplary nasal cannulas, pneumatic configurations, methods of manufacturing, and methods of use, etc. are disclosed.

18 Claims, 31 Drawing Sheets

Related U.S. Application Data continuation of application No. 14/312,003, filed on Jun. 23, 2014, now Pat. No. 9,550,039, which is a continuation of application No. 14/096,629, filed on Dec. 4, 2013, now Pat. No. 8,770,199.

(60) Provisional application No. 61/856,367, filed on Jul. 19, 2013, provisional application No. 61/784,238, filed on Mar. 14, 2013, provisional application No. 61/733,134, filed on Dec. 4, 2012.

(51) Int. Cl.
*A61M 16/20* (2006.01)
*A61M 16/12* (2006.01)
*A61M 16/08* (2006.01)
*A61M 16/00* (2006.01)

(52) U.S. Cl.
CPC .... *A61M 16/0672* (2014.02); *A61M 16/0875* (2013.01); *A61M 16/10* (2013.01); *A61M 16/104* (2013.01); *A61M 16/1005* (2014.02); *A61M 16/122* (2014.02); *A61M 16/125* (2014.02); *A61M 16/204* (2014.02); *A61M 16/208* (2013.01); *A61M 16/101* (2014.02); *A61M 2016/0021* (2013.01); *A61M 2016/0027* (2013.01); *A61M 2202/0208* (2013.01); *A61M 2202/0266* (2013.01); *A61M 2202/0275* (2013.01); *A61M 2202/0283* (2013.01); *A61M 2205/0216* (2013.01); *A61M 2205/3303* (2013.01); *A61M 2205/3331* (2013.01); *A61M 2205/75* (2013.01); *A61M 2210/0618* (2013.01)

(58) Field of Classification Search
CPC ...... A61M 16/0875; A61M 2202/0275; A61M 2202/0208; A61M 2205/3331; A61M 2210/0618; A61M 16/104
See application file for complete search history.

(56) References Cited

U.S. PATENT DOCUMENTS

| | | | | |
|---|---|---|---|---|
| 8,770,199 | B2* | 7/2014 | Flanagan | A61M 16/0677 |
| | | | | 128/207.18 |
| 9,550,039 | B2* | 1/2017 | Flanagan | A61M 16/122 |
| 9,795,756 | B2* | 10/2017 | Flanagan | A61M 16/0677 |
| 10,556,082 | B2* | 2/2020 | Flanagan | A61M 16/0666 |
| 2004/0163647 | A1* | 8/2004 | Figley | A61M 16/203 |
| | | | | 128/204.18 |
| 2009/0087606 | A1* | 4/2009 | Julien | B32B 27/304 |
| | | | | 428/36.6 |
| 2009/0194109 | A1* | 8/2009 | Doshi | A61M 16/0066 |
| | | | | 128/204.23 |
| 2011/0067704 | A1* | 3/2011 | Kooij | A61M 16/0816 |
| | | | | 128/207.18 |
| 2012/0125332 | A1* | 5/2012 | Niland | A61M 16/00 |
| | | | | 128/207.18 |

* cited by examiner

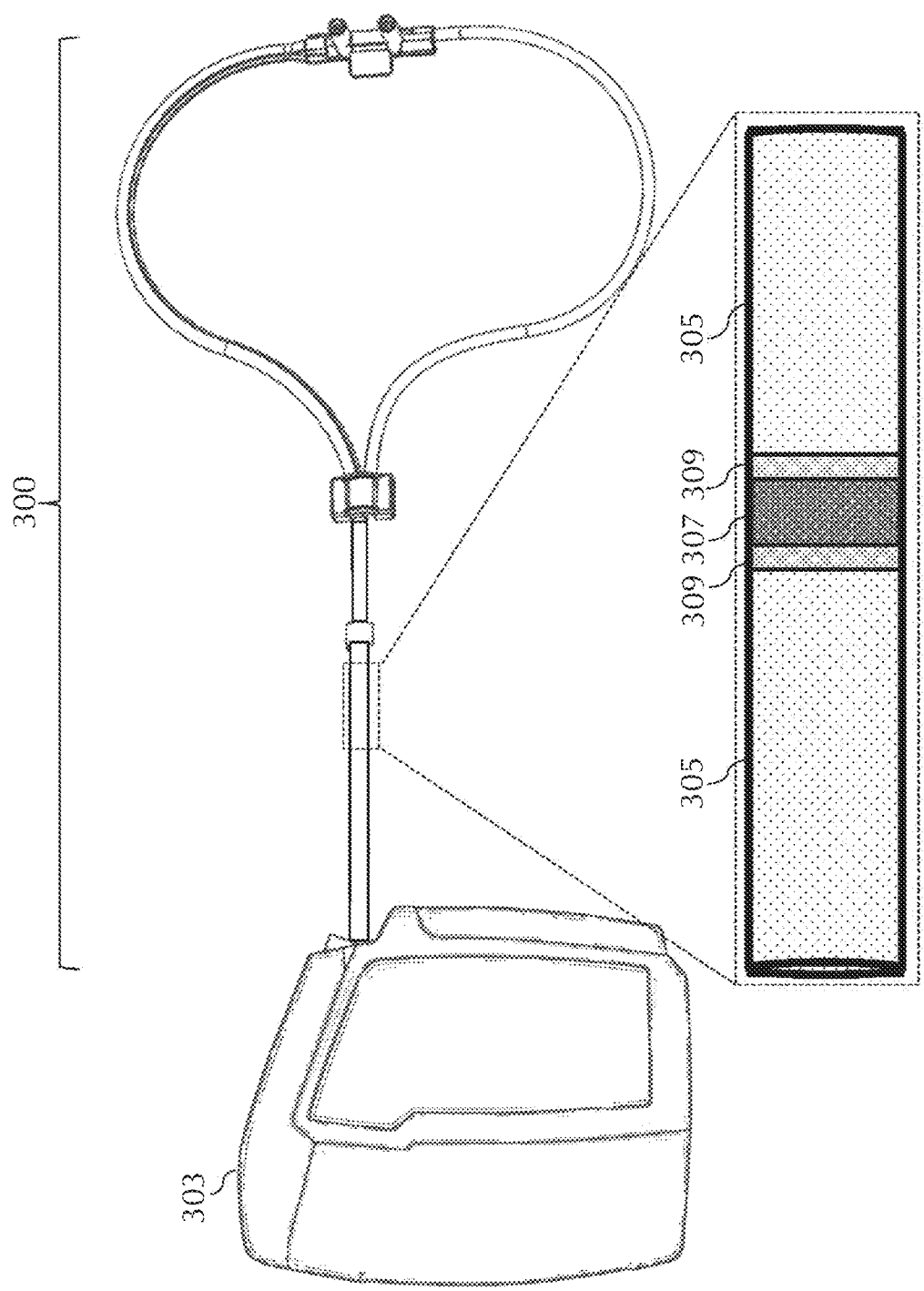

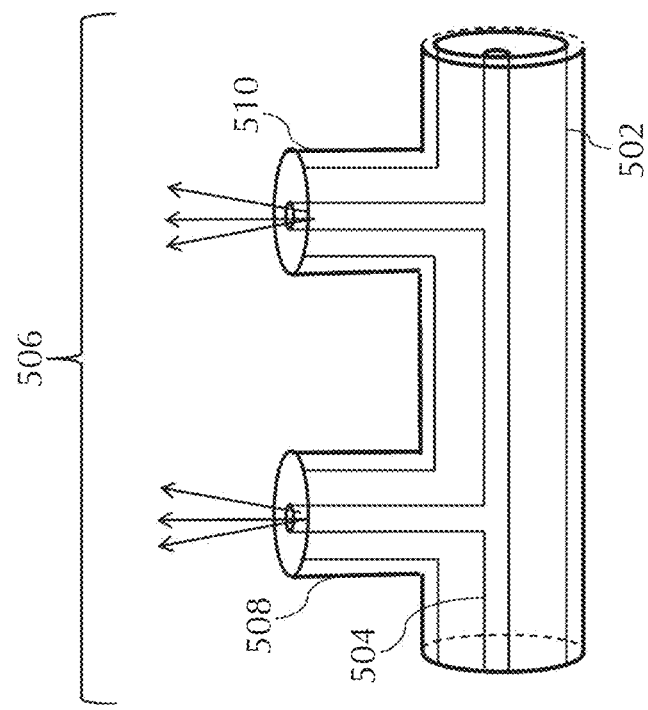
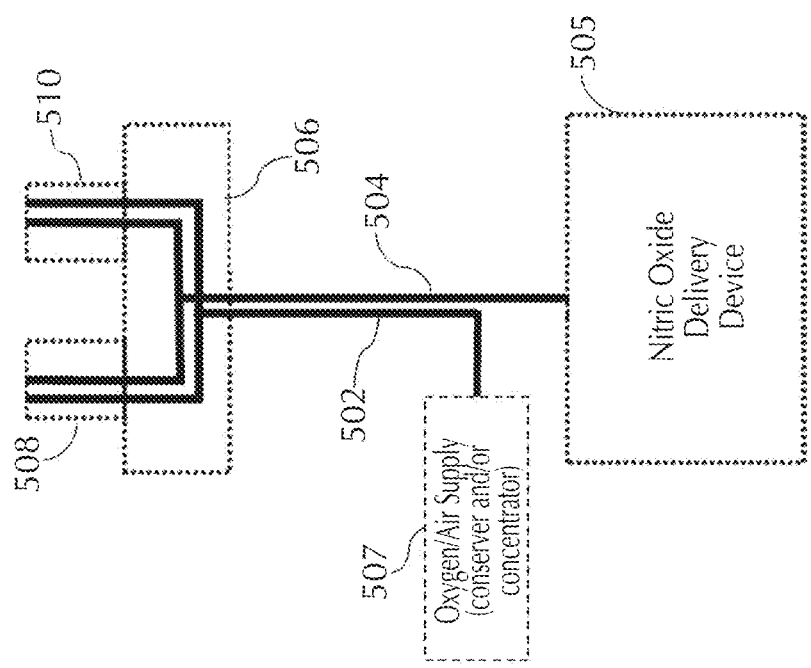
FIG. 5B
FIG. 5A

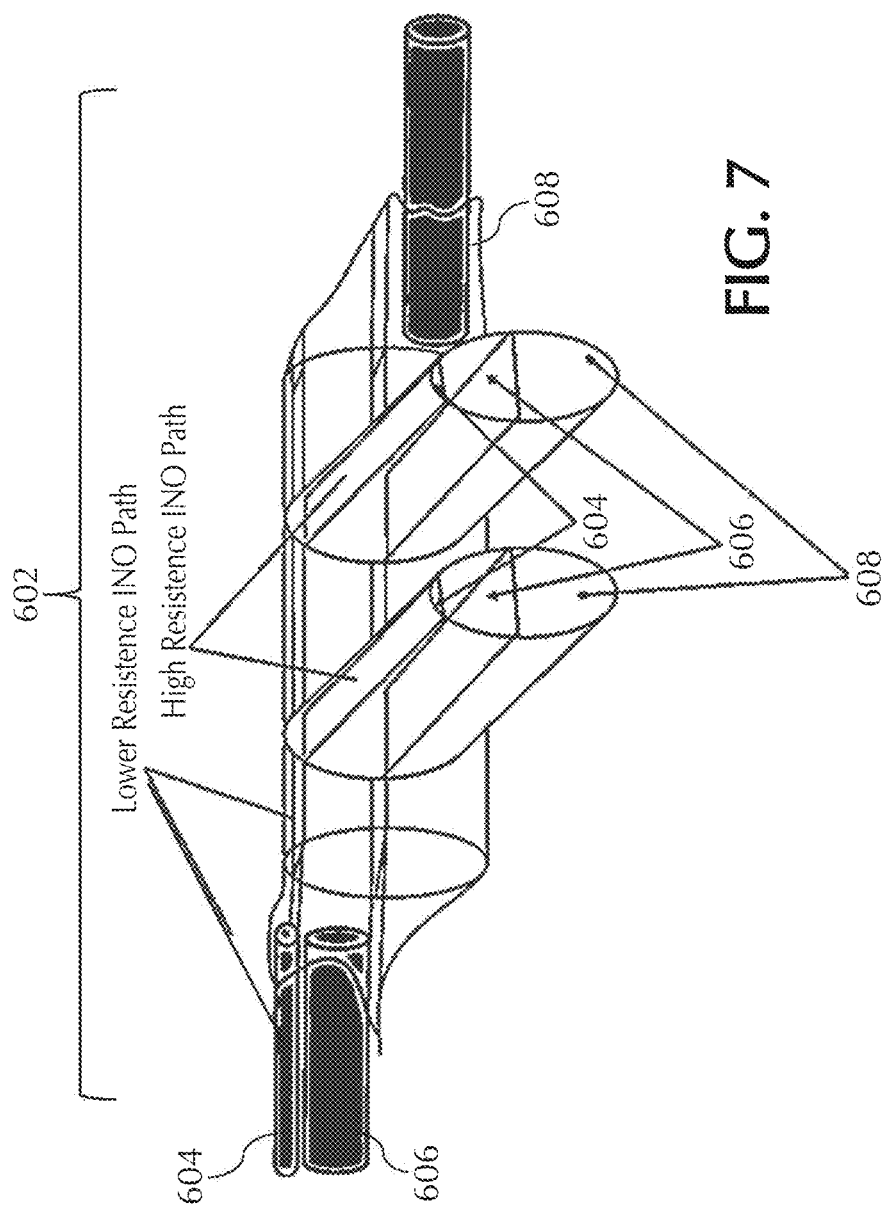

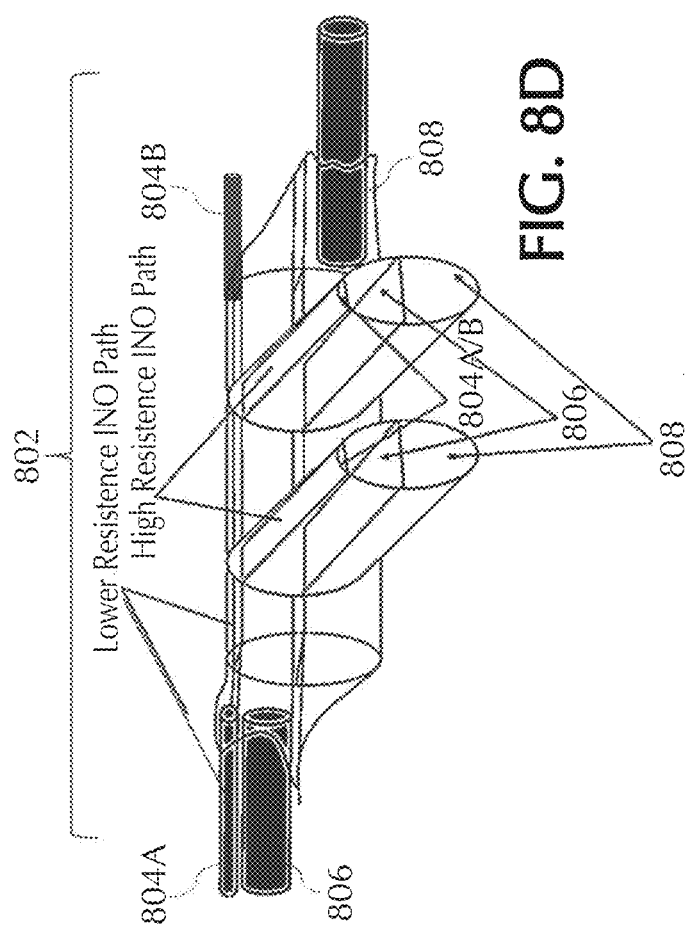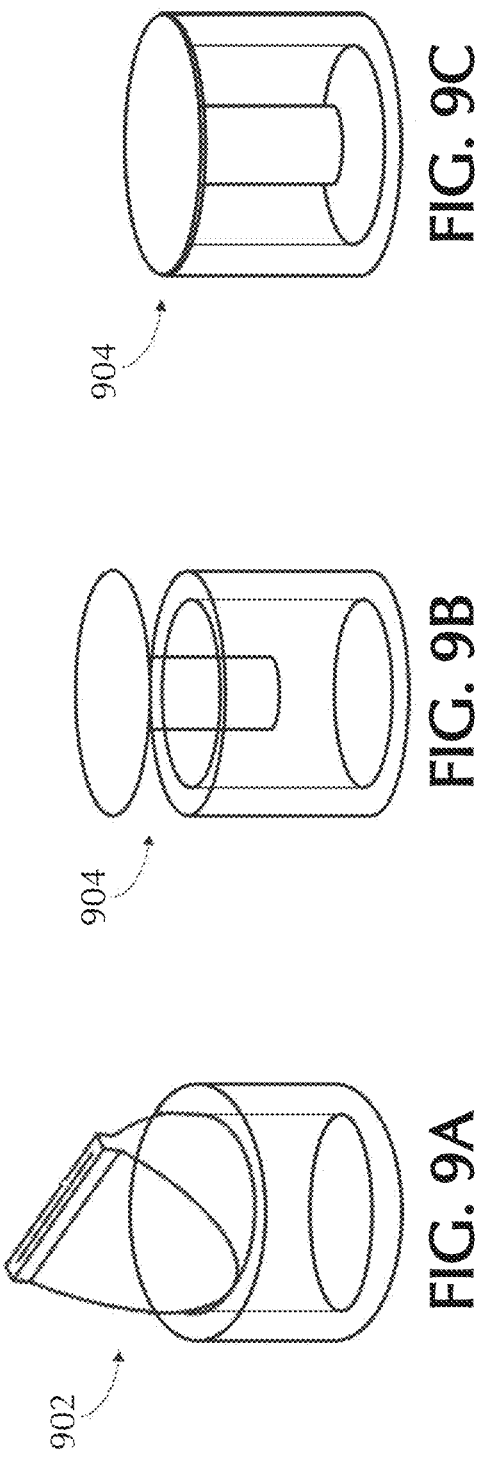

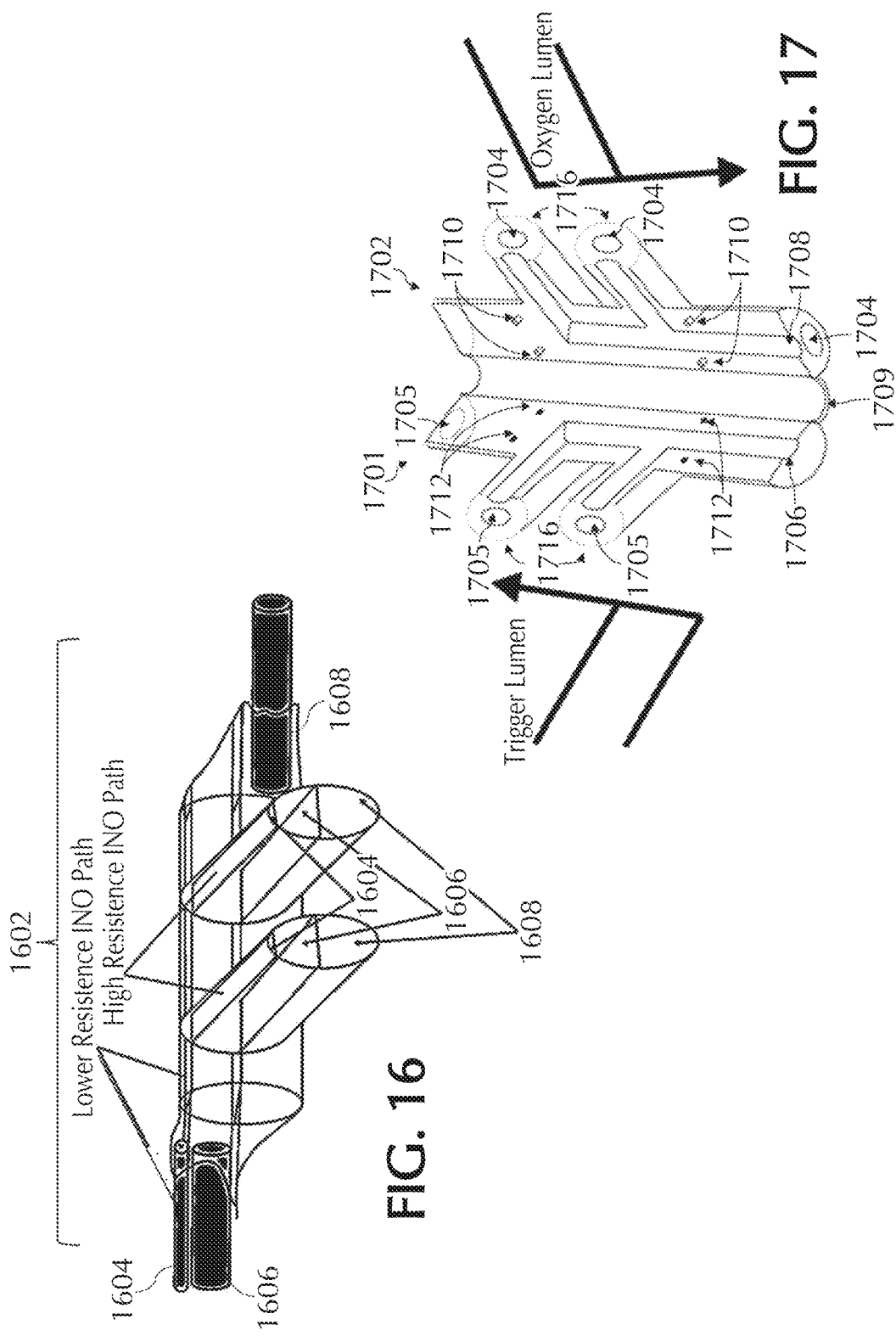

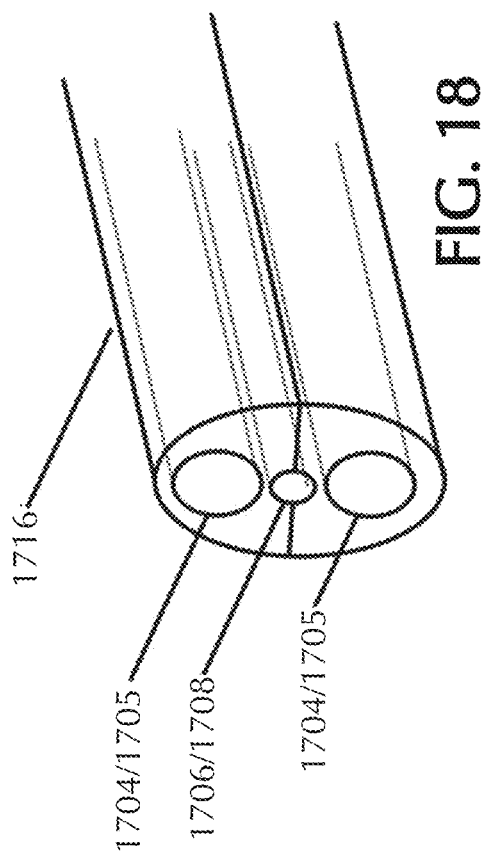
FIG. 18
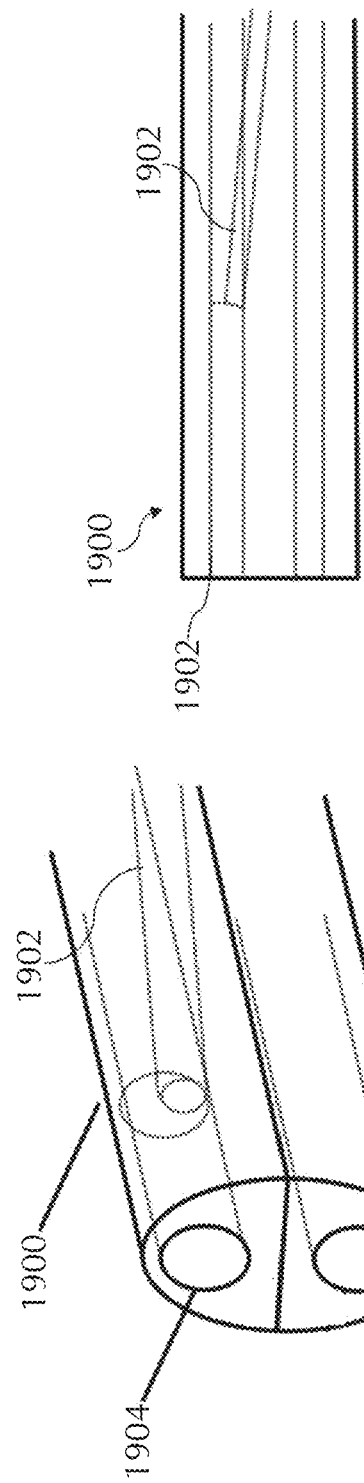
FIG. 19B
FIG. 19A

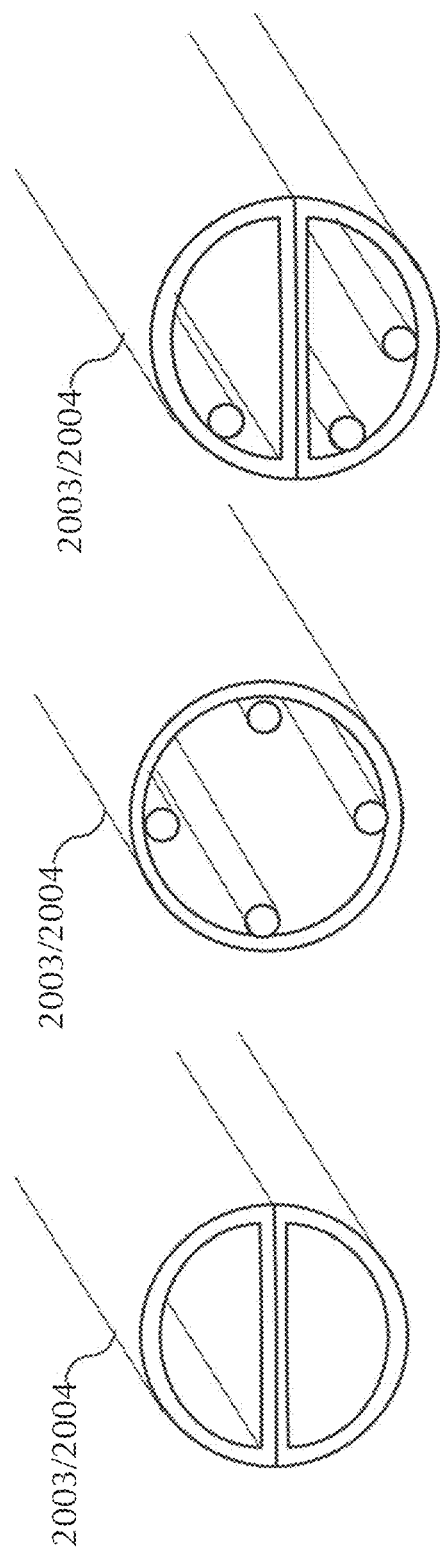
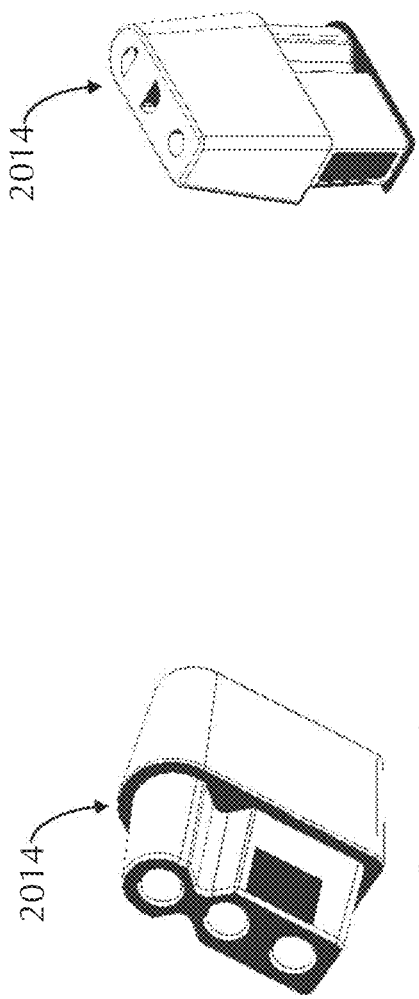
FIG. 21A  FIG. 21B  FIG. 21C
FIG. 22A  FIG. 22B

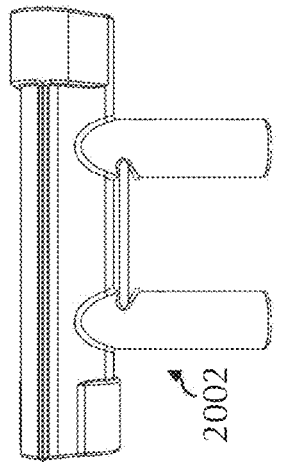
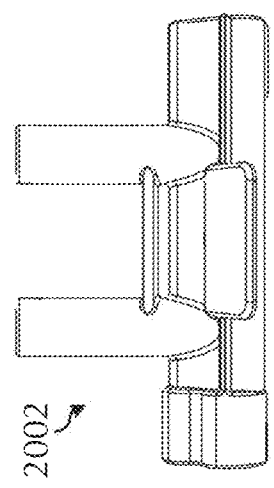
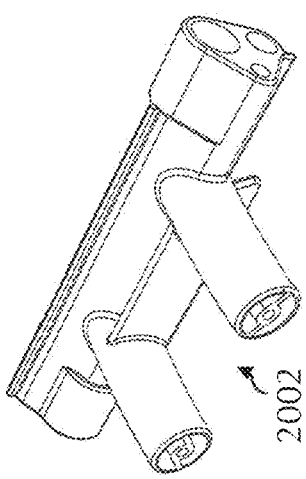
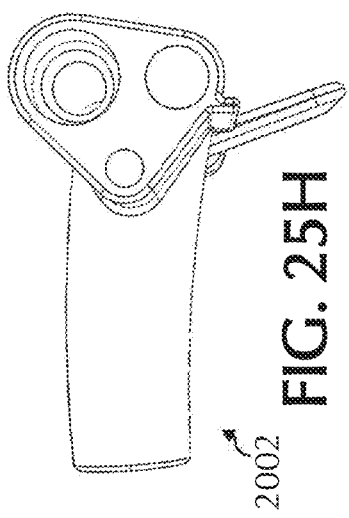
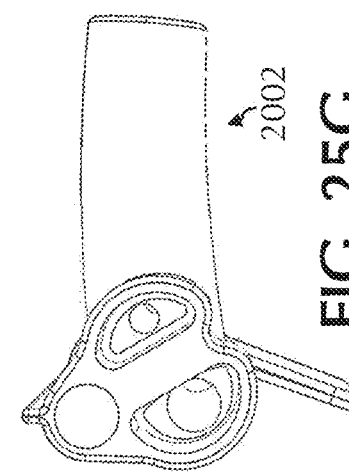
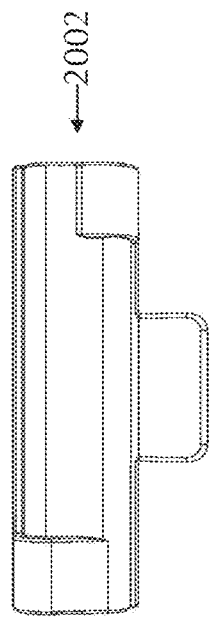
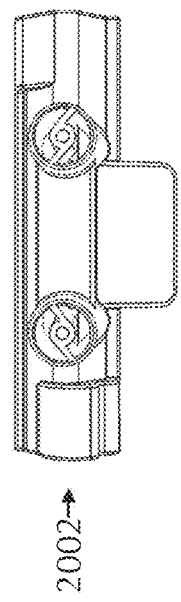

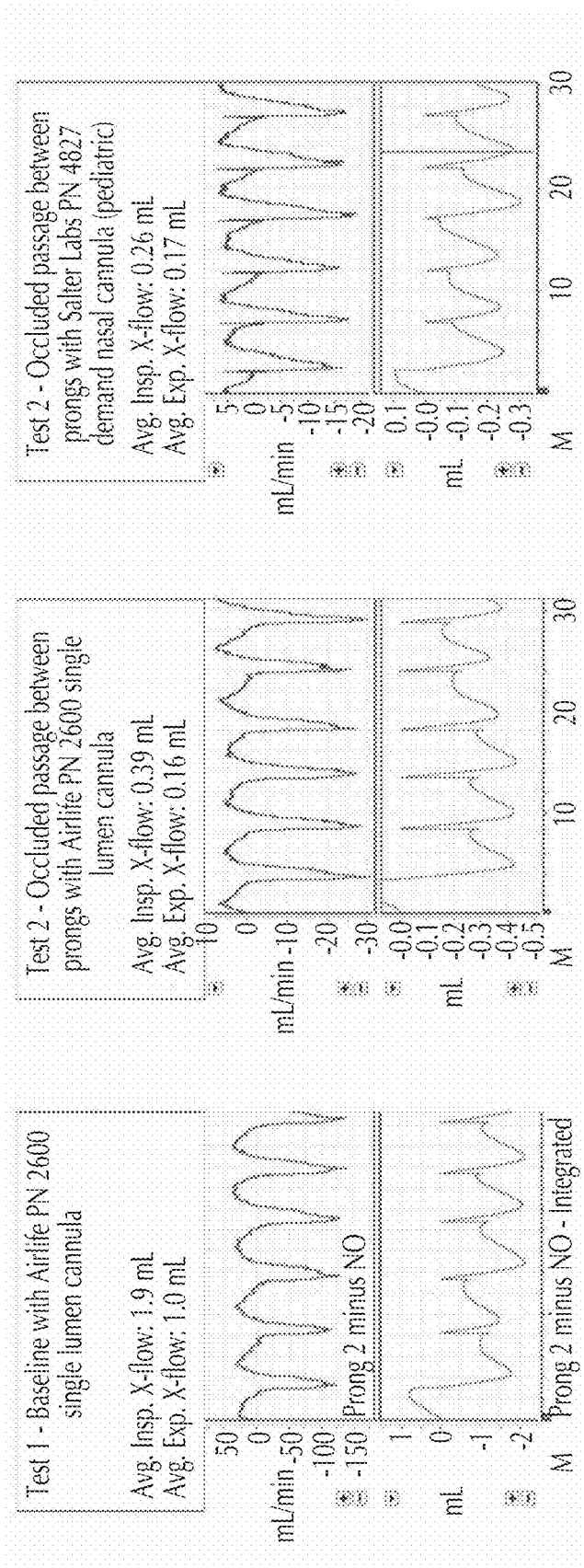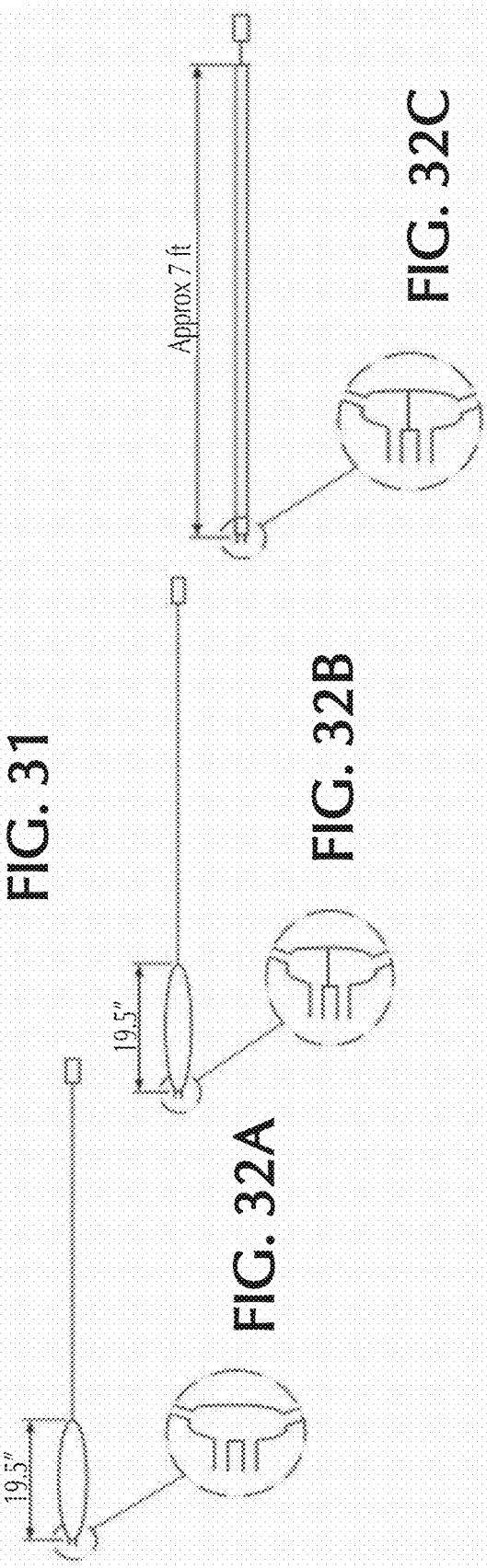
FIG. 31
FIG. 32A
FIG. 32B
FIG. 32C

CANNULA FOR MINIMIZING DILUTION OF DOSING DURING NITRIC OXIDE DELIVERY

CROSS-REFERENCE TO RELATED APPLICATIONS

This application is a continuation under 35 U.S.C. § 120 of U.S. patent application Ser. No. 15/412,348, filed Jan. 23, 2017, which is a continuation under 35 U.S.C. § 120 of U.S. patent application Ser. No. 14/312,003, filed Jun. 23, 2014, now U.S. Pat. No. 9,550,039, which is a continuation under 35 U.S.C. § 120 of U.S. patent application Ser. No. 14/096,629, filed Dec. 4, 2013, now U.S. Pat. No. 8,770,199, which claims, under 35 USC § 119(e), the benefit of U.S. Provisional Application No. 61/733,134, filed Dec. 4, 2012, U.S. Provisional Application No. 61/784,238, filed Mar. 14, 2013, and U.S. Provisional Application No. 61/856,367, filed Jul. 19, 2013, the contents of each of which are hereby incorporated by reference in their entireties.

TECHNICAL FIELD

The present invention generally relates to improving the accuracy and/or precision of nitric oxide therapy, reducing the dilution of inhaled nitric oxide, and/or ensuring mixing within the patient's nose.

BACKGROUND

Nitric oxide (NO) gas, when inhaled, dilates blood vessels in the lungs, improving oxygenation of the blood and reducing pulmonary hypertension. Because of this, some provide nitric oxide as a therapeutic gas in the inspiratory breathing gases for patients with pulmonary hypertension.

Typically, inhaled NO is delivered in a carrier gas from a high pressure source (e.g., a pressurized cylinder) to the patient at, or near, ambient pressure by means of a respiratory tube for ICU ventilator bound/dependent or anesthesia patients or a nasal cannula for spontaneously breathing patients. Delivering an accurate and consistent dose to the patient through a nasal cannula can be particularly challenging when the flow rate is pulsatile, for example, because dilution of the dose can occur.

Accordingly, a need exists for new methods and apparatuses for preventing dilution of dosing within the delivery conduit of a nitric oxide delivery apparatus, as well as methods of manufacturing such apparatuses.

SUMMARY

Aspects of the present invention relate to improved nasal cannulas that minimize retrograde flow and/or permeation of oxygen, air, and/or other gases during NO therapy while allowing NO delivery to one or both nares of the nostril. Such cannulas can reduce dilution of the delivered dose by using cannula materials and/or coatings that limit oxygen diffusion through the cannula walls and/or utilize cannula configurations that prevent mixing of co-delivered O2 and NO and/or reduce retrograde flow through the patient end of the cannula.

Aspects of the present invention also relate to methods of minimizing the dilution of the NO dose. Other aspects of the present invention pertain to methods of treatment utilizing these nasal cannulas and/or methods of administration. Other aspects of the present invention relate to methods of manufacturing multi-lumen cannulas and their nosepieces.

In exemplary embodiments, a nasal cannula of the present invention can be for delivering at least one therapeutic gas to a patient in need thereof. The nasal cannula can include a first lumen, a second lumen, and a third lumen. The nasal cannula can also include a cannula nosepiece. The first lumen can be capable of delivering a first therapeutic gas to a patient in need thereof, the second lumen can be capable of transmitting a pressure change to a pressure change sensor and/or breath sensor, the third lumen can be capable of delivering a second therapeutic gas to the patient, and/or the cannula nosepiece can include separate flow paths to the patient for the first lumen, the second lumen, and the third lumen. The at least one therapeutic gas can be nitric oxide.

In exemplary embodiments, a nasal cannula of the present invention can be used for therapeutic gas delivered to a patient. The nasal cannula can include a first lumen, a second lumen, and/or a third lumen. The first lumen can be a first therapeutic gas lumen for delivering a first therapeutic gas to a patient, the second lumen can be a triggering lumen, and the third lumen can be a second therapeutic gas lumen for delivering a second therapeutic gas to the patient. Further, a cannula nosepiece can allow separate flow paths to the patient for the first therapeutic gas lumen, the triggering lumen, and/or the second therapeutic gas lumen.

In exemplary embodiments, the nasal cannula can reduce dilution of one or more of the first and second therapeutic gases delivered to the patient and/or can be configured to be placed in fluid communication with at least one system to deliver the first and/or second therapeutic gases to the patient. The nasal cannula can inhibit mixing of nitric oxide and oxygen and/or the nasal cannula can reduce delivery of nitrogen dioxide to the patient.

In exemplary embodiments, one or more of the first and second therapeutic gases to the patient for treatment of pulmonary hypertension. In exemplary embodiments, the nasal cannula can deliver the first and/or second therapeutic gases to the patient for treatment of pulmonary hypertension, pulmonary hypertension secondary to chronic obstructive pulmonary disease (COPD), pulmonary hypertension as pulmonary arterial hypertension (PAH), pulmonary hypertension secondary to idiopathic pulmonary fibrosis (IPF), and/or pulmonary hypertension secondary to sarcoidosis. The first therapeutic gas and the second therapeutic gas can be different gases or the same gas. In exemplary embodiments, the first therapeutic gas can be nitric oxide and the second therapeutic gas can be oxygen and/or the first therapeutic gas lumen for delivering nitric oxide can be smaller than the second therapeutic gas lumen for delivering oxygen and/or the triggering lumen. In exemplary embodiments, the first therapeutic gas lumen can be for delivering nitric oxide and/or can be about six feet to about eight feet in length having an inner diameter of about 0.01 inches to about 0.10 inches. In exemplary embodiments, the triggering lumen can be about six feet to about eight feet in length having an inner diameter of about 0.05 inches to about 0.20 inches.

In exemplary embodiments, the first therapeutic gas can be nitric oxide and/or the cannula nosepiece can include a nitric oxide flow path that can have an inner diameter that may be smaller than an inner diameter of the first therapeutic gas lumen. In exemplary embodiments, the first therapeutic gas can be nitric oxide and/or the cannula nosepiece can include a nitric oxide flow path having a volume that may be less than about 10% of a minimum pulse volume of the pulse of nitric oxide. The cannula can include a wall material having a low oxygen transmission rate that can be between $$0.001 \frac{(cm^3)(mil)}{(24 \text{ hrs})(100 \text{ in}^2)(ATM)} \text{ and } 10 \frac{(cm^3)(mil)}{(24 \text{ hrs})(100 \text{ in}^2)(ATM)}.$$

In exemplary embodiments, the cannula can further include a fourth lumen that can be another first therapeutic gas lumen for delivering the first therapeutic gas to the patient. Further, the first lumen can deliver the first therapeutic gas to one nostril of the patient and the fourth lumen can deliver the first therapeutic gas to another nostril of the patient. In exemplary embodiments, the cannula can include at least one check valve in fluid communication with the first therapeutic gas lumen, a cannula key, a scavenging material, and/or a flexible support bridge that cushions the patient's nasal septum.

In exemplar embodiments, a nasal cannula of the present invention can be used for therapeutic gas delivered to a patient. The nasal cannula can include a first lumen, a second lumen, and a third lumen. The first lumen can be a first therapeutic gas lumen for delivering a first therapeutic gas to a patient, the second lumen can be a triggering lumen, and/or the third lumen can be a second therapeutic gas lumen for delivering a second therapeutic gas to the patient. The first therapeutic gas lumen, the triggering lumen, and the second therapeutic gas lumen can aggregate at a cannula nosepiece. The cannula nosepiece can allow separate flow paths to the patient for the first therapeutic gas lumen, the triggering lumen, and/or the second therapeutic gas lumen. The first therapeutic gas lumen can have an inner diameter that can be smaller than an inner diameter of the second therapeutic gas lumen and an inner diameter of the triggering lumen and/or the first therapeutic gas lumen can have an inner diameter that can larger than an inner diameter of the flow path for the first therapeutic gas lumen at the cannula nosepiece.

In exemplary embodiments, the nasal cannula can reduce dilution of the first and/or second therapeutic gases delivered to the patient and/or can be configured to be placed in fluid communication with at least one system to deliver the first and/or second therapeutic gases to the patient. The nasal cannula can inhibit mixing of nitric oxide and oxygen and/or the nasal cannula can reduce delivery of nitrogen dioxide to the patient.

In exemplary embodiments, one or more of the first and second therapeutic gases to the patient for treatment of pulmonary hypertension. In exemplary embodiments, the nasal cannula can deliver the first and/or second therapeutic gases to the patient for treatment of pulmonary hypertension, pulmonary hypertension secondary to chronic obstructive pulmonary disease (COPD), pulmonary hypertension as pulmonary arterial hypertension (PAH), pulmonary hypertension secondary to idiopathic pulmonary fibrosis (IPF), and/or pulmonary hypertension secondary to sarcoidosis. In exemplary embodiments, the first therapeutic gas lumen can be for delivering nitric oxide and can be about six feet to about eight feet in length having an inner diameter of about 0.01 inches to about 0.10 inches. The triggering lumen can be about six feet to about eight feet in length having an inner diameter of about 0.05 inches to about 0.20 inches.

In exemplary embodiments, the first therapeutic gas can be nitric oxide and the cannula nosepiece can include a nitric oxide flow path having a volume that can be less than about 10% of a minimum pulse volume of the pulse of nitric oxide. The cannula can include a wall material having a low oxygen transmission rate that can be between $$0.001 \frac{(cm^3)(mil)}{(24 \text{ hrs})(100 \text{ in}^2)(ATM)} \text{ and } 10 \frac{(cm^3)(mil)}{(24 \text{ hrs})(100 \text{ in}^2)(ATM)}.$$

In exemplary embodiments, the cannula can include at least one check valve in fluid communication with the first therapeutic gas lumen, a cannula key, a scavenging material, and/or a flexible support bridge that cushions the patient's nasal septum.

In exemplar embodiments, a nasal cannula of the present invention can be used for therapeutic gas delivered to a patient. The nasal cannula can include a first lumen, a second lumen, and a third lumen. The first lumen can be a first therapeutic gas lumen for delivering nitric oxide gas to a patient, the second lumen can be a triggering lumen, and the third lumen can be a second therapeutic gas lumen for delivering one or more of oxygen gas and air gas to the patient. The first therapeutic gas lumen, the triggering lumen, and/or the second therapeutic gas lumen can aggregate at a cannula nosepiece, the cannula nosepiece can allow separate flow paths to the patient for the first therapeutic gas lumen, the triggering lumen, and/or the second therapeutic gas lumen. The flow path for the first therapeutic gas lumen for delivering nitric oxide to the patient can have a volume at the cannula nosepiece that can be less than about 10% of a minimum pulse volume of the pulse of nitric oxide. The first therapeutic gas lumen can have an inner diameter that can be smaller than an inner diameter of the second therapeutic gas lumen and an inner diameter of the triggering lumen and/or the first therapeutic gas lumen can have an inner diameter that can be larger than an inner diameter of the flow path for the first therapeutic gas lumen at the cannula nosepiece.

In exemplar embodiments, a method for treating pulmonary hypertension can include administering nitric oxide gas to a patient in need thereof, wherein the nitric oxide can be administered through a nasal cannula, wherein the nasal cannula can include a first lumen, a second lumen, and a third lumen. In exemplary embodiments, nitric oxide is for treatment of pulmonary hypertension. In exemplary embodiments, the nasal cannula can deliver nitric oxide to the patient for treatment of pulmonary hypertension, pulmonary hypertension secondary to chronic obstructive pulmonary disease (COPD), pulmonary hypertension as pulmonary arterial hypertension (PAH), pulmonary hypertension secondary to idiopathic pulmonary fibrosis (IPF), and/or pulmonary hypertension secondary to sarcoidosis.

In exemplar embodiments, the nitric oxide can be pulsed early in inspiration and/or delivered in the first half of inspiration. In exemplar embodiments, the nitric oxide can be administered by pulsed inhalation to spontaneously breathing patients, the nitric oxide can be administered at the onset of inspiration, the dose of nitric oxide can be about 0.010 mg/kg/hr, and/or the dose can be administered at the onset of inspiration over a pulse width of less than 260 milliseconds. In exemplar embodiments, the method can further comprise administering oxygen to the patient.

In exemplar embodiments, a method of administering nitric oxide of the present invention can be used for treating pulmonary hypertension. The method can include administering nitric oxide gas to a patient, wherein nitric oxide can be administered through a nasal cannula. The nasal cannula can include a first lumen, a second lumen, and a third lumen. The first lumen can be a first therapeutic gas lumen for delivering a nitric oxide gas to a patient, the second lumen can be a triggering lumen, and the third lumen can be a second therapeutic gas lumen for delivering oxygen gas to the patient. Further, a cannula nosepiece can allow separate flow paths to the patient for the first therapeutic gas lumen, the triggering lumen, and/or the second therapeutic gas lumen. The second lumen can be for sensing the onset of inspiration and/or a change in pressure.

In exemplary embodiments, the nasal cannula can reduce dilution of one or more of the first and second therapeutic gases delivered to the patient and/or can be configured to be placed in fluid communication with at least one system to deliver the first and/or second therapeutic gases to the patient. The first therapeutic gas lumen for delivering nitric oxide can be smaller than both of the second therapeutic gas lumen for delivering oxygen and the triggering lumen. The first therapeutic gas lumen can have an inner diameter dimension that can be selected to be substantially small to reduce nitric oxide dilution by reducing transit time of NO through the cannula while also being substantially large enough to not cause significant backpressure and not substantially distort nitric oxide pulses and/or the triggering lumen can have an inner diameter dimension that can be selected to be substantially small while also can be substantially large enough to reduce delay and distortion of pressure signals. The cannula nosepiece can include a nitric oxide flow path that can have an inner diameter that can be smaller than an inner diameter dimension of the first therapeutic gas lumen.

In exemplary embodiments, the cannula can include at least one check valve in fluid communication with the first therapeutic gas lumen, a cannula key, a scavenging material, and/or a flexible support bridge that cushions the patient's nasal septum. The cannula can include a wall material having a low oxygen transmission rate that can be between $$0.001 \frac{(cm^3)(mil)}{(24 \text{ hrs})(100 \text{ in}^2)(ATM)} \text{ and } 10 \frac{(cm^3)(mil)}{(24 \text{ hrs})(100 \text{ in}^2)(ATM)}.$$

In exemplary embodiments, the cannula can further include a fourth lumen that can be another first therapeutic gas lumen for delivering the first therapeutic gas to the patient. Further, the first lumen can deliver the first therapeutic gas to one nostril of the patient and the fourth lumen can deliver the first therapeutic gas to another nostril of the patient.

BRIEF DESCRIPTION OF THE DRAWINGS

The features and advantages of various embodiments of the present invention will be more fully understood with reference to the following, detailed description when taken in conjunction with the accompanying figures, wherein:

FIGS. 3A and 3B, show an exemplary mono-lumen cannula, in accordance with exemplary embodiments of the present invention;

FIGS. 4 and 5A show an exemplary dual lumen cannula and/or exemplary pneumatic paths for the NO, oxygen, and trigger lumens, in accordance with exemplary embodiments of the present invention;

FIG. 5B shows an exemplary cannula nosepiece of a dual-lumen cannula and/or pneumatic paths, in accordance with exemplary embodiments of the present invention;

FIGS. 6C and 7 show exemplary cannula nosepieces of a tri-lumen cannula and/or pneumatic paths, in accordance with exemplary embodiments of the present invention;

FIGS. 8C and 8D show exemplary cannula nosepieces of a quad-lumen cannula and/or pneumatic paths, in accordance with exemplary embodiments of the present invention;

FIG. 9A shows an exemplary duck bill check valve, in accordance with exemplary embodiments of the present invention;

FIGS. 9B and 9C show exemplary umbrella and/or flapper check valves, in accordance with exemplary embodiments of the present invention;

FIG. 16 shows an exemplary nasal cannula with a tri-lumen nosepiece, in accordance with exemplary embodiments of the present invention;

FIG. 17 shows an exemplary tri-lumen nosepiece prior to assembly, in accordance with exemplary embodiments of the present invention;

FIG. 18 shows an exemplary nasal prong of the assembled molded tri-lumen nosepiece, in accordance with exemplary embodiments of the present invention;

FIGS. 19A-19B shows a perspective and a two-dimensional representation of an exemplary nasal prong with a NO lumen proximal to and within a trigger lumen, in accordance with exemplary embodiments of the present invention;

FIG. 21A shows an exemplary dual "D" shaped paratube, in accordance with exemplary embodiments of the present invention;

FIGS. 21B and 21C show exemplary lumina having geometric protrusions and/or inserts, in accordance with exemplary embodiments of the present invention;

FIGS. 22A-22E views of exemplary nasal cannula device connection pieces, in accordance with exemplary embodiments of the present invention;

FIG. 25D shows a front top right perspective view of an exemplary cannula nosepiece, in accordance with exemplary embodiments of the present invention;

FIG. 25E shows a bottom view of an exemplary cannula nosepiece, in accordance with exemplary embodiments of the present invention;

FIG. 25F shows a top view of an exemplary cannula nosepiece, in accordance with exemplary embodiments of the present invention;

FIG. 25G shows a first side view of an exemplary cannula nosepiece, in accordance with exemplary embodiments of the present invention;

FIG. 25H shows a second side view of an exemplary cannula nosepiece, in accordance with exemplary embodiments of the present invention;

FIG. 25I shows a front view of an exemplary cannula nosepiece, in accordance with exemplary embodiments of the present invention;

FIG. 25J shows a back view of an exemplary cannula nosepiece, in accordance with exemplary embodiments of the present invention;

FIG. 31 illustratively depicts exemplary retrograde flows for various exemplary cannula configurations, in accordance with exemplary embodiments of the present invention;

FIGS. 32A-32C show exemplary cannula configurations for Tests 1-3 of FIG. 31, in accordance with exemplary embodiments of the present invention;

DETAILED DESCRIPTION

The present invention generally relates to, amongst other things, systems, devices, materials, and methods that can improve the accuracy and/or precision of nitric oxide therapy by, for example, reducing the dilution of inhaled therapeutic gases such as nitric oxide (NO) and/or limiting mixing of the inhaled therapeutic gases prior to delivery into the patient's nose. As described herein, NO dilution can occur because of various factors such as, but not limited to, NO mixing with oxygen and/or air. To reduce the dilution of an intended NO dose, various exemplary nasal cannulas, pneumatic configurations, methods of manufacturing, and methods of use, etc. are disclosed. For example, the various exemplary nasal cannulas, pneumatic configurations, methods of manufacturing, and methods of use, etc. of the present invention can reduce mixing of NO with oxygen and/or air (e.g., prior to being delivered into the patient's nose, etc.) thereby reducing dilution of intended NO doses.

Due to the unique nature of NO delivery, many factors need to be considered to ensure accurate and precise delivery of doses of NO to the patient. Unlike the administration of other gases, such as oxygen (O2), NO dosing can be particularly susceptible to dilution because, amongst other things, the dose volume may be less than 1 ml (e.g. a substantially small dose that can be lost to ambient) and/or NO can be reactive with O2 present in ambient air and/or co-administered O2 producing nitrogen dioxide (NO2). Further, the timing of NO delivery can also be more critical (e.g., for efficacy) than the timing of other gases (e.g., O2 delivery), so a need exists to reduce NO dilution and ensure that the beginning of a patient's breath can be accurately determined as soon as possible and/or to ensure that the NO dose waveform does not significantly distort while traveling through the nasal cannula from the NO delivery device to the patient. Further, patient comfort may need to be factored into the design of the nasal cannula, for example, because the nasal cannula may be used for prolonged periods of time.

Various cannulas, systems, and methods of the present invention can use, modify, and/or be affiliated with various systems for delivering pharmaceutical gas to a patient and/or for delivering a pulse of pharmaceutical gas to a patient. For example, the various cannulas, systems, and methods of the present invention can use, modify, and/or be affiliated with at least the therapeutic gas delivery systems illustratively depicted in FIGS. 33A-34H. The various cannulas, systems, and methods of the present disclosure can use, modify, and/or be affiliated with the teachings of U.S. Pat. No. 7,523,752 entitled "System and Method of Administering a Pharmaceutical Gas To a Patient", the content of which is incorporated herein by reference in its entirety.

Figure 1:
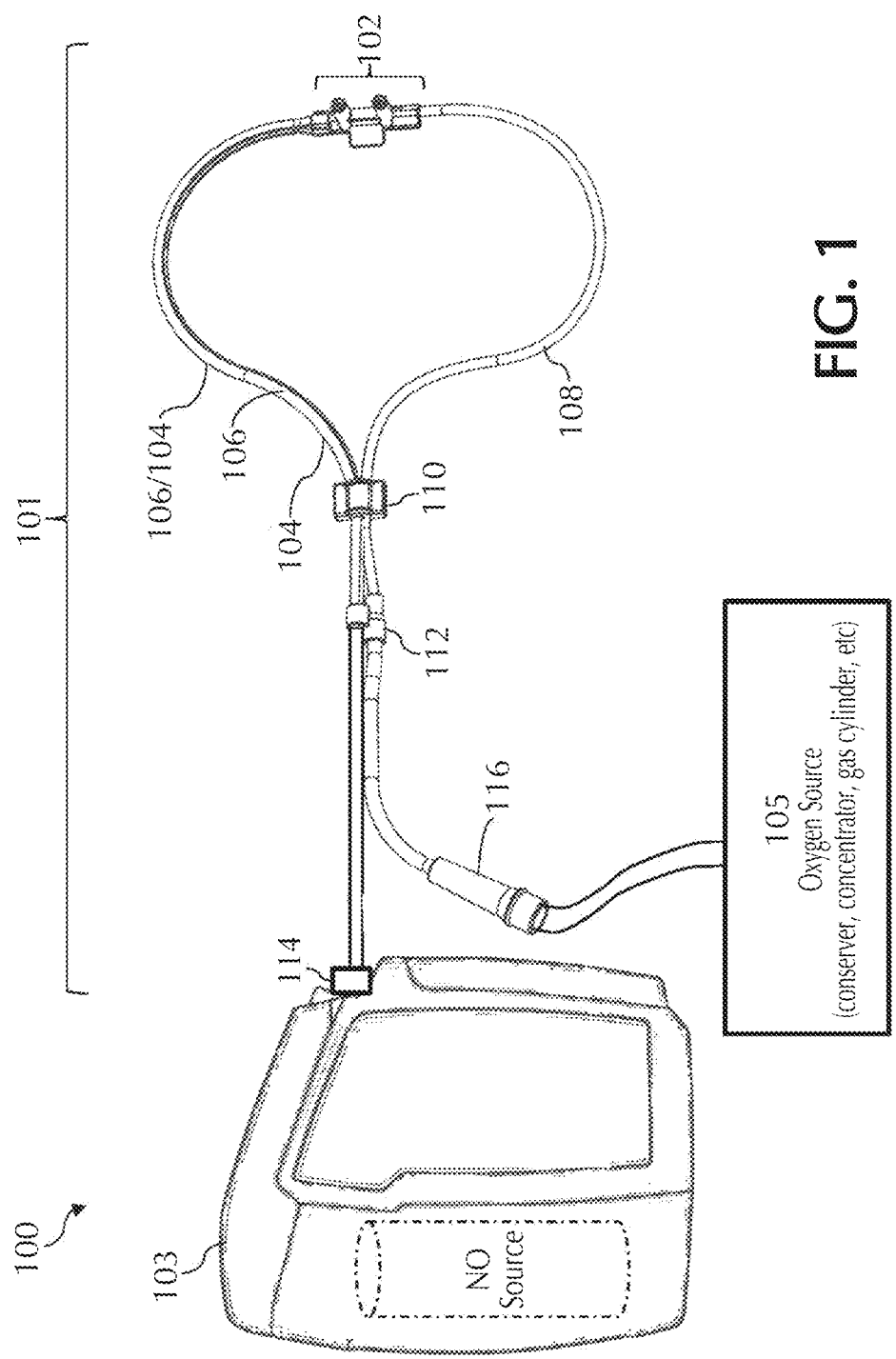
FIG. 1, shows an exemplary nasal cannula, in accordance with exemplary embodiments of the present invention.

Referring to FIG. 1, typically, using a delivery system 100 NO can be delivered to a patient via a nasal cannula 101. Nasal cannula 101 can receive NO at relatively low volumetric percent concentrations in a carrier gas from, for example, a therapeutic gas (e.g., NO) delivery device 103 and/or nasal cannula 101 can receive oxygen and/or ambient air (at times referred to simply as oxygen, O2, etc.) from an oxygen/ambient air supply 105. A commonly used carrier gas is nitrogen because nitrogen is non-reactive with NO, but other inert carrier gases such as helium can be used.

Delivery of the NO/N$_2$ gas mixture (at times referred to simply as nitric oxide, NO, etc.) to the patient typically requires that the NO gas travel from a high pressure NO source (e.g., a pressurized cylinder, pressurized cylinder affiliated with NO delivery device 103, etc.) to the patient at, or near, ambient pressure, for example, via a delivery tube for ICU ventilator bound/dependent and/or anesthesia patients and/or via a nasal cannula for spontaneously breathing patients. It will be understood that various techniques and/or embodiments of the invention disclosed herein can be used for a delivery tube and/or a nasal cannula as well as other like apparatuses such as nasal pillows and/or nasal masks, to name a few. For ease, at times only a cannula is shown and/or described. This is merely for ease and is in no way meant to be a limitation.

This above described transit of the NO, ideally, will be devoid of contact with other gasses, such as ambient air, oxygen, carbon dioxide, etc., until the gas enters the patient's upper respiratory tract. However, in practice, this may not be easily achieved. By way of example, oxygen and/or ambient air can enter delivery system 100 at a number of points such as, but not limited to:

During the transit time within delivery device 103 (e.g., due to oxygen diffusion through pneumatic interfaces such as elastomeric O-rings into the inner pneumatics of the delivery device, etc.);

During the NO gas transit through nasal cannula 101 (e.g., by way of diffusion across the cannula wall, nosepiece, connectors, reducer, bond joints, etc.);

During the inhalation/exhalation cycle when a driving pressure gradient can reverse flow in the nasal cannula NO supply lumen producing mixing within nasal cannula 101 with ambient air and/or exhaled gas;

During the inhalation/exhalation cycle when NO and Air/O2 get mixed in the patient nares;

During the connection of the high pressure source (e.g., a pressurized cylinder, etc.) to the delivery device (e.g., as cylinder replacement can trap small amounts of gas in the delivery pneumatics, etc.); and During the manufacturing cylinder filling operation of the high pressure NO source in which a substantially pure mixture of NO and carrier gas can be sought, but may not be easily achieved.

The dilution of NO during pulsed NO therapy can be problematic because only a substantially small volume of NO may be delivered to the patient. For example, the NO-containing gas can be administered in pulses that may be less than one (1) milliliter (ml). With substantially small pulse volumes, even small volumes of retrograde flow and/or diffused gases can be significant, for example, because the small NO dose may be easily diluted. Of course larger volumes of NO can also be diluted.

Minimization of NO/O2 Contact Due to O2 Diffusion

Minimization of NO Transit Time

One or more embodiments of the present invention relate to nasal cannulas that address sources of NO/O2 contact (e.g., one or more of the above sources of NO/O2 contact) and thereby dilution (e.g., by mixing of NO with O2, etc.) of the intended NO dose by minimizing NO contact time with O2, via minimizing transit time through the cannula, minimizing the transit of oxygen across the cannula walls, and/or minimizing the amount of O2 coming in contact with NO. Referring to FIG. 1, addressing at least dilution of intended NO doses, described below in greater detail, oxygen transit can be minimized across any lumina wall of cannula 101 such as, but not limited to, cannula walls associated with a trigger lumen 104, NO lumen 106, O2/air lumen 108, and/or any combination and/or further separation thereof, to name a few. Also, addressing at least dilution of intended NO doses, oxygen transit can be minimized across any wall of cannula 101, such as but not limited to, cannula walls associated with a cannula nosepiece 102, a keying member 110, reducer 112, connection piece 114, oxygen connection piece 116, and/or any combination and/or further separation thereof, to name a few.

Small ID NO Lumen

In one or more embodiments, cannulas can be provided that include a smaller inside diameter (ID) delivery tube/ lumen for NO to, for example, reduce dilution of the intended NO doses. This smaller ID tube can reduce the transit time of the NO molecules through the cannula. This in turn can reduce the time available for mixing with oxygen which can be diffusing across the walls of the cannula and oxidizing the internal NO into NO2.

By way of example, to reduce dilution of intended NO doses by minimizing NO transit time through the cannula, the ID for delivery tube/lumen for NO can be about 0.01 inches to about 0.10 inches and/or about 0.03 inches to about 0.08 inches. In exemplary embodiments, the ID of the delivery tube/lumen for NO can be selected to ensure reduced transit time of NO (e.g., reducing NO dilution, etc.) while not resulting in significant backpressure and/or NO pulse shape distortion and/or NO waveform distortion (discussed below in greater detail). To reduce transit time as well as not significantly cause backpressure and/or distortion, the ID for delivery tube/lumen for NO may not be substantially smaller than about 0.03 inches, for example, for a cannula having a length of about 6 feet to 8 feet. For shorter lengths a smaller ID may be used and/or for longer lengths a larger ID may be used as resistance and/or distortion can be a function of both tube ID and tube length.

In exemplary embodiments, the ID of shorter tubes/lumens for NO delivery (e.g. such as the cannula nares, shorter nasal cannulas, etc.) can have a substantially smaller tube ID than for delivery tubes/lumen for NO, which may also have a substantially small ID as described above, without significant backpressure and/or NO pulse shape and/or waveform distortion occurring.

In exemplary embodiments, the potential for time of exposure of NO to O2 can be minimized using other techniques such as, but not limited to, increasing the velocity of delivery of NO through the NO lumen. The velocity of NO through the NO lumen can be increased by, for example, increasing the pressure gradient within the system and/or by reducing the diameter of the tube. Although the NO velocity can be increased to reduce the exposure time of NO to O2, the velocity can be required to be minimized so that the pulse shape is not substantially distorted, the patient does not experience discomfort, and/or by factoring in any other competing metric.

It will be understood that the any of above teachings (e.g., small ID for the delivery tube lumen for NO, etc.) can be combined with any of the other pneumatic configurations, cannula configurations, and/or teachings and/or embodiments described herein. For example, the above teachings (e.g., small ID for the delivery tube/lumen for NO, etc.) can be used with the below described mono-lumen cannulas, dual-lumen cannulas, tri-lumen cannulas, quad-lumen cannulas, and/or any other teachings and embodiments described herein.

Materials to Limit Oxygen Diffusion and/or Remove O2 and/or NO2

Currently, many use polyvinyl chloride (PVC) and/or silicone as a common material for constructing nasal cannulas; however, oxygen can diffuse through the lumen walls of these nasal cannulas. To minimize the oxygen contact occurring due to oxygen diffusion, permeation, and/or transmission across the cannula's walls, cannula wall materials can be selected that minimize the oxygen diffusion rate, permeability rate, and/or oxygen transmission rate (OTR). In exemplary embodiments, the cannula wall can include a material with a low oxygen diffusion coefficient, permeability rating, and/or oxygen transmission rate (OTR). By way of example, the cannula wall can include a material that can have an oxygen transmission rate (OTR) from about 0.001 to about 10, for example, using the following units:

$$\frac{(cm^3)(mil)}{(24 \text{ hrs})(100 \text{ in}^2)(ATM)}$$

where:
"cc" refers to the cubic centimeters (ml) of oxygen that crosses a square of material;
"mil" refers to 1 mil (0.001" thickness) of the square of material;
"ATM" refers to the number of atmospheres of ambient pressure;
"24 hrs" refers to the duration allowed for oxygen flow; and
"100 in$^2$" refers to the surface area of the square of material.

At times, when describing oxygen diffusion, permeation, and/or transmission across the cannula's walls and/or cannula's materials, reference may only be made to at least one of diffusion rates, diffusion coefficients, permeability rates, permeability ratings, and/or OTR. It will be understood that reference to any of the above terms, when applicable, can be used with and/or replaced by any of the above terms, and the like. For ease, at times only one and/or some of the above terms are described. This is merely for ease and is in no way meant to be a limitation.

In exemplary embodiments, cannula materials (e.g., material for the cannula tubing, the cannula nosepiece, etc.) can be adjusted and/or varied to address O2 permeation along with patient comfort.

In exemplary embodiments, cannulas can be constructed using polyurethane and/or similar soft material. In exemplary embodiments, the polyurethane and/or similar soft material can include an additive to enhance the resistance to oxygen diffusion and/or tube coaxially located about at least some of the cannula for NO delivery filled with a gas providing resistance to oxygen diffusion. The cannulas can be constructed by coaxially coating a tube and/or co-extruding two or more materials (e.g., to form the tube, etc.). Of course other methods and/or techniques for construction are within the scope of the disclosure.

Examples of at least some materials which can be used for construction and/or that can have desired oxygen permeation properties include, but are not limited to, polymers such as polyvinylidene chloride (PVDC), ethylene vinyl alcohol (EVOH), polyamide (PA), polyvinylidene difluoride (PVDF), fluorinated polyurethane, Nylon 6, Nylon 12, and/or similar materials, to name a few. Further, PVC can be used as the cannula material with one or more materials and/or additives, such as oxygen resistant polymers, incorporated to reduce the oxygen permeation, diffusion coefficient, and the like. Oxygen resistant polymers can be incorporated with the polyurethane, PVC, and/or other cannula materials, for example, through co-extrusion. By way of example, such an extrusion can be achieved with co-extrusion dies and/or using other known techniques.

Tubing/lumen barriers to oxygen ingress can take one of a number of potential forms such as, but not limited to:
Homogenous and/or single material extrusions that can use at least one material with low oxygen permeation characteristics;

Co-extrusions of two or more polymers, one or more of the polymers having low oxygen permeation characteristics;

Surface treatment/surface coatings over materials/tubing with such coatings can have low oxygen permeation characteristics;

Blends; and

Scavengers/getters/purifiers.

Homogenous and/or single material extrusions with low oxygen permeability: In exemplary embodiments, materials such as polyvinylidine chloride (PVDC, trade name Saran®), ethylene vinyl alcohol (EVOH), Nylon 6, Nylon 12, and/or any homogenous and/or single material extrusions with low oxygen permeability can be used for the cannula material. Other materials are envisioned with these properties and the use of substitute low oxygen permeation extrusion compatible material is within the scope of this invention.

Co-extrusions of two or more polymers: In exemplary embodiments, a tube-in-tube and/or multilayered sandwich configurations can be constructed using co-extrusions of two or more polymers. For example, two or more polymers, with at least one having low oxygen permeation properties, can be co-extruded (e.g., using common co-extrusion methods known in the art) to construct a tube-in-tube or multilayered sandwich configuration. The low oxygen permeation layer can include the polymers disclosed herein (e.g., such as those listed in the previous section) and/or other polymers with similar characteristics. Since these polymers may or may not co-extrude well with other polymers, it may be necessary to extrude an intermediate or so called tie-layer polymer. Exemplary co-extruded polymers can include, but are not limited to, PVC/EVOH/PVDC, PVC/EVOH/PFDF, fluorinated polyurethane/EVOH/PVDC and fluorinated polyurethane/EVOH/PVDF, PVC/PVDC, Polyurethane/PVDC, PVC/Nylon 6, PVC/Nylon 12, PVC/PVDC/Nylon 6, PVC/PVDC/Nylon 12, Polyurethane/PVDC/Nylon 6, Polyurethane/PVDC/Nylon12, tie layer polymers, any combination and/or separation thereof, and/or any other material that can be used with co-extrusions of two or more polymers.

In exemplary embodiments, co-extrusions can be layered in a specific order, for example, to reduce oxygen permeation and/or diffusion and/or for construction purposes. For example, if an adhesive used (e.g., in the joining of components of the cannula, etc.) bonds PVC to PVC then the outer layer of a co-extrusion exposed to such adhesive can be PVC. Further, additional polymers (e.g., which may have reduced properties when in contact with water vapor) such as, but not limited to, EVOH can be sandwiched inside hydrophobic and/or water resistant outer and/or inner extrusion layers to minimize the contact of the internal compound with water vapor.

Surface treatment/surface coatings over tubing: In exemplary embodiments, surface coatings (e.g., surface treatments, surface coatings, etc.) for low oxygen permeation can be applied to nasal cannula construction. Such coatings can include, but are not limited to, vacuum deposited silicon dioxide (silica) and/or aluminum (e.g., oxides of aluminum, etc.) coatings heated above their sublimation temperature that can be deposited in thin layers a few microns (or less) thick. For example, silica coatings can be about 0.001 microns to about 10 microns and/or about 0.01 microns to about 1 micron, and/or about 0.04 microns.

In exemplary embodiments, silica coatings can be deposited on plastic in layers that can be substantially thin enough such that flexibility of the plastic may not be materially affected. It will be understood that any reasonable technique can be used for deposition of such materials. For example, low cost deposition can be achieved using chemical vapor deposition treatment. Of course other deposition methods for these coatings can also be used such as, but not limited to, E-beam and Thermal Evaporation, DC Magnetron Sputtering, Plasma-Assisted Reactive Sputtering, any combination and/or further separation thereof, and/or any technique capable of deposition.

In exemplary embodiments, other coatings such as, but not limited to, thermoset epoxy-amine coatings, epoxy-amine coatings, etc. can be used. Coatings can be applied and/or provided using techniques described herein and/or known techniques.

Blends: In exemplary embodiments, materials can be blended together to obtain the beneficial properties of one or the other materials and/or used as the cannula material. In exemplary embodiments, Nylon 6 and EVOH, which can adhere to each other in co-extrusions without the need for a tie layer, can be used as a blended cannula material. Other blends can include, but are not limited to, Nylon 6 with amorphous nylon and Nylon 6 with HDPE. Of course other blends can be used.

In exemplary embodiments, a later material can be coated over an earlier material. By way of example, when two materials are not compatible with co-extrusion due to different melt temperatures, one polymer can be extruded first and the second polymer can be heated and coated over the first in a secondary operation.

Scavengers/getters: In exemplary embodiments, scavengers can be coated to the inside of the lumen (e.g., by baking off the liquid in a liquid suspension of the scavenger to the inside of the lumen, by condensing out the scavenger on the inside of the lumen by evaporative processes, by absorbing/adsorbing to the inside surface of the lumen using a liquid or gaseous scavenger source, by chemically bonding the scavenger to the inside surface of the cannula, etc.) and/or the scavenger can be packaged within the device connector and/or nosepiece, for example, as a plug (e.g., a plug with at least one hole to allow flow of gas through it, etc.) to scavenge oxygen and/or nitrogen dioxide. Such scavengers can include, but are not limited to, compounds such as activated alumina, ascorbic acid, and/or any other scavenging compound. Potential drawbacks of such an approach include the finite lifespan of the scavenging material. This drawback can be overcome by factoring in use duration of the cannula into the design. At least one additional potential drawback can be that any plug configuration for gas transit through a scavenger may distort the gas waveform. In light of this plugs described may be designed to minimize such waveform distortion. Any method can be used to coat the inside of the lumen. By of example, a liquid that is concentrated with a scavenger (e.g., ascorbic acid) can be passed through the tube and then dried on such that it may then be deposited on the inner wall of the tube.

In exemplary embodiments, activated alumina can be used in the cannula, for example, as a coating in the inside of the lumen, as a plug fitting, and/or used in any other way, for example, for the capture of nitrogen dioxide. With a thin layer of alumina coated to the inside of the lumen, the effect can not only be a reduction of the oxygen permeation rate, but can also be successful for capture of nitrogen dioxide. Activated alumina and/or other scavengers can also be made in the form of a plug fitted into the tube, for example, in an area close in proximity to the nostrils of the patient. The plug may be designed to minimize pressure drop and/or to maintain the shape of nitric oxide pulse wave. The high surface area of activated alumina can effectively scrub nitrogen dioxide from the gas mixture. Further, the scavenger can also be located in the device, for example, at the device connector. In this fashion, the scavenger can be part of the cannula and/or may be removable (e.g., such that it may be removed when changing the cannula) and/or the design life of the scavenger can be matched to anticipated and/or actual use duration of the cannula.

It will be understood that the invention is not limited to activated alumina and that any material with a high surface area, substantial nitrogen dioxide scrubbing capability, proper pore sizes, enough physical strength so that the shape could be maintained, and/or that may not generate powders and/or other materials that may shed or decouple from the cannula can act in the capacity of the scrubbing material. It is further understood that internal filtering may be used to contain shedding compounds to prevent aspiration in the respiratory system. Examples of scrubbing materials include, but are not limited to, zeolites, silica-alumina, activated carbon/coal, and adsorbents that can have solid base sites on the surface. For ease, at times, activated alumina is described as a scrubbing material. This is merely for ease and is in no way meant to be a limitation.

In exemplary embodiments, a reducing agent can be coated on the surface of the scrubbing material, for example, to enhance its ability to capture and/or reduce nitrogen dioxide to nitric oxide. Such reducing agents include, but are not limited to, ascorbic acid.

In exemplary embodiments, additives can be added to the polymer to change the permeation/barrier properties such as, but not limited to, oxidizable plastic (e.g. PET or polyamide), nanoclays, any combination and/or further separation thereof, and/or any other additive. Additives can work to scavenge the oxygen and/or provide a barrier to permeation within the polymer matrix, either of which can result in reduced oxygen permeating through the material. Oxidizable plastics (e.g. PET or polyamide) can react with the oxygen that may be permeating through the polymer matrix. Oxygen that may be permeating through the membrane can react with the oxidizable plastic prior to getting through the cannula and/or reacting with NO. Nanoclays (e.g., that may tend to have a plate like morphology) can provide a barrier to permeation, for example, when adequately dispersed within the polymer matrix. When dispersed, diffusion can be required to occur around the plates, which can result in a tortuous path through the polymer thereby effectively reducing the gas permeability.

It will be understood that the any of above teachings (e.g., materials, etc.) can be combined with any of the other pneumatic configurations, cannula configurations, and/or teachings and/or embodiments described herein. For example, the above teachings (e.g., materials, etc.) can be used with the below described mono-lumen cannulas, dual lumen cannulas, tri-lumen cannulas, quad lumen cannulas, and/or any other teachings and/or embodiments described herein.

Configurations

Retrograde Flow

Figure 2A:
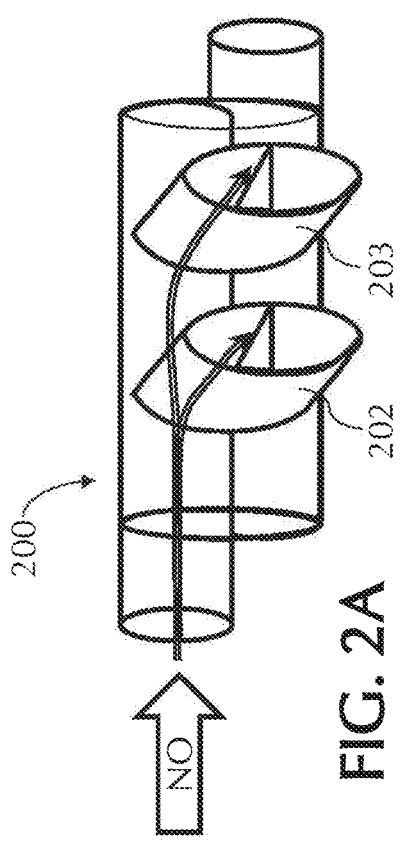
FIG. 2A shows an exemplary flow directionality of NO gas during delivery to patients, in accordance with exemplary embodiments of the present invention.
Figure 2B:
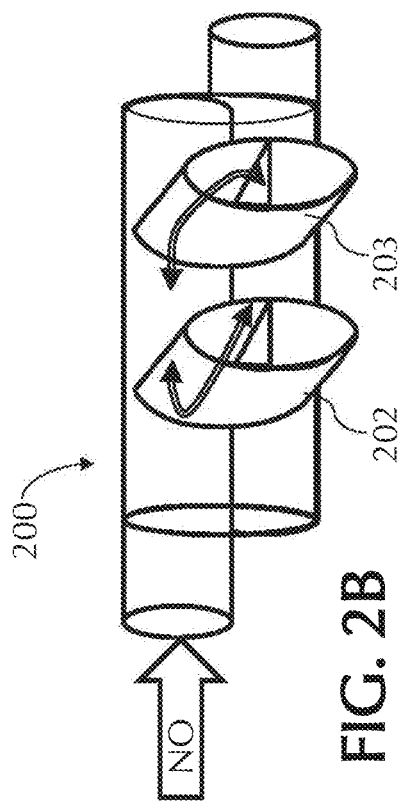
FIG. 2B shows an exemplary retrograde flow path, in accordance with exemplary embodiments of the present invention.
Figure 12:
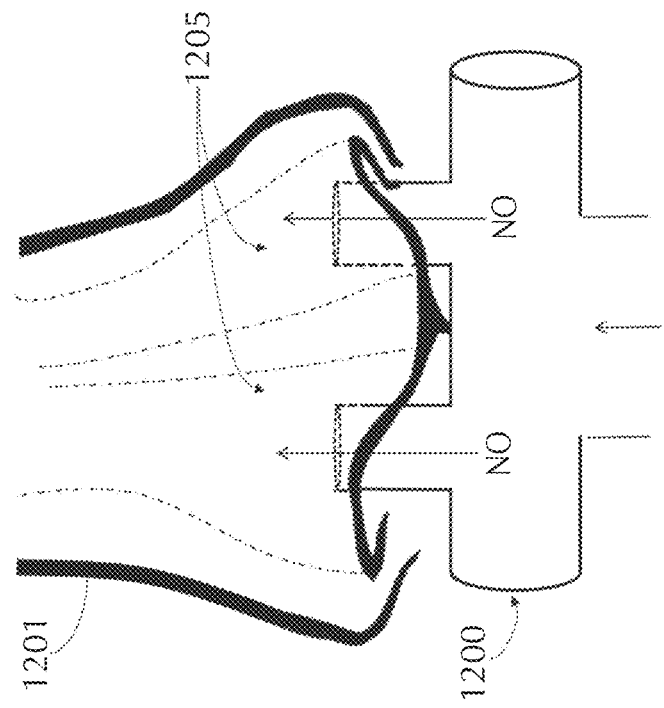
FIG. 12 shows exemplary flow from a blocked nostril to the patient's other nostril, in accordance with exemplary embodiments of the present invention.

Referring to FIGS. 2A-2B, it was surprisingly found that another source of dilution can be caused by a phenomenon (e.g., retrograde flow, cross-flow, etc.) in which ambient air and/or exhaled gas flows into the nasal cannula (e.g., at and/or near cannula nosepiece 200). This gas flow into the nasal cannula can be between two cannula nares (e.g., cannula nares 202/203) displacing resident nitric oxide gas and/or pushing the nitric oxide gas out of the cannula so the displaced and/or pushed out nitric oxide may not be delivered to the patient and/or may mix with the gas flow and/or other gases, thereby diluting the intended NO dose. Further, retrograde flow can depend on factors such as, but not limited to, the pressure difference between the nares during both inhalation and exhalation. The pressure difference between the nares can vary depending on factors such as, but not limited to, the person's breathing pattern, occlusions and/or partial occlusions in the person's nostrils (e.g., as shown in FIG. 12), placement of the nasal nares, and the degree of misbalance between the nasal flow during breathing, to name a few. Accordingly, one or more embodiments of the present invention relate to nasal cannulas that can minimize the retrograde flow and/or dilution resulting from retrograde flow in the nasal cannula.

As shown in FIG. 2A, during normal pulsed delivery, NO flows out of both nares 202/203 of cannula nosepiece 200. However, during at least the static phase between pulses, retrograde flow can occur. For example, during the static phase ambient or exhaled air can flow in a circular motion and/or reversed flow in through one cannula nare 202 and out the other cannula nare 203 as shown in FIG. 2B. This retrograde flow can result in dilution and/or washout of NO in the nasal nares and/or flow path, which can cause a delay and/or reduction in the delivered dose. Furthermore, this retrograde flow can result in the oxygen in air and/or exhaled gas stream mixing with the NO to a greater degree and/or reacting with nitric oxide in the nasal cannula which may cause NO2 formation that dilutes the NO concentration. Accordingly to reduce retrograde flow (e.g., that may result in NO2 formation that dilutes the NO doses and that can act as a known respiratory irritant, etc.), the volume of potential nitric oxide mixing with either exhaled gas and/or ambient gas may be minimized.

Noting the above, the amount of dilution resulting from retrograde flow can be dependent on the volume of the lumen associated with NO delivery (e.g., the NO lumen; combined NO and triggering lumen; combined NO, triggering, and O2/air lumen; etc.) at the cannula nosepiece (e.g., flow path) where retrograde flow may occur. The segment where retrograde flow may occur can have any shape. For ease, this segment where retrograde flow occurs is, at times, described as being "U" shaped, and the like. This is merely for ease and is in no way meant to be a limitation.

In exemplary embodiments, optimized ID dimensions (e.g., ID size, ID shape, etc.) of the lumen associated with NO delivery (e.g., the NO lumen; combined NO and triggering lumen; combined NO, triggering, and O2/air lumen; etc.) at the nosepiece (e.g., flow path) can be selected to reduce the volume of the "U" shaped region thereby minimizing the potential volumetric exchange associated with retrograde flow and/or dilution resulting from retrograde flow. Further, in exemplary embodiments, such optimal ID dimensions can vary depending on the volume of NO gas delivered. By way of example, a nitric oxide delivery device can deliver pulses of NO-containing gas with a minimum dose volume of 0.35 ml. In order to ensure volumetric dosing accuracy, it may be preferable that no more than a small percentage (e.g., 10%, 5%, 20%, etc.) of the dose can be lost due to retrograde flow.

One or more embodiments of the present invention limits the internal volume of this "U" shape to be no more than a small percentage (e.g., 10%, 5%, 20%, etc.) of the minimum dose volume (e.g., 0.035 ml for a 0.35 ml pulse of therapeutic gas) to ensure that if NO loss occurs it is an acceptable amount of NO loss due to retrograde flow (e.g., loss to ambient during the exhalation phase). Following the above example, for a 10% minimum dose volume of 0.035 ml, the lumen ID within the "U" segment may be no more than 0.046 inches given a prong length of 0.315 inches and a prong spacing of 0.63 inches. Therefore, a lumen ID significantly larger than 0.046 inches may not be advantageous to maintaining dose volume accuracy for minimum dose volumes of 0.35 ml.

It will be understood that the mathematics of this construct can be modified by variations in systems such as, but not limited to, systems with larger or smaller minimum dose volumes appropriately, systems with different prong lengths, and/or systems prong spacing, to name a few. One skilled in the art can perform the required calculations to determine the ID required to provide a desired volume in the "U" shaped segment so that it does not exceed 10% of the dose volume. Furthermore, depending on the required accuracy for the dosing, the internal "U" volume or other volume available for cross-flow can be, but is not limited to, less than 50%, 45%, 40%, 35%, 30%, 25%, 20%, 15%, 10%, 5%, 4%, 3%, 2% or 1% of the dose volume, to name a few.

For example, if the "U" shape consists of two nares and a backplane, the maximum dimensions such that the "U" volume does not exceed 20% of the minimum dose volume can be calculated using the following formula, wherein backplane refers to the length of the lumena inside the nosepiece and/or which forms the base of the "U" shape:

$$\text{Minimum Dose Volume} > 5[2\pi(\text{Prong Diameter}/2)^2 * (\text{Prong Length}) + \pi(\text{Backplane Diameter}/2)^2 * (\text{Backplane Length})]$$

Thus, if the minimum dose is known, the dimensions of the cannula "U" section can be calculated. For dosing accuracies other than 20%, the volume ratio factor of 5 can be changed accordingly with the volume ratio factor being equal to [100/(dose accuracy %)].

In exemplary embodiments, during exhalation and/or prior to inhalation (e.g., sensed and/or detected by the delivery device, etc.) the U-shaped volume in the nosepiece can be purged with a pulse of NO substantially equal to the U-volume. This can cause the U-volume to be substantially filled with NO (e.g., after exhalation). Further, this NO filling the U-volume can be delivered to the patient during the next inhalation, for example, ensuring early delivery of NO to the patient to provide optimal clinical efficacy (e.g., discussed below).

In exemplary embodiments, retrograde flow can be reduced by at least reducing the ID of the NO delivery lumen within the nasal prong (e.g., NO flow path) so that the resistance to flow through the NO lumen at the nasal prong can be increased. Noting this configuration, under the same pressure differential, the flow within the NO lumen of the nasal prongs can be reduced as compared to prongs with larger lumen. This can result in reduced cross flow under at least these conditions, for example, because the smaller ID NO lumen can produce gas flow resistance which can be inversely proportional to the fourth power of lumen's radius by Poiseuille's Law.

In exemplary embodiments, retrograde flow can be reduced by using valves and/or check valves, for example, as discussed below in greater detail.

At times, the NO lumen described herein may be described as being optimized for a minimum pulse volume of 0.35 ml and/or allowed 10% dosing error resulting in an allowable U-shaped volume in the NO lumen (e.g., of 0.035 ml). In exemplary embodiments, changes in this minimum pulse volume and/or the optimal pulse volume range may impact at least the NO lumen size. For example, should the minimum pulse volume be smaller due to, for example, higher nitric oxide concentrations being used, the inner diameter of the NO lumen and/or "U" volume may be decreased to ensure the 10% error goal. For example, the NO lumen and/or "U" volume may be decreased taking into account the various metrics for optimization such as, but not limited to, pulse shape. Further, for example, should the minimum pulse volume be increased due to, for example, the use of lower concentration nitric oxide, then the inner diameter of the NO lumen and/or "U" volume may be increased. For example, the NO lumen and/or "U" volume may be increased taking into account the various metrics for optimization such as, but not limited to, pulse shape. It will be understood that if the NO lumen and/or "U" volume is too large (e.g., about 0.1 ml to about 0.5 ml) then small volume pulses may not be able to be delivered accurately, delivery may be delayed, dilution may occur, and/or other problems may occur due to the unique nature of NO delivery.

Minimizing Delay and/or Distortion

For nitric oxide delivery systems (e.g., that may pulse nitric oxide gas to patients) to have optimal clinical efficacy it may be necessary to deliver a pulse or flow of nitric oxide to the patient as early in the inspiratory phase as possible and/or with a desired flow waveform (e.g., pulse shape). Noting this, pneumatic delays may be and/or should be minimized because, for example, pressure signals from the patient can be used as an indication of patient inspiratory effort and/or the beginning of patient inspiration. Also, distortion of pulse or flow waveforms may be and/or should be minimized because, for example, waveform shape and/or timing may be tied to clinical efficacy. Accordingly, one or more embodiments of the present invention relate to nasal cannula configurations that minimize the delay and/or distortion of pressure signals, for example, when in transit through the cannula from the patient back to the device and/or that minimize distortion of flow waveforms.

In exemplary embodiments, the lumen of the cannula affiliated with triggering (e.g., the triggering lumen; combined triggering and NO lumen; combined triggering, NO, and O2/air lumen; etc.) can be configured to minimize the delay and/or distortion of pressure signals when in transit through the cannula. To minimize the delay and/or distortion of pressure signals when in transit through the cannula, the cross-section of the lumen affiliated with triggering can be selected to reduce delay and/or distortion and/or the cross-sectional size can be increased and/or maximized to reduce delay and/or distortion.

In exemplary embodiments, the lumen of the cannula affiliated with NO delivery (e.g., NO lumen; combined NO and triggering lumen; combined NO, triggering, and O2/air lumen; etc.) can be configured to minimize distortion of flow waveforms. To minimize distortion of flow waveforms the cross-section of the lumen affiliated with NO delivery can be increased and/or maximized and/or the shape of the cross-section can be selected to reduce delay and/or distortion. Further, in exemplary embodiments, to minimize distortion of flow waveforms the lumen affiliated with NO delivery can be made having reduced compliance, i.e., having increased stiffness. For example, to minimize distortion of flow waveforms the lumen affiliated with NO delivery can be made of a substantially rigid material. The rigidity of the material can be selected for reducing compliance while still factoring in at least patient comfort.

Completing Metrics

In at least some embodiments the cannula can be configured such that one lumen can be for delivering NO and be for triggering (e.g., mono-lumen cannulas, dual-lumen cannulas, etc.). Such configurations can require optimizing the lumen for both NO delivery and for triggering to have minimal dilution of NO doses as well as allow the trigger signal to propagate to the device without attenuation substantially over the spectral band of human breathing (e.g., 0-4 Hz). This can be substantially difficult as these can be competing metrics for optimization. For example, in order to deliver a pulse and/or flow of NO early in the inspiratory phase, reduce pneumatic delays, reduce distortion of flow waveforms, reduce delay and/or distortion of pressure signals, reduce the volume of NO mixing and/or NO oxidation at the nosepiece, and/or address any other desired property (e.g., for a combined NO/triggering lumen) several competing metrics of the lumen ID can be optimized such as, but not limited to:

a. Reduce NO2 formation→Reduce lumen ID;
b. Maintain volumetric NO dosing accuracy→Reduce lumen ID;
c. Reduce NO flow distortion→Increase lumen ID; and
d. Minimize trigger signal attenuation or delay→Increase lumen ID.

In exemplary embodiments, cannulas of the present invention that have combined NO/triggering lumen configurations can require compromise of the optimal geometry (e.g., shape, size, etc.) of the NO/Trigger lumen to, for example, deliver pulses and/or flows of NO early in the inspiratory phase, reduce pneumatic delays, reduce distortion of flow waveforms, reduce delay and/or distortion of pressure signals, reduce the volume of NO mixing at the nosepiece, and/or NO oxidation at the nosepiece. Such compromise may be required for cannulas of the present invention that have combined NO/triggering lumen (e.g., mono-lumen cannulas, dual-lumen cannulas, etc.). However, cannulas configurations of the present invention that have at least three lumens (e.g., tri-lumen cannula, quad-lumen cannula, etc.), as discussed below, can allow for lumens dedicated to both NO delivery and to the trigger signal and can, in at least some instances, allow for a dedicated O2/air delivery lumen. As such, for cannulas of the present invention with dedicated lumens for NO delivery and triggering (e.g., tri lumen cannulas, quad-lumen cannulas, etc.) the optimized NO lumen can be smaller than the optimized trigger lumen since it may be beneficial to have a larger trigger lumen to ensure at least minimal signal attenuation while it may be beneficial to have a smaller NO lumen to reduce at least dilution of NO. As such, cannulas of the present invention having combined NO/triggering lumens (e.g., mono-lumen, dual-lumen cannulas, etc.) and cannulas of the present invention having dedicated NO delivery lumens and dedicated triggering lumens (e.g., tri-lumen cannulas, quad-lumen cannulas etc.) can have different geometries when optimized.

By way of example, in addition to ensuring the accuracy of volumetric dosing (e.g., described above with respect to minimizing dilution resulting from retrograde flow), the ID of combined NO/triggering lumens can be designed to reduce and/or not produce gas flow distortion and/or undue signal propagation delay, for example, from the patient to the device (e.g., described above with respect to minimizing delay and/or distortion of pressure signals). Such distortion and/or delay may occur as pneumatic tubes may behave as first order pneumatic low pass filters and attenuate higher frequency signal components. Modification of the inner diameters can change the band pass characteristics of the filtering effect. However, as noted earlier, the inner diameter (e.g., at the U) can be fixed to a certain maximum ID based on the required dose delivery accuracy of the system.

In light of at least the above, in exemplary embodiments, to minimize the effects of the potentially frequency attenuated pressure signal: (1) the upstream (close to device) diameter of the combined NO/triggering lumen of cannulas of the present invention can be adjusted to widen (e.g., optimize) the band pass characteristics of the cannula and/or (2) triggering of the initiation of pulse delivery of NO (e.g., by the delivery device) may have the typical threshold pressure trigger strategy (e.g., the pressure signal may be attenuated and/or delayed by the pneumatic filtering effect of the cannula construct) and therefore it may be advantageous to supplement/replace this threshold pressure trigger with a pressure slope based triggering strategy based on a pattern of sloping pressure indicative of patient effort. Such a pressure slope based triggering strategy in the presence of significant signal attenuation can be more responsive (e.g., faster) to patient effort. It will be understood that to minimize the effects of the potentially attenuated/delayed pressure signal the downstream diameter of the combined NO/triggering lumen of cannulas of the present invention can be adjusted to widen (e.g., optimize) the band pass characteristics of the cannula; however, this may produce an undesirable side effect of the cannula nosepiece size being increased, which in turn may make the cannula less comfortable to the patient.

In exemplary embodiments, the upstream diameter of the combined NO/triggering lumen can be adjusted to widen the band pass characteristics of the cannula to ensure that unneeded compressible volume may be unavailable upstream of the nose piece restriction (e.g., 0.046 inch ID restriction, etc.). This can reduce the compressible volume in the cannula and/or effectively increases the band pass characteristics of the cannula.

In exemplary embodiments, triggering of dose delivery (e.g., by the delivery device) can be based on a pattern of sloping pressure indicative of patient efforts and/or the slope can be reduced in magnitude by the filtering characteristics of the tubing, however, the slope can still be present for algorithmic triggering decisions (e.g., by the delivery device). In exemplary embodiments, triggering methodologies can be based not on pressure thresholds, rather triggering methodologies can be based on pressure slope trends that can also be employed to improve overall timely delivery of dosing to the patient. It will be understood that such a triggering implementation can be optional.

Mono-Lumen Cannula

Figure 3A:
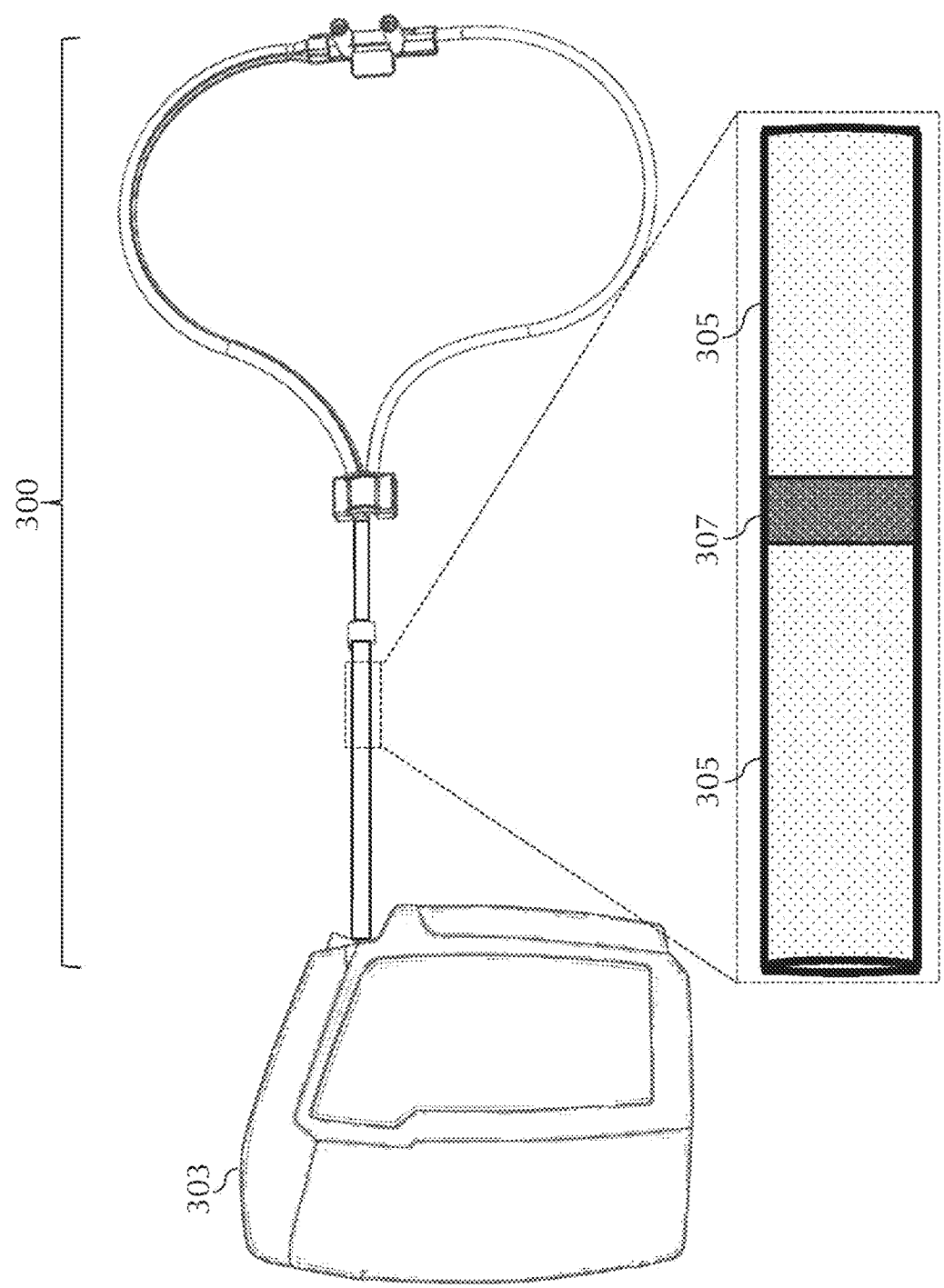

Referring to FIG. 3A, in exemplary embodiments, the nasal cannula can have at least one lumen (i.e. a mono-lumen cannula 300) that can deliver nitric oxide in the same lumen as used to deliver oxygen and/or trigger a delivery device 303. Using mono-lumen cannula 300, in a single lumen, oxygen and/or ambient air flow 305 can be delivered to a patient with doses of NO 307 intermittently pulsed into the flow. This same lumen may also be used for triggering. Using this technique, retrograde flow can be substantially reduced, for example, because the O2 and/or air can effectively clear the cannula nosepiece after each NO pulse and or because the single lumen can be a closed system at the device upon valve closure and thus flow into the cannula lumen can be prevented. However, using this technique, oxygen and/or air 305 can be in contact with NO 307 within the lumen of cannula 300 and react (e.g., forming NO2) thereby diluting the intended NO dose.

In exemplary embodiments, a carrier gas can be used buffer (e.g., insulate) the NO from O2 and/or a carrier gas can be used to increase the effective volume of the delivered dose, for example, to reduce the transit time of NO in the cannula. This buffer gas can be diffused into the NO dose and/or surround the NO dose (e.g., spatially before and after).

Referring to FIG. 3B, in exemplary embodiments, to reduce dilution of NO 307 with oxygen and/or air 305 within the NO/O2 lumen, a buffer agent 309 can be delivered between NO 307 and oxygen 305. By way of example, first oxygen can be delivered through the NO/O2 lumen, then a buffer agent (e.g., an inert gas, nitrogen gas, etc.) can be delivered, then NO can be delivered, then another buffer agent can be delivered, and then oxygen can be delivered. The buffer agent can reduce interaction between NO and oxygen thereby reducing dilution of NO, for example, caused by NO2 formation.

In exemplary embodiments, when using a buffer gas to transport the NO within the cannula the amount of contact between NO with O2 and the time of contact can be minimized without substantially distorting the shape of the NO pulse dose. In exemplary embodiments, the buffer gas can be substantially devoid of O2 such that it can act as a buffer to any entrained O2 and/or it can increase the volume of delivered gas thereby decreasing the time that the NO dose in the cannula. In exemplary embodiments, the buffer gas can include oxygen, however, the diameter of the cannula lumen can be small enough so that the cross section of the NO dose exposed to O2 can be minimized and/or the diameter can be large enough to ensure that the pulse shape of the dose may not be substantially distorted.

In exemplary embodiments, a buffer gas can be provided by using the O2 depleted gas mixture remaining after an oxygen concentrator system has removed the O2 from air.

It will be understood that the buffer disclosed can be used with any multi-lumen cannula (e.g., dual-lumen cannula, tri-lumen cannula, quad-lumen cannula, etc.) where NO and O2 may be delivered in the same lumen. For example, a dual lumen cannula can have a trigger lumen and combined NO/O2 lumen wherein NO may be intermittently pulsed into O2 with a buffer separating the NO and O2.

In exemplary embodiments, the inner diameter of the mono-lumen (e.g., combined NO/O2 lumen, combined NO/O2/Trigger lumen, etc.) can be configured to be substantially small, for example, to reduce residual gas mixing. As discussed above, lumens that include different functions (e.g., NO delivery, triggering, O2 delivery, etc.) can have competing metrics for optimization. For optimization, the dimensions of the cross-section of the mono-lumen can require a compromise between at least some of these competing metrics. For example, because the mono-lumen has a combined NO/triggering lumen and/or combined NO/O2/Trigger, the optimal geometry (e.g., shape, size, etc.) of the mono-lumen can require compromise between at least some competing metrics to, for example, deliver pulses and/or flows of NO early in the inspiratory phase, reduce pneumatic delays, reduce distortion of flow waveforms, reduce delay and/or distortion of pressure signals, reduce the volume of NO mixing at the nosepiece, and/or NO oxidation at the nosepiece. Considering at least the competing metrics for optimization, in at least some embodiments, the inner diameter of the mono-lumen (e.g., combined NO/O2 lumen, combined NO/O2/Trigger lumen, etc.) can be less than about 0.07 inches.

Dual-Lumen Cannula

Figure 4:
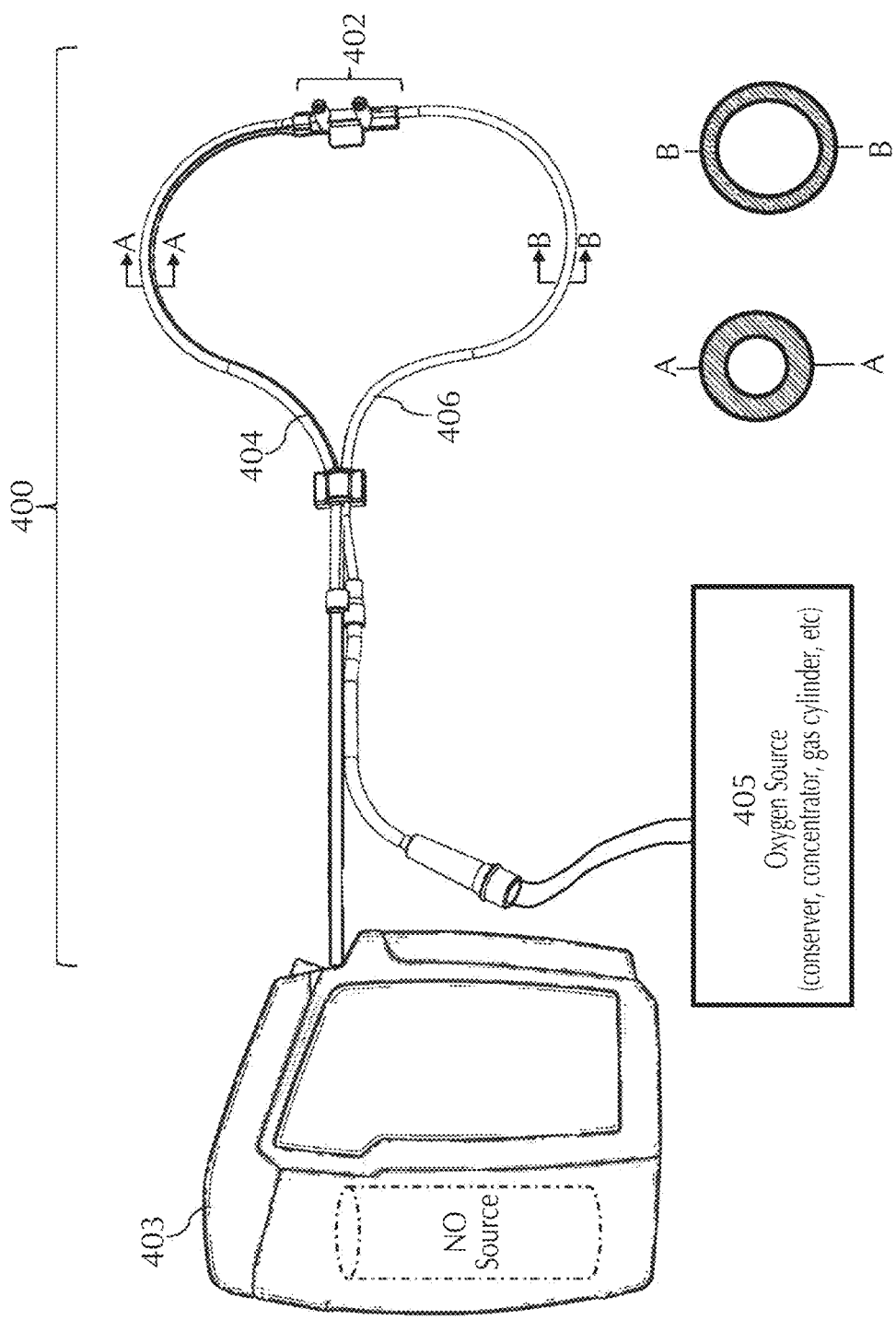

Referring to FIG. 4, in exemplary embodiments, the nasal cannula can have at least two lumens (i.e. a dual-lumen cannula 400) that can deliver nitric oxide in a separate lumen (e.g., NO lumen 404) than the at least one lumen 406 that can deliver oxygen (e.g., from oxygen/air supply 405) and/or that can trigger the delivery device (e.g., delivery device 403). The NO lumen can carry therapeutic gas comprising NO from NO delivery device 403 to the patient (e.g., at cannula nosepiece 402). The two lumens can be aggregated into a single cannula nosepiece (e.g., cannula nosepiece 402) that can have separate flow paths for each lumen.

In exemplary embodiments, the lumen (e.g., of the dual-lumen cannula) that carries the nitric-oxide containing gas can have a substantially small inner diameter that may be smaller than the other lumen(s) (e.g., the triggering lumen, oxygen lumen, etc.). In at least these embodiments, having a substantially small inner diameter for the lumen that carries NO the cannula can reduce dilution by at least the following mechanisms: (i) minimizing mixing of oxygen and NO because of a reduction in retrograde flow into the small ID NO carrying lumen due to the smaller ID; (ii) minimizing the bulk volume of gas mixing because the volume of NO gas per unit length can be reduced by having a small ID NO caring lumen; and/or (iii) the small ID NO carrying lumen can produce a narrow jet of gas flow which can effectively minimize O2/NO mixing during NO delivery and/or can minimize O2/NO mixing during NO delivery until much further into the nasal cavity. Similar mechanisms for reducing dilution can be accomplished by reducing the ID of the lumen for NO delivery used in other multi-lumen cannulas described herein (e.g., tri-lumen cannulas, quad-lumen cannulas, etc.).

In exemplary embodiments, the diameter of the small lumen can be minimized such that it can be as small as reasonably possible without producing confounding upstream effects on the flow delivery mechanics of the device. For example, in one or more embodiments, the NO lumen may have an ID in the range from about 0.01 inches to about 0.10 inches and/or about 0.03 inches to about 0.08 inches. Further, in one or more embodiments, the oxygen lumen and/or trigger lumen (e.g., dedicated trigger lumen, etc.) may have an ID in the range from about 0.05 inches to about 0.20 inches and/or about 0.08 inches.

Referring to FIGS. 5A-5B, in exemplary embodiments, a dual-lumen cannula can have a first lumen 502 for oxygen delivery and a second lumen 504 for delivery of NO and transmitting the pressure signal for the trigger sensor of delivery device 505. In this configuration, first lumen 502 can carry oxygen from an oxygen conserver/concentrator 507 to the nosepiece 506 of the cannula. Second lumen 504 can deliver NO from the nitric oxide delivery device to the patient and/or can deliver the pressure-based triggering signal from the patient to trigger sensor of the nitric oxide delivery device. Both lumens can be constructed to connect (e.g., tee) to both nares 508/510 and thus be in unobstructed fluid communication with both nares 508/510.

The first lumen for carrying oxygen can be constructed with a lumen inner diameter geometry consistent with industry norms. For example, a nasal cannulas with rated 6 LPM oxygen delivery capacity can have an oxygen lumen inner diameter of approximately 0.08 inches at, or near, the nosepiece. Accordingly, in one or more embodiments, the oxygen lumen can have an inner diameter in the range of about 0.05 inches to about 0.20 inches and/or about 0.08 inches.

The second lumen for carrying NO and triggering can be constructed based on compromise of competing metrics (e.g., as discussed above). For example, because the second lumen combines carrying NO and triggering, the optimal geometry (e.g., shape, size, etc.) of the second lumen can require compromise between at least some competing metrics to, for example, deliver pulses and/or flows of NO early in the inspiratory phase, reduce pneumatic delays, reduce distortion of flow waveforms, reduce delay and/or distortion of pressure signals, reduce the volume of NO mixing at the nosepiece, and/or NO oxidation at the nosepiece. Considering at least the competing metrics for optimization, in at least some embodiments, the geometry of the combined NO/Trigger lumen of the dual-lumen cannula can be in the range of about 0.08 inches. In exemplary embodiments, the internal diameter of the second lumen can be dictated by volumetric dosing accuracy considerations, the second lumen can have an ID in the range of about 0.01 inches to about 0.10 inches, and/or the second lumen can have an ID in the range of about 0.01 inches to about 0.06 inches with upstream tubing that can be adjusted to optimize (e.g., widened, etc.) the band pass performance of the system.

In exemplary embodiments, a dual-lumen cannula can have a first lumen for NO delivery and a second lumen for delivery of O2 and transmitting the pressure signal for the trigger sensor of delivery device. In this configuration the NO lumen can be substantially small (e.g., having similar dimensions to the NO lumen described below in a tri-lumen cannula) and/or the combined O2 and triggering lumen can have an inner diameter in the range of about 0.07 inches to about 0.14 inches and/or about 0.03 inches to about 0.08 inches at the nosepiece. In exemplary embodiments, a dual-lumen cannula can have a first lumen for NO and O2 delivery and a second lumen for transmitting the pressure signal for the trigger sensor of delivery device. In this configuration, the first lumen for NO and O2 delivery can utilize similar techniques for delivering NO and O2 in the same lumen, for example, as described herein with reference to a mono-lumen cannula.

Tri-Lumen Cannula

Figure 6A:
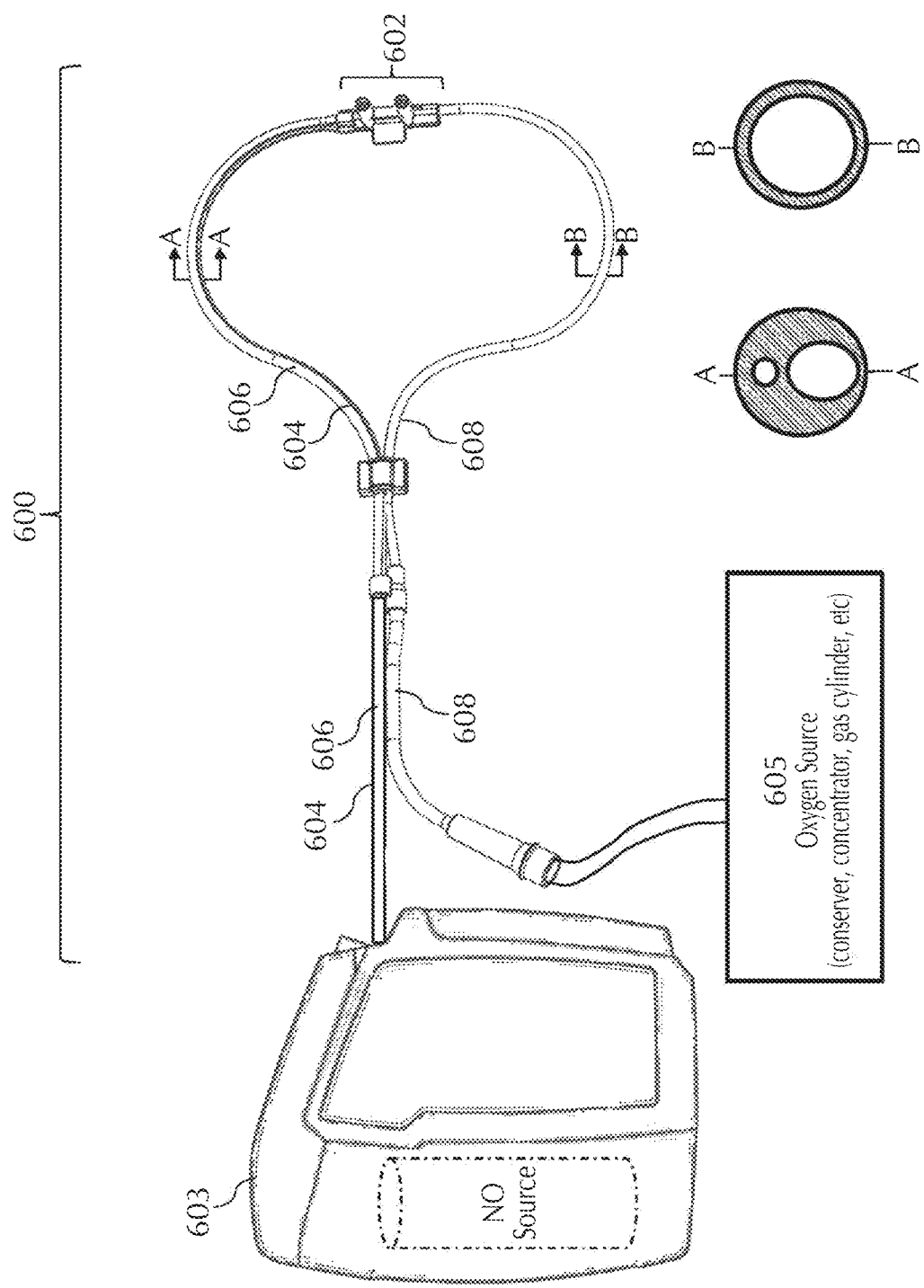
FIGS. 6A and 6B show exemplary pneumatic paths for the NO, oxygen, and trigger lumens in a tri-lumen cannula, in accordance with exemplary embodiments of the present invention.
Figure 6C:
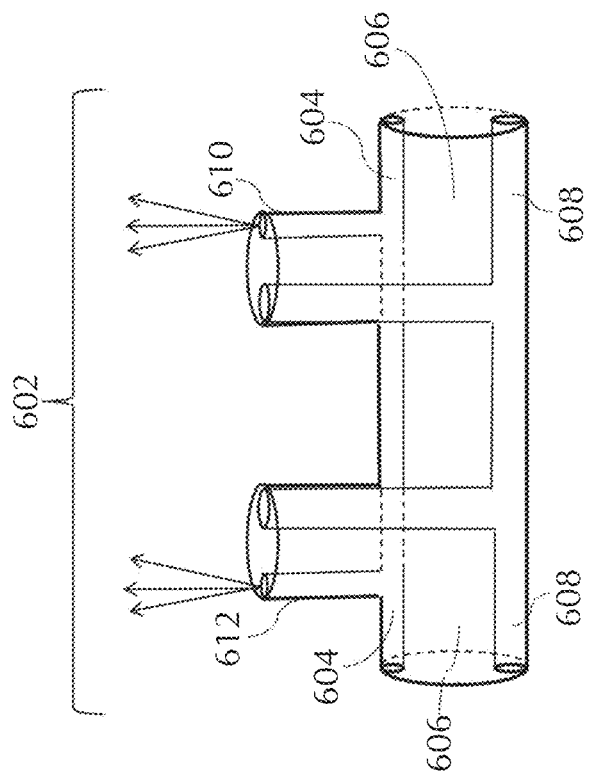
Figure 6B:
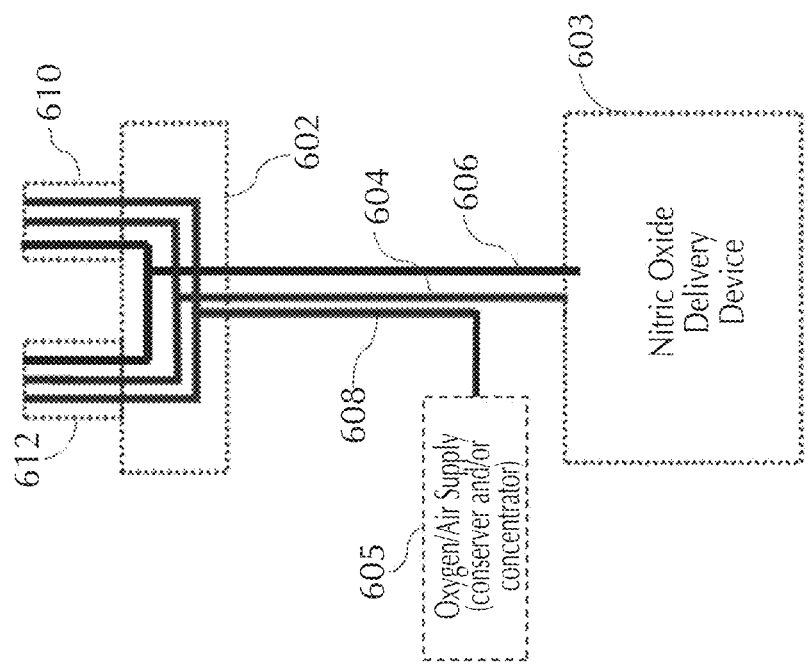
Figure 8A:
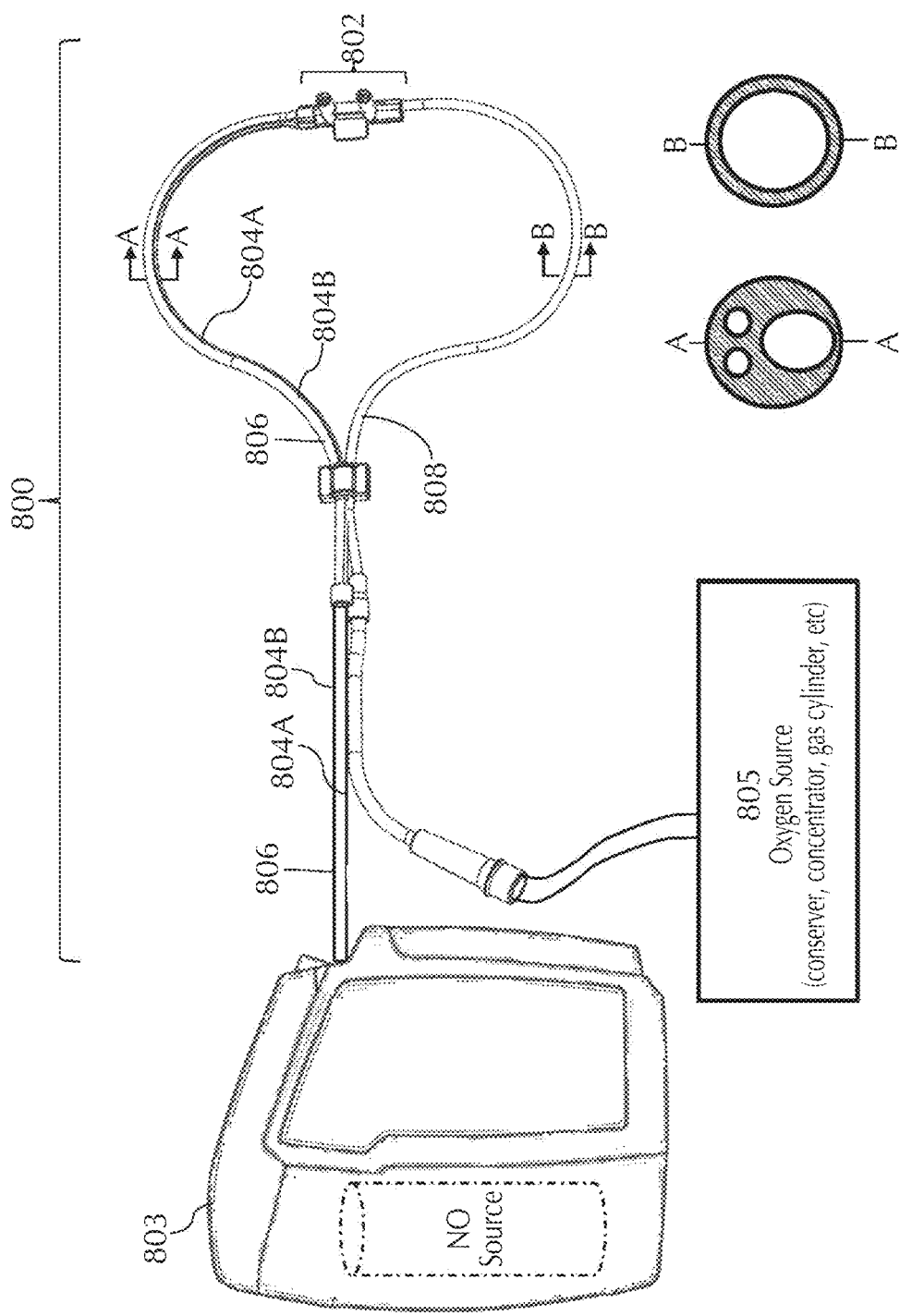
FIGS. 8A and 8B show exemplary pneumatic paths for the NO, oxygen and trigger lumens in a quad-lumen cannula, in accordance with exemplary embodiments of the present invention.
Figure 8C:
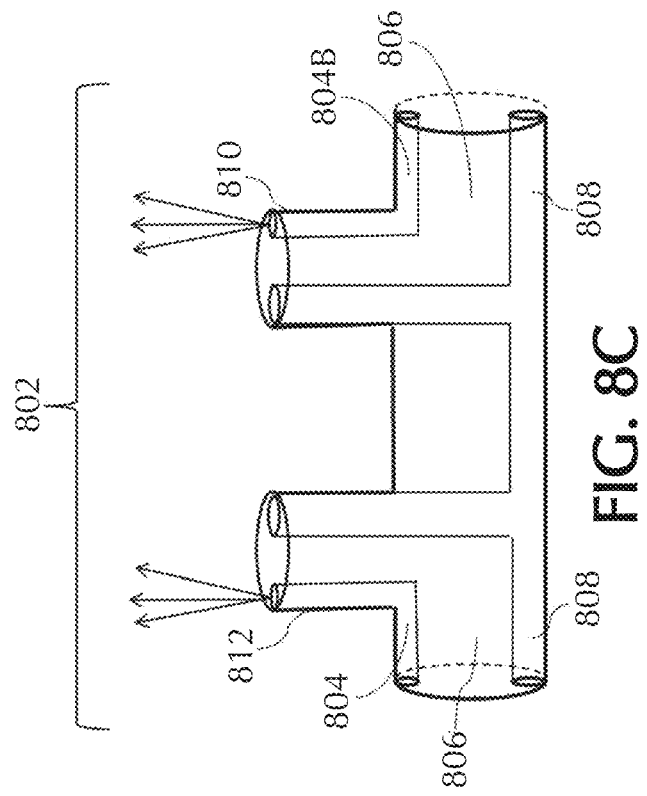
Figure 8B:
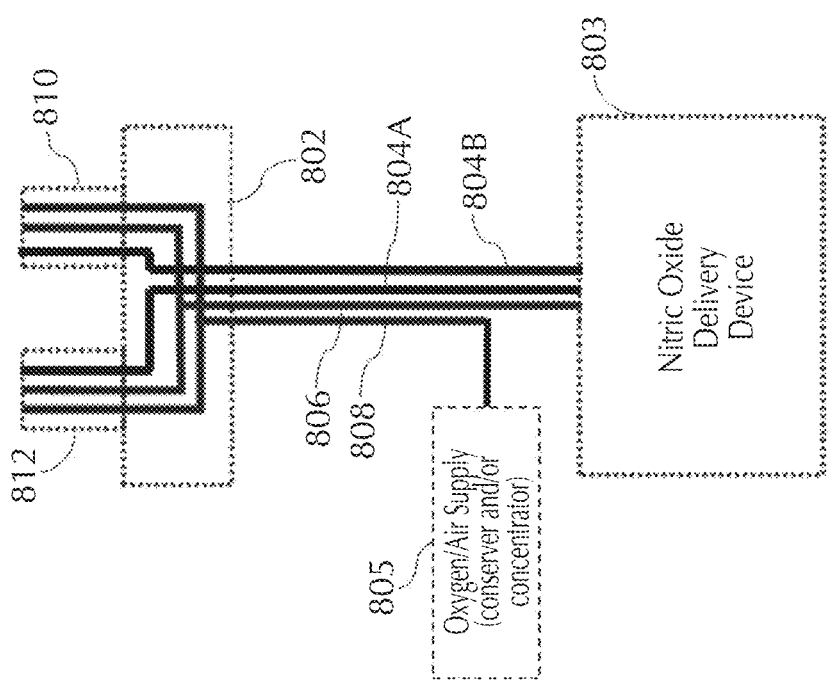

Referring to FIGS. 6A-7, in exemplary embodiments, the nasal cannula can have at least three lumens (i.e. a tri-lumen cannula 600): one lumen that can deliver nitric oxide in a lumen (e.g., NO lumen 604), for example, from a delivery device (e.g., delivery device 603); another lumen that can be for triggering (e.g., triggering lumen 606), for example, the delivery device (e.g., delivery device 603); and another lumen that can deliver O2 in a lumen (e.g., O2 lumen 608), for example, from an O2/air source (e.g., conserver and/or concentrator 605). The three lumens can be aggregated into a single cannula nosepiece (e.g., cannula nosepiece 602) that can have separate flow paths for each lumen and/or at least one lumen.

The NO lumen can be a dedicated lumen that can carry therapeutic gas comprising NO from NO delivery device 603 to the patient (e.g., via nares 610/612 at cannula nosepiece 602). The oxygen lumen can be a dedicated lumen that can carry an oxygen-enriched gas (e.g., such as oxygen-enriched air, substantially pure oxygen, etc.) from an oxygen source to the patient (e.g., via nares 610/612 at cannula nosepiece 602). The oxygen source can be an oxygen pulsing device (e.g., such as an oxygen conserver) and/or a constant flow oxygen device (e.g., such as an oxygen concentrator) and/or can be a port on the NO delivery device that delivers the oxygen-enriched gas. The trigger lumen can be a dedicated lumen that allows propagation of triggering signals from the patient to NO delivery device 603.

In exemplary embodiments, the nasal cannula can connect the oxygen lumen to an oxygen source (e.g., an oxygen pulsing device, an oxygen conserver, a constant flow oxygen device, oxygen concentrator, etc.) and/or the nasal cannula may not connect the oxygen lumen to an oxygen source (e.g., for patients who are not receiving supplemental oxygen). For patients who are not receiving supplemental oxygen, the oxygen lumen may be removed and/or may be partially removed. For example, the oxygen lumen may be partially preserved to support the oxygen side of the cannula which goes around the patient's head while the lumen portion providing the connection to an oxygen source (e.g., an oxygen pigtail off of the reducer) may be removed. Removal and/or partial removal of the oxygen lumen can similarly be done for other multi-lumen cannulas described herein (e.g., dual-lumen cannulas, quad-lumen cannulas, etc.).

Referring to FIGS. 6C and 7, an exemplary cannula can include three lumens at the nosepiece (e.g., nose bridge fitting, etc.) and/or the pneumatic paths and/or lumina can be separated by partitions and/or diaphragms that may be within the nosepiece and/or nares of the cannula. The NO supply can traverse the nosepiece through a lower gas resistance source to higher resistance orifices that can be included into the nares of the cannula. In exemplary embodiments, each lumen may be separated by a diaphragm partition within the nosepiece of the cannula and/or within the nares of the cannula to prevent mixing of the fluid streams in the separate lumens.

The three lumens can be extruded through a single die producing a multi-lumen tube, can be extruded in a single multicavity extrusion, can be extruded separately and affixed together in a paratube arrangement disclosed herein, and/or using any other reasonable technique. Similar techniques can be used for other multi-lumen cannulas described herein (e.g., dual-lumen cannulas, quad-lumen cannulas, etc.).

Referring to FIG. 7, in exemplary embodiments, the NO delivery lumen/tube 604 can decrease in inner diameter (ID) at least once when just about to, and/or just after, entering the nasal cannula nosepiece 602. Accordingly, in one or more embodiments, the pneumatic resistance may be greater in the nares of the nasal cannula than in the tubing carrying the NO from the NO delivery device to the cannula nosepiece. In exemplary embodiments, the smaller ID tubing of the dedicated NO delivery lumen can allow for advantages such as, but not limited to:

Short gas transit times;
Reduced inspiratory/expiratory phase retrograde flow of ambient air into the lumen (e.g., reduced according to Knudsen diffusion which states that diffusion rate is proportionate to the mean free path length of the gas molecule which can be reduced with smaller ID);
Increased gas resistance to flow (e.g., smaller ID tubing produces gas flow resistance which can be inversely proportional to the fourth power of tubing radius by Poiseuille's Law); and
Reduced volume in the tee'd loop of the NO delivery lumen.

The above can reduce the potential for retrograde flow, reduce the volume of retrograde flow, and/or reduce the contact and/or contact duration between NO and other gasses including oxygen in the cannula, to name a few. This in turn can reduce the dilution of NO and/or thereby increase the precision of the delivered NO dose. Accordingly, in exemplary embodiments, the ID of the NO lumen can be about 0.01 inches to about 0.10 inches and/or about 0.07 inches.

The ID of the NO lumen can decrease from a maximum ID to a minimum ID, for example, to at least reduce cross flow and/or increase patient comfort. In exemplary embodiments, the ratio of the minimum ID to the maximum ID of the NO lumen can be, but is not limited to, 1:1, 1:1.2, 1:1.3, 1:1.5, 1:2, 1:2.5, 1:3, 1:3.5, 1:4, 1:4.5, 1:5, 1:5.5, 1:6, 1:7, 1:8, 1:9, and/or 1:10, to name a few. Similar ratios of the minimum ID to the maximum ID of the NO lumen can be used for other multi-lumen cannulas (e.g., dual-lumen, tri-lumen, quad-lumen cannula, etc.) described herein that can have dedicated lumens for NO delivery and/or combined NO delivery and triggering lumens.

The trigger lumen ID can be comparatively much larger than the NO lumen ID. The trigger lumen ID can be substantially larger so that trigger pressure drop on inhalation can be transmitted through this cannula lumen with the smallest possible loss of signal magnitude and/or phase delay to the NO delivery device which in turn can use this pressure signal to deliver pulsed NO. Accordingly, in exemplary embodiments, the ID of the trigger lumen can be about 0.05 inches to about 0.20 inches and/or about 0.08 inches. In exemplary embodiments, the ratio of the ID of the NO lumen to the ID of trigger lumen can be, but is not limited to, 1:1, 1:1.2, 1:1.3, 1:1.5, 1:2, 1:2.5, 1:3, 1:3.5, 1:4, 1:4.5, 1:5, 1:5.5, 1:6, 1:7, 1:8, 1:9, 1:10, 1:12, 1:15, 1:20, 1:25, and/or 1:30, to name a few.

The oxygen lumen can also be larger than the NO lumen, for example, to minimize oxygen flow resistance and/or to reduce gas flow speed at the nares which can serve to interfere with the triggering pressure signal due to gas flow effects (e.g., such as from Bernoulli's principle) and/or to reduce high frequency (e.g., auditory range) resonance with high speed oxygen transit to reduce the "noise" associated with oxygen delivery. Accordingly, in exemplary embodiments, the ID of the oxygen lumen can be about 0.05 inches to about 0.20 inches and/or about 0.08 inches. In exemplary embodiments, the ratio of the ID of the NO lumen to the ID of the oxygen lumen can be, but is not limited to, 1:1, 1:1.2, 1:1.3, 1:1.5, 1:2, 1:2.5, 1:3, 1:3.5, 1:4, 1:4.5, 1:5, 1:5.5, 1:6, 1:7, 1:8, 1:9, 1:10, 1:12, 1:15, 1:20, 1:25, and/or 1:30, to name a few.

Quad-Lumen Cannula

Referring to FIGS. 8A-8D, in exemplary embodiments, the nasal cannula can have at least four lumens (i.e. a quad-lumen cannula 800): two lumens that can deliver nitric oxide in a lumen (e.g., NO lumen 804A and 804B), for example, from a delivery device (e.g., delivery device 803); another lumen that can be for triggering (e.g., triggering lumen 806), for example, the delivery device (e.g., delivery device 803); and another lumen that can deliver O2 in a lumen (e.g., O2 lumen 808), for example, from an O2/air source (e.g., conserver and/or concentrator 805). The four lumens can be aggregated into a single cannula nosepiece (e.g., cannula nosepiece 802) that can have separate flow paths for each lumen and/or at least one lumen.

In exemplary embodiments, like the pneumatic configurations discussed above, this configuration can separate the pneumatic paths of the NO, oxygen, and trigger. Further, in exemplary embodiments, the NO flow delivery paths to each nostril can be kept separate and distinct and/or have their own pneumatic delivery source at the NO delivery device.

Referring to FIG. 8D, an exemplary quad-lumen cannula having the above configuration can be constructed at the cannula nosepiece wherein the quad-lumen cannula can fuse the lumen of the cannula into a single umbilical between the cannula nosepiece and the device, for example, as may be similarly done with the tri-lumen cannula. Similar to the tri-lumen cannula (e.g., as described referring to at least FIG. 7), NO delivery lumen/tube 804A and 804B can decrease in inner diameter (ID) at least once when just about to, and/or just after, the tubing enters the nasal cannula nosepiece 802. Accordingly, in one or more embodiments, the pneumatic resistance may be greater in the nares of the nasal cannula than in the tubing carrying the NO from the NO delivery device to the cannula nosepiece.

In exemplary embodiments, the dimensions of the triggering lumen 806, oxygen lumen 808, NO lumens 804A and 804B can be similar to the respective lumens in the tri-lumen cannula and/or the geometry of these lumens can provide similar benefits as those described above with respect to the tri-lumen cannula.

Further to the above benefits, the quad-lumen cannula configuration can, amongst other things, prevent movement of gas through the connected (e.g., tee'd) delivery loop of the NO supply line during exhalation. This can reduce NO/oxygen contact and/or reduce or substantially eliminate cross flow. In at least some instances, use of the quad-lumen cannula can require dedicated pneumatic circuitry for each NO lumen.

In exemplary embodiments, the quad lumen cannula configuration can include two triggering lumens (e.g., one two each nostril) as well as an NO delivery lumen and an O2 delivery lumen. Of course other configurations are within the scope of the invention.

Check Valves and Valves

In one or more embodiments, a nasal cannula (e.g., single lumen cannula, multi-lumen cannula, any of the nasal cannulas disclosed herein, etc.) can include one or more check valves that can be located in, and/or in fluid communication with, the nitric oxide delivery line. Further, in exemplary embodiments, one or more check valves located in, and/or in fluid communication with, the nitric oxide delivery line can be combined with any of the multi-lumen configurations described. Check valves can be used to, amongst other things, prevent retrograde gas movement into the NO supply lumen during inhalation/exhalation. Check valves can be any low cracking pressure check valve which can be placed at some point in, and/or in fluid communication with, the NO delivery path. Such check valves can include, but are not limited to, duckbill valves, umbrella valves, and/or any other valve.

Referring to FIG. 9A, exemplary duck bill valve 902 and/or referring to FIGS. 9B-9C exemplary umbrella valves 904 are illustratively depicted that can be used in accordance with nasal cannulas of the present invention. These check valves can be miniature check valves, for example, so they can have the dimensions to fit in the NO delivery lumen and/or be in fluid communication with the NO delivery lumen and/or they may be constructed out of the lumen itself by appropriately shaping and/or slitting the lumen outlet during the molding and/or manufacturing process.

Figure 10:
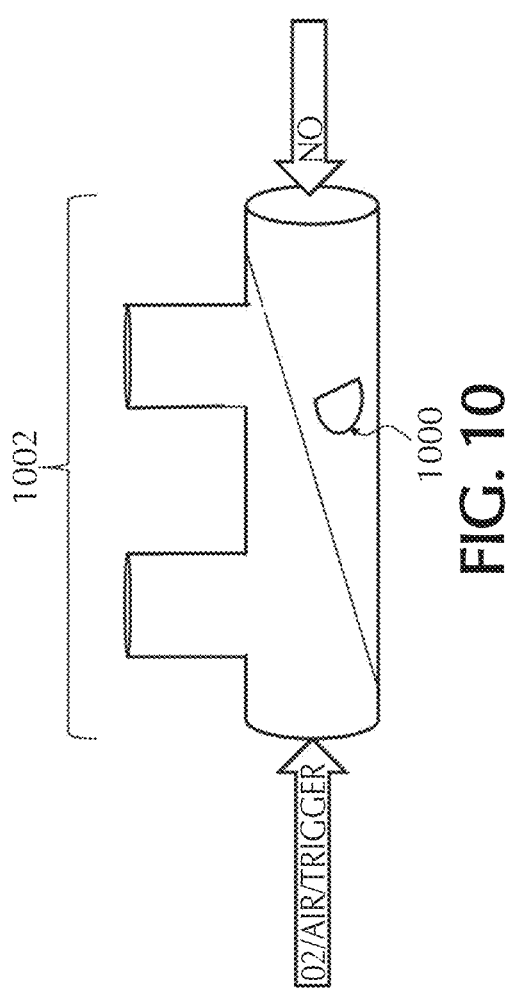
FIG. 10 shows an exemplary nasal cannula with an umbrella or flapper valve for delivering NO, in accordance with exemplary embodiments of the present invention.

Referring to FIG. 10, in one or more embodiments, the NO delivery cannula and/or lumen can have a small flapper and/or umbrella check valve 1000 that can be located at the cannula nosepiece 1002 and/or that can allow pulses of NO to be delivered to the general nose/mouth area during device NO pulsing. This configuration can allow NO to flow into either and/or both open nares upon inhalation and/or can restrict retrograde flow into the NO lumen (e.g., during exhalation). The O2 and/or trigger lumen can be combined or kept separate from the NO lumen, for example, to reduce any adverse signal-to-noise ratio impact on the performance of the trigger lumen due to oxygen flow. Such a configuration with the flapper valve can prevent retrograde flow of oxygen into the NO delivery path thereby reducing the potential for dilution of the dose. A diaphragm and/or other barrier can separate the NO delivery line from the O2/trigger line at the cannula nosepiece, for example, to prevent mixing.

In one or more embodiments, the nasal cannula can incorporate an impermeable and/or semi-permeable membrane that can be movable or fixed and/or can be actively or passively moved when needed. Further, the membrane can separate the NO containing gas or material from the O2 containing gas or material, for example, until the NO needs to be delivered to the patient. This membrane can reduce the contact time, surface area, and/or diffusion rate between the NO and O2 containing gases. This can reduce the formation of NO2, which can dilute the intended NO delivery concentration.

Figure 11B:
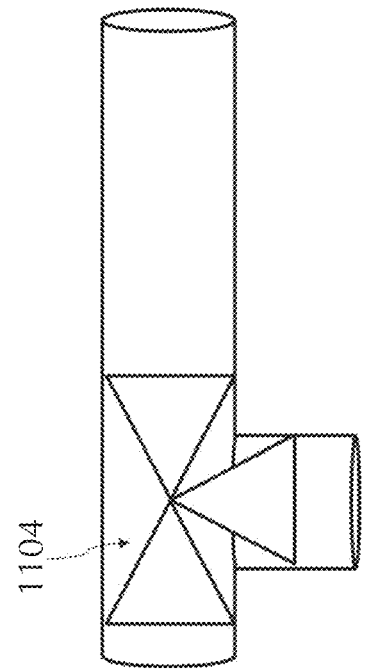
FIGS. 11A and 11B show exemplary valves incorporated into the NO delivery line, in accordance with exemplary embodiments of the present invention.
Figure 11A:
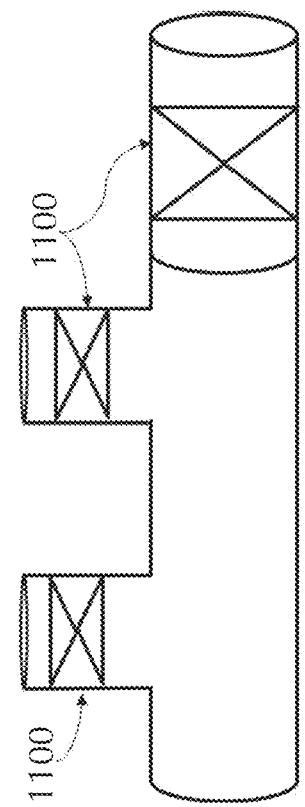

Referring to FIG. 11A, in one or more embodiments of the invention, a normally-closed valve 1100 (e.g., a duck bill valve, flap valve, pressure valve, etc.) at the substantially at, and/or near, the end of the NO containing cannula, NO lumen, and/or nosepiece of the cannula can prevent air from contacting the NO containing gas inside the cannula, for example, until the valve opening may be triggered (e.g. by a drop in pressure caused by inhalation by the patient or by the positive pressure caused by the delivery device as it attempts to deliver the NO containing gas to the patient). When the valve opening is triggered, the NO can then be delivered to the patient.

In one or more embodiments, a system can be used and/or provided to expel the gas or other NO containing material that come in contact with O2 containing gas or material, which can have otherwise formed NO2 in this mixture. The system can subsequently allow another part of the NO containing gas or material that has minimal or no NO2 to be delivered to the patient.

Referring to FIG. 11B, in one or more embodiments of the invention, the system and/or nasal cannulas can include and/or be in fluid communication with an electromechanical valve system 1104 that can actuate, for example, to pump out a fixed or adjustable amount of gas mixture that might contain NO2 through a separate orifice than the cannula opening to the patient. The system can then actuate to pump the NO containing gas or material to the patient.

It will be understood that the any of above teachings (e.g., check valves, check valve configurations, membranes, valves, electromechanical valve systems, etc.) can be combined with any of the other pneumatic configurations, cannula configurations, and/or teachings and/or embodiments described herein. For example, the above teachings (e.g., check valve configurations, etc.) can be used with the mono-lumen cannulas or multi-lumen cannulas described herein and/or any other teachings and/or embodiments described herein.

Minimizing NO/O2 Contact During Connection to Source

One or more embodiments of the present invention relate to nasal cannulas and/or systems that reduce NO/O2 contact during the connection of the high pressure source (e.g., a pressurized cylinder, etc.) to the delivery device (e.g., one or more of the above sources of oxygen/NO contact) and thereby dilution of the intended NO dose using a three way valve. For example, nasal cannulas and/or systems of the present invention can include a three way valve with one port to ambient that can be configured so that the three way valve opens to ambient upon connection of the canister to remove (e.g., blow off) the oxygen.

Proportional Nostril Delivery

Figure 13:
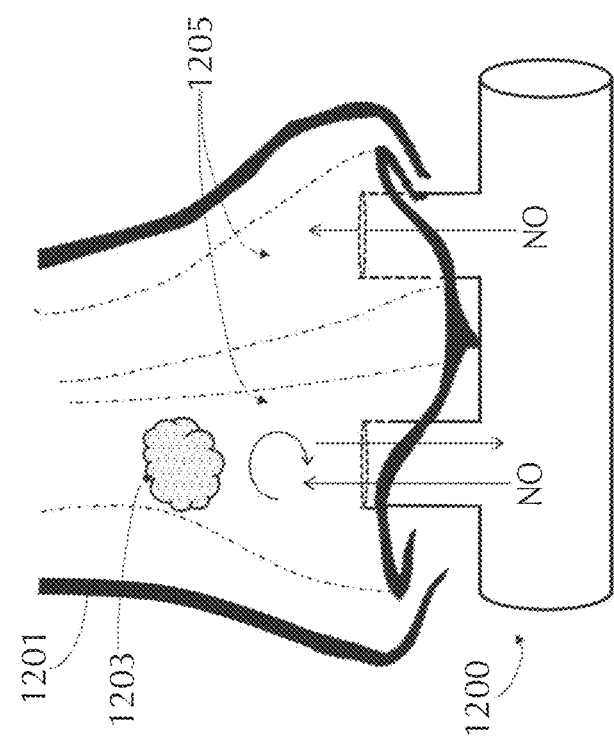
FIG. 13 shows injection of NO into a flow of ambient air into each nostril, in accordance with exemplary embodiments of the present invention.

Referring to FIGS. 12-13, one or more embodiments of the present invention relate to nasal cannulas and/or systems that address the problem of drug loss (e.g., to the ambient environment) when delivering a gaseous drug (e.g., in the form of pulsed nitric oxide, etc.) through a nasal cannula due to at least a partially occluded nasal passage (e.g., as shown in FIG. 12). By way of example of such a problem, if one side of the nose (e.g., nose 1201) is occluded (e.g., occlusion 1203) and the drug is being delivered to both sides of the nose through a cannula/delivery system 1200 which does not discriminate how much of the drug goes to either nostril (e.g., nostrils 1205), then there can be drug loss due to the occluded nostril. In addition, there may be other undesired consequences such as the reaction of the unused therapy gas with other materials and/or compounds that may come in contact with the gas.

This inadequate dosing can be a particular problem when delivering the drug therapy in set limited quantities, such as when pulsed (e.g., when delivered synchronous to a patient's breathing pattern and rhythm) through a single lumen exiting the delivery device that in turn may then be split at some point downstream before reaching the patient. Further, this can be a particular problem because, when pulsing the drug dose through a single lumen that is then split, the dose can be equally or substantially equally split in the two streams without consideration for the blockage in the nose downstream of the split. Thus a significant part (e.g., up to half) of the dose may not be delivered to the patient and/or may remain in the vicinity of the blocked or obstructed nares.

One or more embodiments of the present invention relate to nasal cannulas and/or systems that solves or minimize the above problem by, for example, providing for the roughly proportional delivery of the therapy to each nares with the delivery being proportional to the flow of air and gas in the nares and/or inversely proportional to the resistance in the nares. This can be achieved by using the driving force of the patient's breathing, which can be generally and roughly proportional to the flow rate of air/gas into each of the nares, to proportionally split and/or pull the therapy gas into the patient's nose and subsequently into the patient's lungs. This system can deliver the dose to a patient in such a way as to ensure that the designed, set, or adequate dose can be delivered proportional to the flow of air in each nostril (or inversely proportional to the resistance of each nostril) such that the partial or full blockage (whether permanent or transient) of either or both nostril doesn't affect the amount of drug delivered to the patient.

For example, the cannula/lumen can be designed to deliver a desired quantity of the therapeutic gas such that the delivered dose can be injected and/or delivered into a flowing stream of inspiratory air, driven by the patient's breathing, with such flow splitting, downstream of the point of delivery of the drug, proportional to the amount of air going into each nostril or simply delivered to one nostril if the other nostril's flow is below a predetermined threshold such that the delivered drug can also be split proportional and/or roughly proportional or directed to one or the other nostril in an all or none configuration based on the higher flowing nostril to the said flow of gas. The flow of air in a stream to the patient can be achieved by having a flow path from the ambient air (e.g. through a simple hole in the nose piece of the cannula) to each nostril such that this flow path crosses the delivery point/area/volume of the drug before moving on to the split point leading to each nostril.

In exemplary embodiments, exemplary cannula/lumen configurations can allow the NO delivery to each nostril by injecting NO into a flow of ambient air going to each nostril (e.g., as shown in FIG. 13) and/or configurations can allow a beneficial cross flow between the two nares that can be designed and/or used to help guide NO to the unclogged nostril (e.g., as shown in FIG. 12). The delivery cannula/lumen can be designed to ensure the therapeutic gas cannot be entrained or streamed out of the path of flow of air into the patient. The delivery cannula/lumen and the flow path of inspiratory air to the patient can be designed to ensure that the delivery of the drug into the stream of air cannot be hampered or accelerated by creation of backpressure or partial lower pressure or other disruptive flow patterns at the point of injection of the drug into the ambient stream of air. The delivery cannula/lumen, the flow path of inspiratory air, the split of the air flow into the nostrils, and the individual lumen pieces in the nares can be designed to ensure that there can be adequate flow of air versus other sources of air or oxygen to the patient such that the drug can be entrained and carried into the nares proportional or substantially proportional to the flow of air in the nostrils.

Independent Nostril Delivery

One or more embodiments of the present invention relate to nasal cannulas and/or systems that address the problem of inadequate dosing due to a partially or completely blocked nostril by, for example, detecting and/or determining the amount of driving force in each nostril and adjusting the amount of drug delivered to each of the nares. This can be accomplished by using valves, baffles, flaps, and/or any other device to ensure proportional and/or substantially proportional dosing in each nostril.

Addressing at least the above, dual channel systems (e.g., that may work with multi-lumen cannulas such as quad-lumen cannulas) can utilize at least two independent flow channels: one to each nostril. In exemplary embodiments, these independent flow channels can have drug flows tailored to the inspiratory draw of each nostril, for example, by configuring the flow channels to deliver flow proportional to the draw of each nostril with total flow to both nostrils summing to the appropriate dose and/or by configuring the flow channels to deliver to the single working (e.g., high flow draw nostril) if the flow draw of the occluded nostril falls below a preset threshold.

Figure 14:
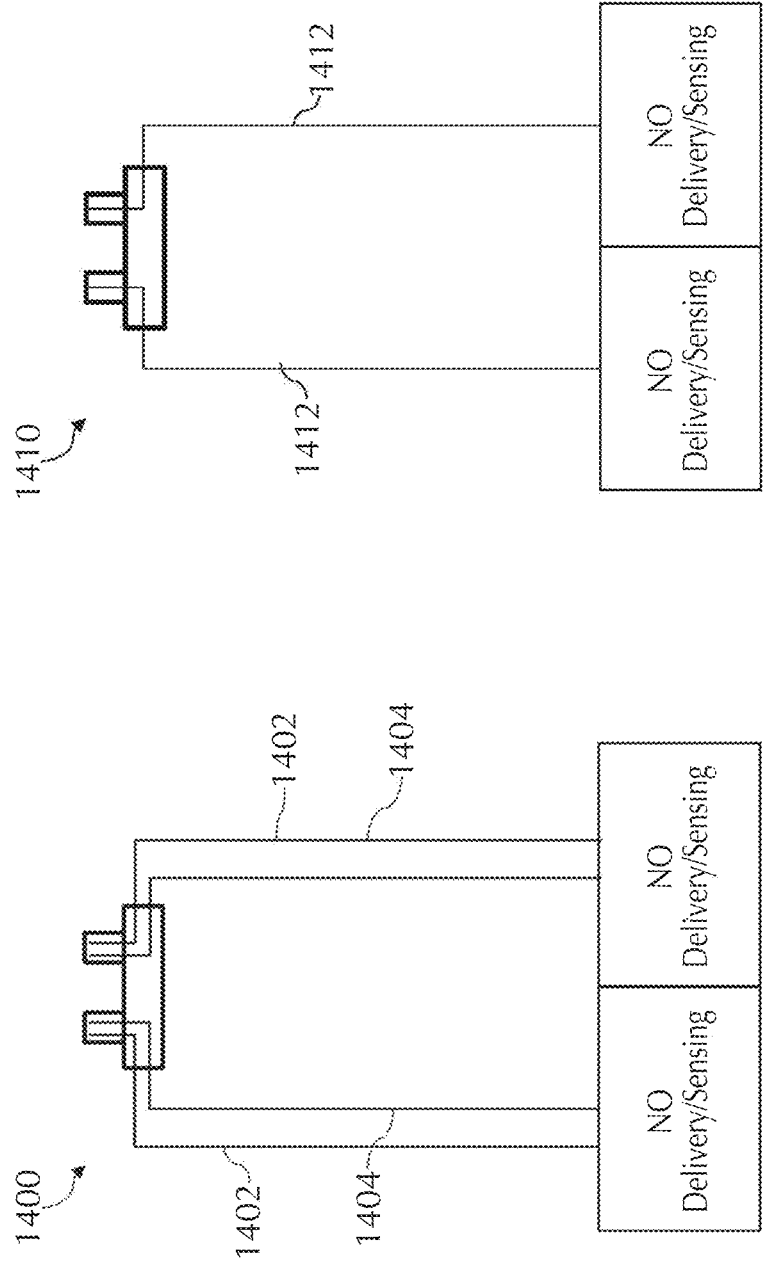
FIGS. 14A-14B show exemplary configurations of dual channel delivery systems, in accordance with exemplary embodiments of the present invention.

Referring to FIGS. 14A-14B, in order to implement such a dual channel system, it may be necessary to have two independent flow delivery channels coupled by a single (global) controller module (e.g., a control module associated with a delivery device, etc.). Each of these delivery channels can require a pressure and/or flow signal from the particular nostril of interest as well as the ability to deliver the gas to the nostril. By way of example, as illustrated in FIG. 14A, cannula 1400 can have separate sensing lumens 1402 and delivering lumens 1404 for each nostril (e.g., a dual lumen cannula, tri-lumen cannula, quad-lumen cannula, etc.). By way of another example, as illustrated in FIG. 14B, cannula 1410 can have combined sensing and delivering lumens 1412 for each nostril in which the triggering or breath detection signal can be determined and/or detected and drug delivered through the same lumen of the cannula (e.g., a single lumen cannula, dual-lumen cannula, etc.) as illustrated in FIG. 14B.

Figure 15:
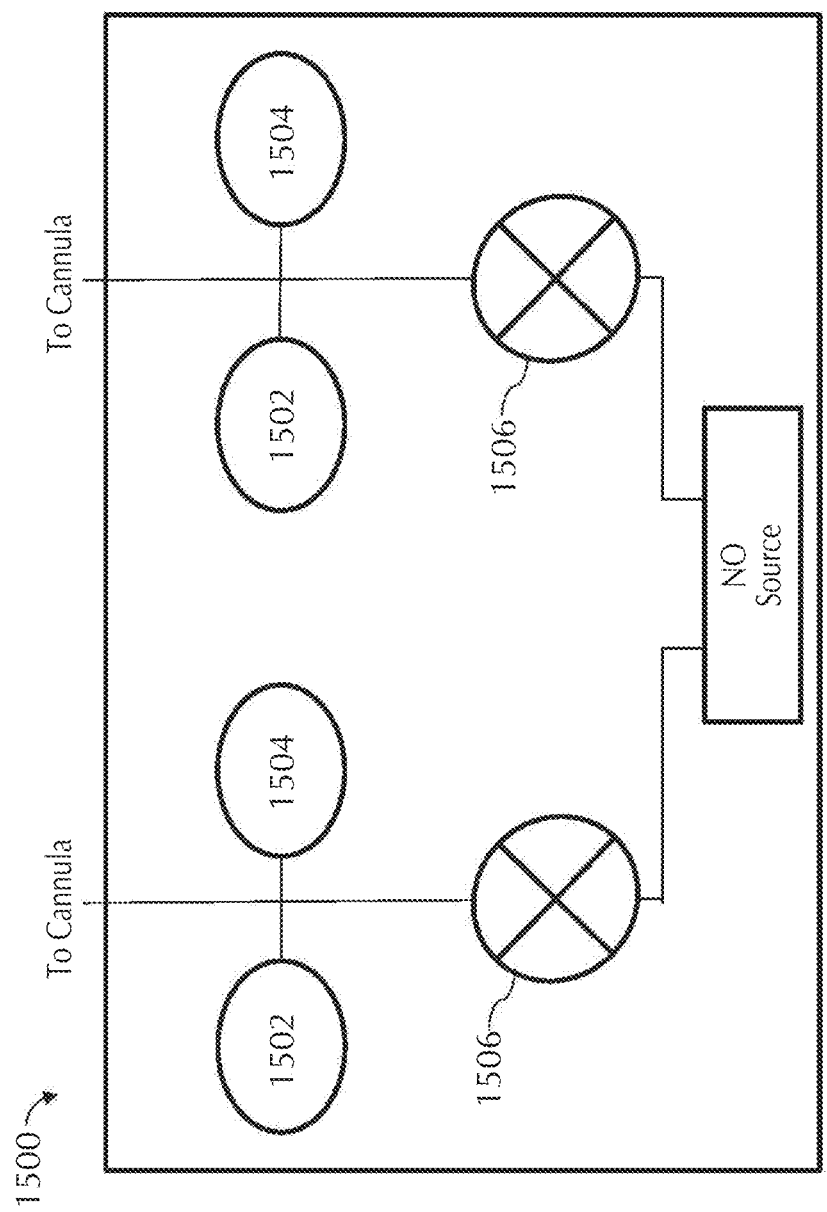
FIG. 15 shows exemplary device components for exemplary embodiments of a dual channel delivery system, in accordance with exemplary embodiments of the present invention.

Referring to FIG. 15, in exemplary embodiments, pneumatics systems 1500 (e.g., the delivery device) for the cannula may need to be implemented in order to support the above configurations of lumens (e.g., as described above) and/or may require configurations having (1) a pressure sensor(s) 1502 and/or integral flow sensor(s) 1504 which can monitor each channel independently or in pneumatic isolation and/or (2) a flow delivery mechanism(s) which might have software controlled (on-off type) solenoid valve(s) and/or software controlled proportional solenoid valve(s) 1506. Configurations using a pressure and/or flow sensor(s) can include a dedicated pressure and/or flow sensor for each delivery channel and/or a valve switched pressure and/or flow sensor(s) which can alternate between delivery channels and/or determine and/or detect pressure and/or flow readings for each channel in isolation. Pressure and/or flow can be measured (e.g., using pressure sensor(s) 1502, integral flow sensor(s) 1504, etc.) independently and/or differentially using one or more sensors. Further, one or more valves can actuate (e.g., independent, in tandem, proportionally, etc.) to deliver the appropriate amount of therapeutic gas.

In exemplary embodiments, the pneumatics channels can be controlled by a controller and/or an embedded (global) controller module that can be capable of independent control of both channels, for example, to ensure proper overall dosing. This controller can receive input from the pressure or flow sensor(s) (e.g., two separate pressure sensors, a single pressure sensor that can obtain the two pressure measurements in isolation, etc.) and can control both solenoid valves to achieve the proper dosing regimen.

Manufacturing of Multi-Lumen Nasal Cannulas

As described above, the individual lumen of a multi-lumen cannula can be separately manufactured and then affixed to each other (e.g., paratube arrangement, etc.) and/or the multiple lumina can be extruded through a single die producing a multi-lumen tube.

According to one or more embodiments, the multi-lumen nosepiece of the multi-lumen cannulas described herein can be manufactured using molding techniques. For example, the cannula can be manufactured to have a triple lumen cannula nosepiece for separate oxygen, nitric oxide, and triggering lumina.

Referring to FIG. 16, in one or more embodiments, nosepiece 1602 for a tri-lumen cannula can include three lumens, two lumens with inner diameters of about 0.08 inches (e.g., for oxygen lumen 1608 and/or triggering lumen 1066) and one lumen with a smaller inner diameter of about 0.045 inches (e.g., for nitric oxide lumen 1604). This configuration may not be readily molded by typical injection molding techniques, for example, as the small lumen may require an injector pin (of outer diameter about 0.045 inches) which may be too small to be robust (e.g., able to withstand substantially large numbers of shot pieces without bending) in a molding tool designed to last for many uses.

Referring to FIG. 17, to manufacture the multi-lumen cannula nosepiece a mold(s) can be used that can have at least two halves (e.g., 1701 and 1702) in urethane, PVC, silicone, and/or other low durometer elastomer with the internals of the large lumen 1704 and 1705) (e.g., oxygen lumen, trigger lumen, etc.) being defined by larger injector/core pins (outer diameter of about 0.08 inches) and with small half lumen indents (e.g., 1706 and 1708) defining the outline of the small lumen (e.g., NO lumen). These two halves can then be folded and bonded together, preferably with a bonding technique which does not produce residue or flash such as RF welding and/or solvent bonding, to form a whole nosepiece.

In exemplary embodiments, to circumvent the injector pin limitation with the small ID lumen being defined by indents in the halves, the two halves can be molded flat in one shot, for example, with a webbing (e.g., webbing 1709) holding the halves together and providing gross alignment during the folding and bonding process. The molded halves can, in some instances, include integral holes and mating cylindrical tabs or other complementary members (e.g., tab 1710 and tab mate 1712) so that the halves can be properly aligned when folded together. The webbing can also be optional, for example, if appropriate complementary indexing members on the two halves ensure that the two portions forming the outer wall of the NO lumen can be properly aligned. The assembled nosepiece can allow for three lumen inputs and can be connected (e.g., tee'd) to each lumen input within the internals of the nosepiece proper. Of course the nosepiece can be constructed using any reasonable technique. By way of example, a nosepiece with a substantially small NO lumen can also be constructed using liquid silicon rubber injection molding (e.g., a low pressure molding technique in which a more robust mold tool may be achieved), and/or using a low pressure molding technique. Further, a nosepiece with a substantially small NO lumen can be constructed using micromolding techniques known in the art which may be used for high resolution production of small parts including parts with small mold pins. By way of example a nosepiece with a substantially small NO lumen can be constructed using micro-molding techniques known in the art.

Referring to FIG. 18 a perspective view of the nare (e.g., nare 1716) of the multi-lumen cannula nosepiece of FIG. 17 is illustratively depicted after the two halves have been assembled.

The lumen ID can be adjusted as described above. For example, the ID of the oxygen lumen can range from about 0.05 inches to about 0.20 inches, the ID of the trigger lumen can range from about 0.05 inches to about 0.20 inches, and the ID of the NO lumen can range from about 0.01 inches to about 0.10 inches. In one or more embodiments, the IDs of the oxygen lumen and the trigger lumen can both be in the range from about 0.07 inches to about 0.09 inches and/or about 0.08 inches and the ID of the NO lumen can be in the range from about 0.035 inches to about 0.055 inches and/or about 0.045 inches.

Referring to FIG. 19A-19B, within and/or before nare 1900 the small NO lumen 1902 can exit proximal to and/or within the larger trigger lumen 1904, for example, so that any tip blockage of the larger trigger lumen (for which there may not be a purge capability) can be blown out/expelled by the function of the NO pulse. The geometry can be designed to ensure that all, and/or substantially all, NO in the larger trigger lumen can reach the respiratory system during inspiration and/or not be left behind so that it may be swept out during exhalation.

Exemplary Nasal Cannula

Figure 20:
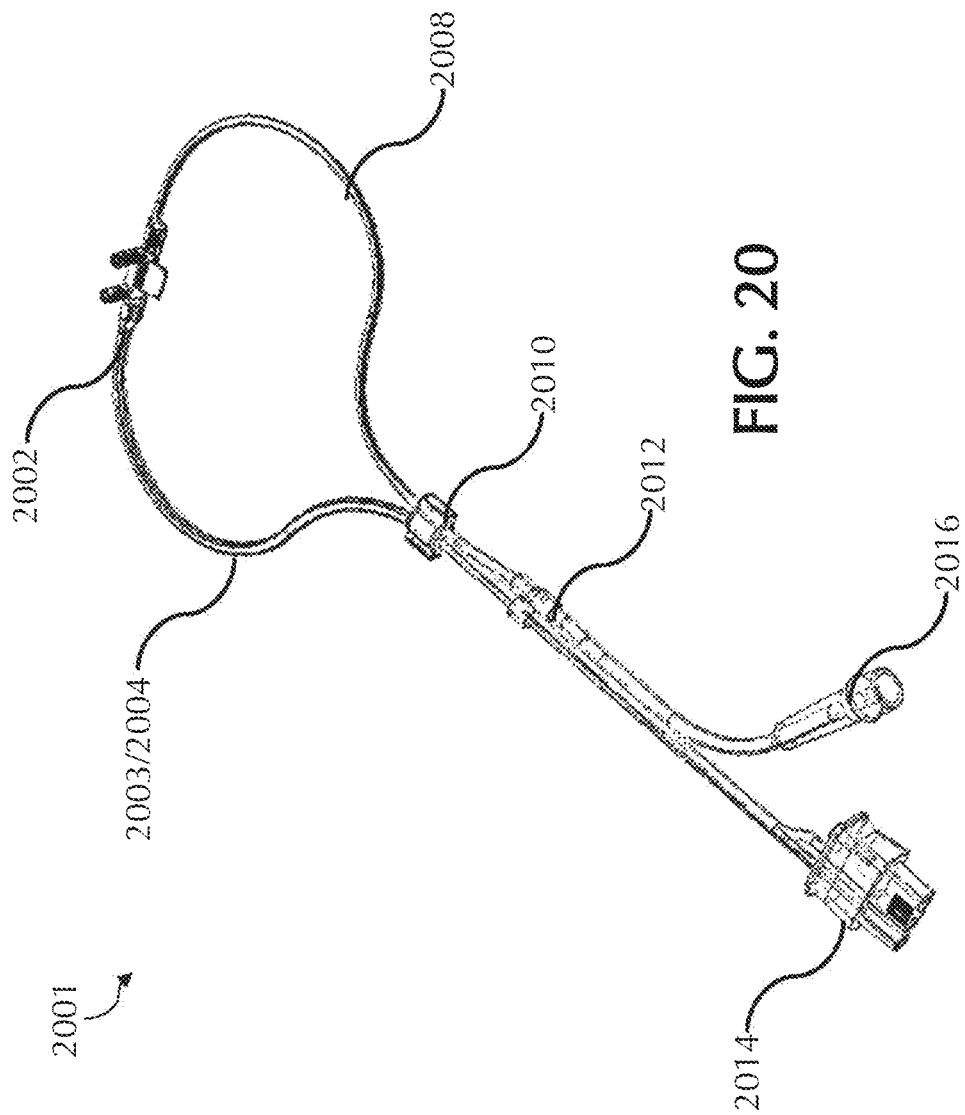
FIG. 20 shows an exemplary nasal cannula, in accordance with exemplary embodiments of the present invention.

Referring to FIG. 20, in accordance with exemplary embodiments, a nasal cannula 2001 is shown that includes three separate lumina for the delivery of oxygen, delivering NO, and for breath triggering. The nasal cannula can include a nosepiece 2002 for interfacing with the patient's nose. NO lumen 2003 and triggering lumen 200 can carry NO to the patient and transmit the pressure signal, respectively. NO lumen 2003 and trigger lumen 2004 can both be tubes (e.g., D-shaped tubes), such that their combined tubes appear as a single tube "paratube" 2003/2004. Paratube 2003/2004 can connect to the NO delivery device by nasal cannula connection piece 2014. Nasal cannula 2001 can further include keying member 2010, reducer 2012, and/or oxygen connection piece 2016 discussed in greater detail below.

Referring to FIG. 21A, the "paratube" can be formed by two tubes (e.g., two D-shaped tubes). By way of example, the D-shaped tubes can be extruded separately and/or joined in a later operation, for example, by adhering (e.g., adhesive, glue, etc.) and/or bonding (e.g., heating, melting, etc.) to form a single paratube which can appear to be a single tube. Further, the flat interface between the tube halves can be altered to have a tongue and groove type configuration enabling easy alignment of the tubes relative to each other for a subsequent bonding operation. By way of another example, the D-shaped tubes can be extruded in one operation and later split at the ends (e.g., using a splicer). Further, the D-shaped tube extrusions can be of the same materials and/or of different materials. For example, the D-shaped NO tube can be constructed of oxygen resistant materials and/or the other D-shape tube can be constructed of PVC and/or other commonly used materials for tube construction. Paratube 2003/2004 can connect to the NO delivery device by nasal cannula connection piece 2014.

Referring to FIGS. 21B and 21C, in exemplary embodiments, the inner diameter of the tubes (e.g., NO lumen 2003, trigger lumen 2004, oxygen lumen 2008, combined lumens, etc.) and/or paratube can include geometric protrusions (e.g., nubs, ribs, etc.) and/or inserts (e.g., tabs, etc.) to prevent complete tube occlusion, for example, due to kinking of the tube and/or tube compression. This geometric protrusions can be radially spaced such that they can be symmetrically and/or asymmetrically located within the tube and/or paratube.

Figure 22E:
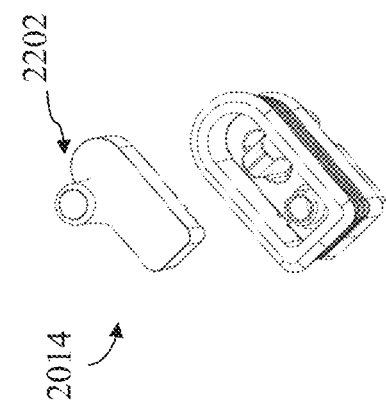
Figure 22D:
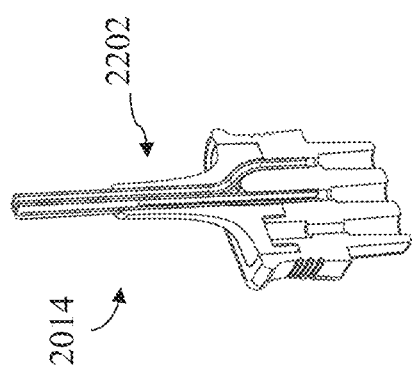
Figure 22C:
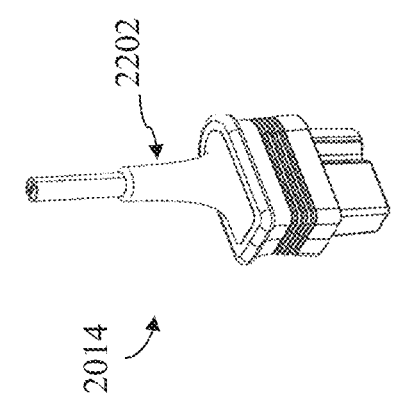

Referring to FIGS. 20 and 22A-22E, nasal cannula connection piece 2014 can be constructed to ensure fluid communication between the patient and the device. The connection piece can be plugged into the device and/or can be designed such that unidirectional connection may be required (e.g., such that it cannot be installed backwards). Further the connection piece can include additional features such as, but not limited to, a color stamped and/or differentially reflective area that can be used with IR sensing/detection to confirm insertion and/or the connection piece can include a strain relief component 2202 (e.g., as shown in FIGS. 22C-22E), that may be integral to the connection piece, to prevent kinking of the tubing, for example, as the tubing exits the connector. Of course, other techniques can be used to ensure intersection sensing/detection. Nasal cannula connection piece 2014 can include ribbing and/or substantially soft exteriors to aide in at least handling and removal of elements; strain reliefs, for example, that can be for preventing kinking. Nasal cannula connection piece 2014 can be constructed to ensure that seating of the connector in its socket can be sensed or seen by the user; to name a few.

Figure 23:
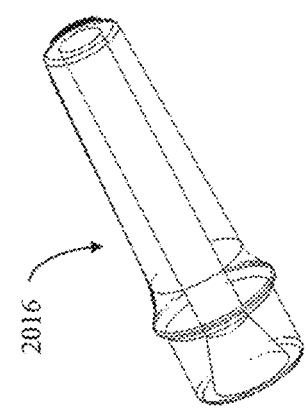
FIG. 23 shows an exemplary oxygen connection piece, in accordance with exemplary embodiments of the present invention.

Referring to FIGS. 20 and 23, in exemplary embodiments, oxygen connection piece 2016 an allow for connection to external oxygen supply devices such as, but not limited to, oxygen conservers and/or concentrators. Oxygen connection piece 2016 can be designed with industry standard dimensions, for example, to ensure ease of use and/or connection with oxygen supply devices. Further, oxygen lumen 2008 can connect to an oxygen conserver or other oxygen delivery device by oxygen connection piece 2016.

Figure 24:
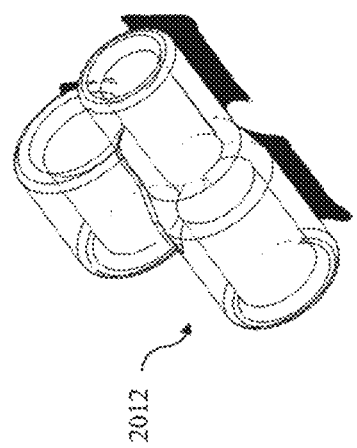
FIG. 24 shows an exemplary reducer and/or additional line holder, in accordance with exemplary embodiments of the present invention.

Referring to FIGS. 20 and 24, the NO lumen 2003, trigger lumen 2004, and oxygen lumen 2008 each can have a smaller inner and/or outer diameter by the cannula nosepiece 2002 than at the relative connection pieces 2014 and 2016. Accordingly, a reducer 2012 may be used to connect portions of the nasal cannula lumina that have different dimensions and/or cross sectional profiles. Further, reducer 2012 may also be used to terminate the oxygen lumen, for example, when no oxygen pigtail is provided, when receiving ambient air into the cannula and/or when the nasal cannula is not attached to an oxygen source, to name a few.

In exemplary embodiments, tubes (e.g., NO lumen 2003, trigger lumen 2004, oxygen lumen 2008, combined lumens, etc.) can be attached to cannula nosepiece 2002 and/or device connector (e.g., connection pieces 2014 and 2016) using any technique such as, but not limited to, bonding, adhesives (e.g., epoxy, cyanoacrylate, etc.), solvent bonding, insert molding, and/or by any other technique.

Referring to FIG. 24, reducer 2012 can allow for a transition between, and/or connection between, tubes of different dimensions (e.g., different outer diameters, different inner diameters, etc.) so tubing, for example, closest to the patient, can be optimized for patient comfort (e.g., increasing flexibility, reducing outer diameter dimensions, etc.) and/or so that the pneumatic performance of each lumen of the cannula can be optimized using multiple diameters, for example, to optimize patient comfort by minimizing the tubing diameters located proximal to the patients head.

Nosepiece

Figure 25B:
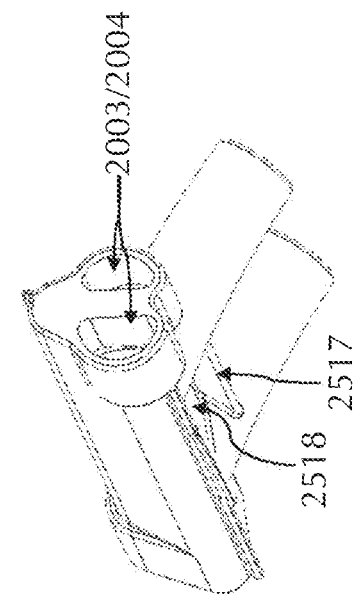
FIGS. 25A-C show various views of an exemplary cannula nosepiece, in accordance with exemplary embodiments of the present invention.
Figure 25A:
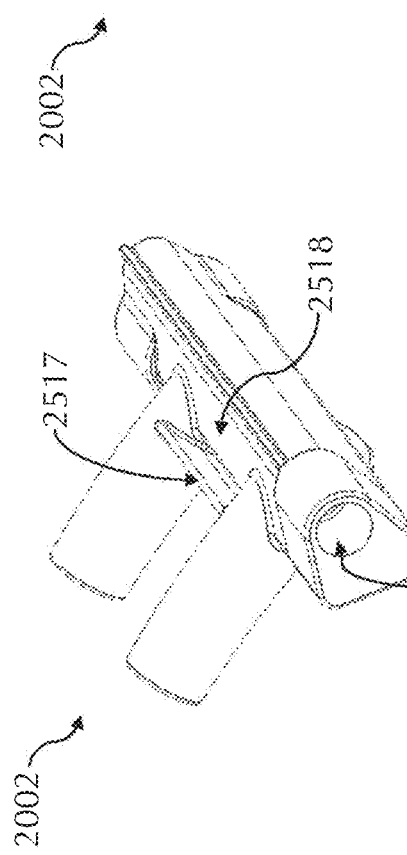
Figure 25C:
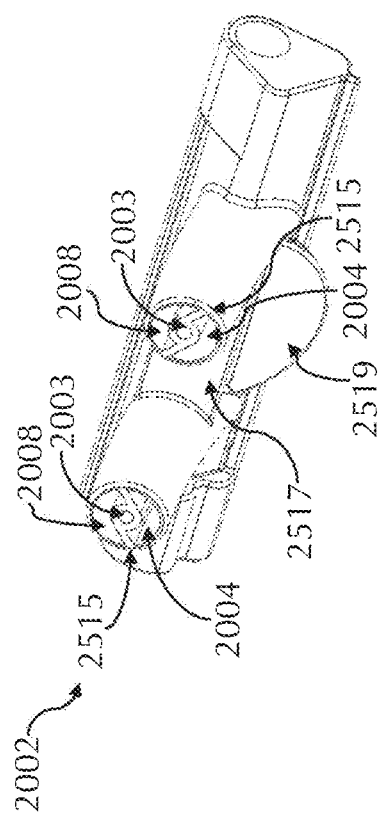
Figure 25M:
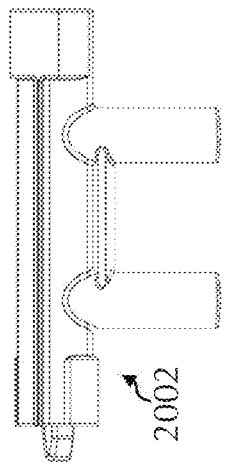
FIG. 25M shows a top view of an exemplary cannula nosepiece, in accordance with exemplary embodiments of the present invention.
Figure 25O:
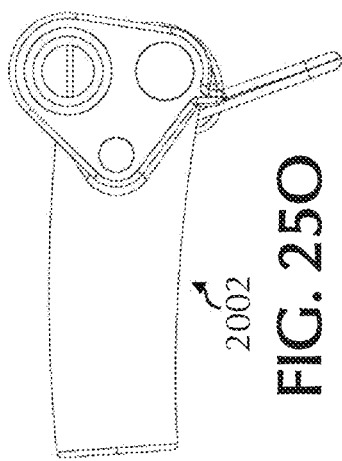
FIG. 25O shows a second side view of an exemplary cannula nosepiece, in accordance with exemplary embodiments of the present invention.
Figure 25Q:
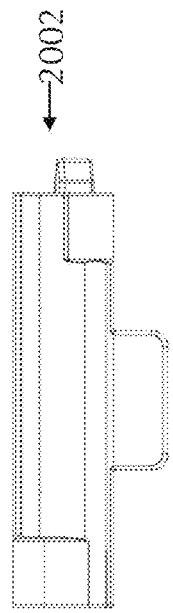
FIG. 25Q shows a back view of an exemplary cannula nosepiece, in accordance with exemplary embodiments of the present invention.
Figure 25L:
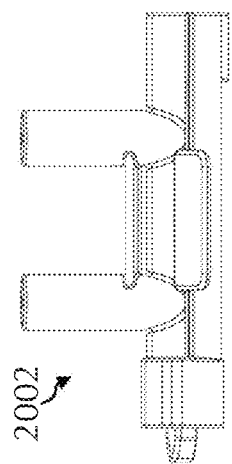
FIG. 25L shows a bottom view of an exemplary cannula nosepiece, in accordance with exemplary embodiments of the present invention.
Figure 25K:
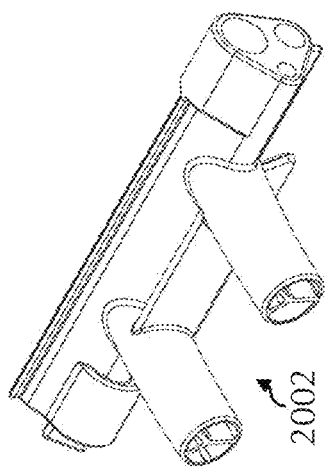
FIG. 25K shows a front top right perspective view of an exemplary cannula nosepiece, in accordance with exemplary embodiments of the present invention.
Figure 25N:
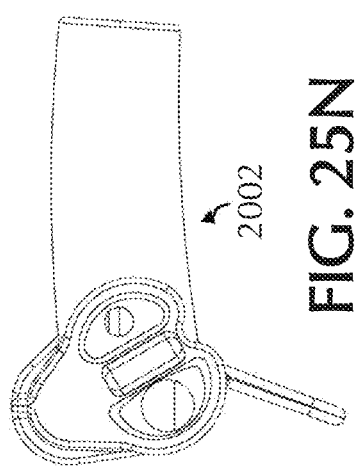
FIG. 25N shows a first side view of an exemplary cannula nosepiece, in accordance with exemplary embodiments of the present invention.
Figure 25P:
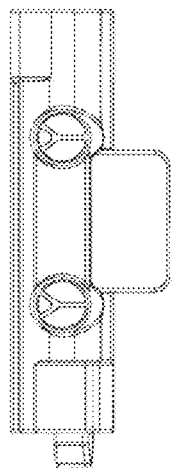
FIG. 25P shows a front view of an exemplary cannula nosepiece, in accordance with exemplary embodiments of the present invention.

Referring to FIGS. 25A-25Q various views of various exemplary cannula nosepieces 2002 are illustratively depicted. FIG. 25A shows the side of cannula nosepiece 2002 in which the oxygen lumen 2008 connects to cannula nosepiece 2002. FIG. 25B shows the two D-shaped openings for the NO lumen 2003 and the trigger lumen 2004. FIG. 25C shows each prong of the nasal cannula connection piece having a central lumen for NO and two exterior lumina for oxygen and triggering.

In exemplary embodiments, the cannula nosepiece and/or at least some of the cannula nosepiece and/or cannula can have a material properties (e.g., durometer, etc.) selected to provide the comfort while ensuring the structural and pneumatic integrity (e.g., of the cannula nosepiece, at least some of the cannula nosepiece, at least some of the cannula, etc.). For example, to provide comfort while ensuring structural and pneumatic integrity, the cannula nosepiece and/or at least some of the cannula nosepiece and/or cannula can have about 30 to 70 durometer and/or about 50 durometer (Shore A).

In exemplary embodiments, cannula nosepiece 2002 can include three lumens in a "tornado" 2515 design that can allow sufficient rigidity for the nasal nares, yet allows the nares to be partially compressible, for example, because the dividing lines for the oxygen lumen 2008 and triggering lumens 2004 can be offset (e.g., not aligned through the center of the NO delivery lumen 2003). This compressibility can allow for the nasal prong to be more flexible and comfortable than other tri-lumen cannula prong designs.

In exemplary embodiments, the tornado can also encapsulate the smaller NO lumen 2004, the nasal nares can be designed to ensure optimal and/or a desired insertion distance, and/or to increase comfort the nasal cannula can be tapered from base to end and/or can be arcuate (e.g., inwards towards the nasal openings). In exemplary embodiments, this optimal and/or desired insertion distance can be about 0.1 inches to about 0.6 inches and/or about 0.40 inches.

In exemplary embodiments, the outlet geometry of the oxygen lumen (e.g., at the cannula nosepiece) can be designed to reduce auditory frequency noise (e.g., about 20 hz to 15 khz) by, for example, tapering of the outlet of the oxygen lumen. Further, noise reduction can also be achieved by modification of the durometer of the oxygen carrying lumen to prevent auditory range oscillation and noise due to oxygen flow and/or by selecting a geometry of the oxygen lumen that does not generate noise (e.g., vibration, resonance, etc.).

Figure 26A:
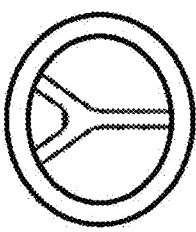
FIGS. 26A-26D show cross-sectional views of various exemplary cannula nosepiece nares, in accordance with exemplary embodiments of the present invention.
Figure 26B:
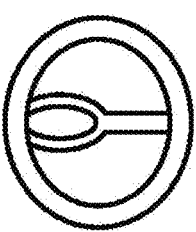
Figure 26C:
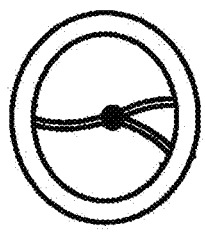
Figure 26D:
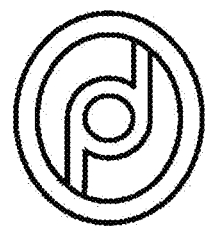

Referring to FIGS. 26A-26C, cross-sectional views show various exemplary configurations for nasal cannula nares. For example, FIG. 26A illustratively depicts a "tornado" pattern. FIGS. 26B-26D illustratively depict additional configurations that can include at least some of the benefits disclosed for the "tornado" configuration. For example, other configurations can allow sufficient rigidity for the nasal nares and can allow the nares to be partially compressible and/or other configurations that can provide at least some of the above benefits disclosed are within the scope of this invention.

In exemplary embodiments, the outer diameter of the cannula nosepiece nares can be minimized to increase patient comfort. Taking into account this outer dimension, the dimensions of the various lumens (e.g., trigger lumen, NO lumen, O2 lumen, etc.) can be selected to not only be optimized (e.g., as discussed herein) but can also be limited in size to account for patient comfort. For example, although it may be beneficial for optimization to have nares with a larger outer diameter (e.g., an outer diameter of about 0.25 inches or larger), the nares of the cannula may have an outer diameter of less than and/or about 0.2 inches for patient comfort.

By way of example, taking into account patient comfort as well as at least some and/or all of the metrics for optimization disclosed herein, a tri-lumen cannula (e.g., with a length of about 7 feet) can have tubing with an NO lumen having an ID of about 0.069 inches, a trigger lumen having an ID of about 0.089 inches, and an O2 lumen having an ID of about 0.089 inches with at least some of the lumens reducing at the cannula nosepiece (e.g., having a backplane length of about 0.59 inches) and/or reducing (e.g., reducing again) at the nares (e.g., having a length of about 0.47 inches) of the cannula nosepiece. For example, at the cannula nosepiece the NO lumen can be reduced to an ID of about 0.049 inches, the trigger lumen can have an ID of about 0.089 inches, and/or the O2 lumen can have an ID of about 0.089 inches. Still following the above example, at the nares of cannula nosepiece the NO lumen can be reduced to an ID of about 0.038 inches, the trigger lumen can be reduced to an ID of about 0.079 inches, and/or the O2 lumen can be reduced to an ID of about 0.079 inches. Further, prior to the reducer and/or connection piece the NO lumen can have an ID of about 0.069 inches, the trigger lumen can have an ID of about 0.089 inches, and the O2 lumen can have an ID of about 0.132 inches.

By way of example, taking into account patient comfort as well as at least some and/or all of the metrics for optimization disclosed herein, a tri-lumen cannula (e.g., with a length of about 3 feet) can have tubing with an NO lumen having an ID of about 0.064 inches, a trigger lumen having an ID of about 0.084 inches, and an O2 lumen having an ID of about 0.084 inches with at least some of the lumens reducing at the cannula nosepiece (e.g., having a backplane length of about 0.59 inches) and/or reducing (e.g., reducing again) at the nares (e.g., having a length of about 0.47 inches) of the cannula nosepiece. For example, at the cannula nosepiece the NO lumen can be reduced to an ID of about 0.044 inches, the trigger lumen can have an ID of about 0.084 inches, and/or the O2 lumen can have an ID of about 0.084 inches. Still following the above example, at the nares of cannula nosepiece the NO lumen can be reduced to an ID of about 0.036 inches, the trigger lumen can be reduced to an ID of about 0.074 inches, and/or the O2 lumen can be reduced to an ID of about 0.074 inches. Further, prior to the reducer and/or connection piece the NO lumen can have an ID of about 0.064 inches, the trigger lumen can have an ID of about 0.084 inches, and the O2 lumen can have an ID of about 0.127 inches.

By way of example, taking into account patient comfort as well as at least some and/or all of the metrics for optimization disclosed herein, a tri-lumen cannula (e.g., with a length of about 15 feet) can have tubing with an NO lumen having an ID of about 0.074 inches, a trigger lumen having an ID of about 0.094 inches, and an O2 lumen having an ID of about 0.094 inches with at least some of the lumens reducing at the cannula nosepiece (e.g., having a backplane length of about 0.59 inches) and/or reducing (e.g., reducing again) at the nares (e.g., having a length of about 0.47 inches) of the cannula nosepiece. For example, at the cannula nosepiece the NO lumen can be reduced to an ID of about 0.054 inches, the trigger lumen can have an ID of about 0.094 inches, and/or the O2 lumen can have an ID of about 0.094 inches. Still following the above example, at the nares of cannula nosepiece the NO lumen can be reduced to an ID of about 0.04 inches, the trigger lumen can be reduced to an ID of about 0.084 inches, and/or the O2 lumen can be reduced to an ID of about 0.084 inches. Further, prior to the reducer and/or connection piece the NO lumen can have an ID of about 0.074 inches, the trigger lumen can have an ID of about 0.094 inches, and the O2 lumen can have an ID of about 0.137 inches.

By way of example, taking into account patient comfort as well as at least some and/or all of the metrics for optimization disclosed herein, a quad-lumen cannula (e.g., with a length of about 7 feet) can have tubing with at least one NO lumen having an ID of about 0.069 inches, at least one trigger lumen having an ID of about 0.089 inches, and an O2 lumen having an ID of about 0.089 inches with at least some of the lumens reducing at the cannula nosepiece (e.g., having a backplane length of about 0.59 inches) and/or reducing (e.g., reducing again) at the nares (e.g., having a length of about 0.47 inches) of the cannula nosepiece. For example, at the cannula nosepiece the NO lumen(s) can be reduced to an ID of about 0.049 inches, the trigger lumen(s) can have an ID of about 0.089 inches, and/or the O2 lumen can have an ID of about 0.089 inches. Still following the above example, at the nares of cannula nosepiece the NO lumen(s) can be reduced to an ID of about 0.038 inches, the trigger lumen(s) can be reduced to an ID of about 0.079 inches, and/or the O2 lumen can be reduced to an ID of about 0.079 inches. Further, prior to the reducer and/or connection piece the NO lumen(s) can have an ID of about 0.069 inches, the trigger lumen(s) can have an ID of about 0.089 inches, and the O2 lumen can have an ID of about 0.132 inches.

By way of example, taking into account patient comfort as well as at least some and/or all of the metrics for optimization disclosed herein, a quad-lumen cannula (e.g., with a length of about 3 feet) can have tubing with at least one NO lumen having an ID of about 0.064 inches, at least one trigger lumen having an ID of about 0.084 inches, and an O2 lumen having an ID of about 0.084 inches with at least some of the lumens reducing at the cannula nosepiece (e.g., having a backplane length of about 0.59 inches) and/or reducing (e.g., reducing again) at the nares (e.g., having a length of about 0.47 inches) of the cannula nosepiece. For example, at the cannula nosepiece the NO lumen(s) can be reduced to an ID of about 0.044 inches, the trigger lumen(s) can have an ID of about 0.084 inches, and/or the O2 lumen can have an ID of about 0.084 inches. Still following the above example, at the nares of cannula nosepiece the NO lumen(s) can be reduced to an ID of about 0.036 inches, the trigger lumen(s) can be reduced to an ID of about 0.074 inches, and/or the O2 lumen can be reduced to an ID of about 0.074 inches. Further, prior to the reducer and/or connection piece the NO lumen(s) can have an ID of about 0.064 inches, the trigger lumen(s) can have an ID of about 0.084 inches, and the O2 lumen can have an ID of about 0.127 inches.

By way of example, taking into account patient comfort as well as at least some and/or all of the metrics for optimization disclosed herein, a quad-lumen cannula (e.g., with a length of about 15 feet) can have tubing with at least one NO lumen having an ID of about 0.074 inches, at least one trigger lumen having an ID of about 0.094 inches, and an O2 lumen having an ID of about 0.094 inches with at least some of the lumens reducing at the cannula nosepiece (e.g., having a backplane length of about 0.59 inches) and/or reducing (e.g., reducing again) at the nares (e.g., having a length of about 0.47 inches) of the cannula nosepiece. For example, at the cannula nosepiece the NO lumen(s) can be reduced to an ID of about 0.054 inches, the trigger lumen(s) can have an ID of about 0.094 inches, and/or the O2 lumen can have an ID of about 0.094 inches. Still following the above example, at the nares of cannula nosepiece the NO lumen(s) can be reduced to an ID of about 0.04 inches, the trigger lumen(s) can be reduced to an ID of about 0.084 inches, and/or the O2 lumen can be reduced to an ID of about 0.084 inches. Further, prior to the reducer and/or connection piece the NO lumen(s) can have an ID of about 0.074 inches, the trigger lumen(s) can have an ID of about 0.094 inches, and the O2 lumen can have an ID of about 0.137 inches.

By way of example, taking into account patient comfort as well as at least some and/or all of the metrics for optimization disclosed herein, a dual-lumen cannula (e.g., with a length of about 7 feet) can have tubing with a combined NO/trigger lumen having an ID of about 0.07 inches and an O2 lumen having an ID of about 0.089 inches with at least some of the lumens reducing at cannula nosepiece (e.g., having a backplane length of about 0.59 inches) and/or reducing (e.g., reducing again) at the nares (e.g., having a length of about 0.47 inches) of the cannula nosepiece. For example, at the cannula nosepiece the combined NO/trigger lumen can be reduced to an ID of about 0.05 inches and/or the O2 lumen can have an ID of about 0.089 inches. Still following the above example, at the nares of cannula nosepiece the combined NO/trigger lumen can be reduced to an ID of about 0.04 inches and/or the O2 lumen can be reduced to an ID of about 0.079 inches. Each of these dimensions for the combined NO/trigger lumen may be increased slightly (e.g., by a few thousands), for example, to reduce trigger signal attenuation. Further, prior to the reducer and/or connection piece the combined NO/trigger lumen can have an ID of about 0.07 inches, and the O2 lumen can have an ID of about 0.132 inches.

By way of example, taking into account patient comfort as well as at least some and/or all of the metrics for optimization disclosed herein, a dual-lumen cannula (e.g., with a length of about 3 feet) can have tubing with a combined NO/trigger lumen having an ID of about 0.064 inches and an O2 lumen having an ID of about 0.084 inches with at least some of the lumens reducing at the cannula nosepiece (e.g., having a backplane length of about 0.59 inches) and/or reducing (e.g., reducing again) at the nares (e.g., having a length of about 0.47 inches) of the cannula nosepiece. For example, at the cannula nosepiece the combined NO/trigger lumen can be reduced to an ID of about 0.044 inches and/or the O2 lumen can have an ID of about 0.0.084 inches. Still following the above example, at the nares of cannula nosepiece the combined NO/trigger lumen can be reduced to an ID of about 0.036 inches and/or the O2 lumen can be reduced to an ID of about 0.074 inches. Each of these dimensions for the combined NO/trigger lumen may be increased slightly (e.g., by a few thousands), for example, to reduce trigger signal attenuation. Further, prior to the reducer and/or connection piece the combined NO/trigger lumen can have an ID of about 0.064 inches, and the O2 lumen can have an ID of about 0.127 inches.

By way of example, taking into account patient comfort as well as at least some and/or all of the metrics for optimization disclosed herein, a dual-lumen cannula (e.g., with a length of about 15 feet) can have tubing with a combined NO/trigger lumen having an ID of about 0.074 inches and an O2 lumen having an ID of about 0.094 inches with at least some of the lumens reducing at cannula nosepiece (e.g., having a backplane length of about 0.59 inches) and/or reducing (e.g., reducing again) at the nares (e.g., having a length of about 0.47 inches) of the cannula nosepiece. For example, at the cannula nosepiece the combined NO/trigger lumen can be reduced to an ID of about 0.054 inches and/or the O2 lumen can have an ID of about 0.094 inches. Still following the above example, at the nares of cannula nosepiece the combined NO/trigger lumen can be reduced to an ID of about 0.040 inches and/or the O2 lumen can be reduced to an ID of about 0.084 inches. Each of these dimensions for the combined NO/trigger lumen may be increased slightly (e.g., by a few thousandths of an inch), for example, to reduce trigger signal attenuation. Further, prior to the reducer and/or connection piece the combined NO/trigger lumen can have an ID of about 0.074 inches, and the O2 lumen can have an ID of about 0.137 inches.

Trampoline

In exemplary embodiments, cannula nosepiece 2002 can include a flexible support bridge or "trampoline" 2517 that can cushion the nasal septum. Flexible support bridge 2517 can provide increased patient comfort by, for example, increasing the surface area of contact between the cannula and the nasal septum and/or patient comfort can be increased because the prong bridge can be designed to deflect away from the nasal septum.

In exemplary embodiments, flexible support bridge 2517 can be an element (e.g., free floating element) that may be supported on both ends by the prongs of the nasal cannula. Rather than having a patient nose (e.g., nasal septum) rest on a central bridge member 2518 commonly found in nasal cannulas (e.g., that separates the nares of a nasal cannula; a hard plastic connection, sometimes curved, between the nares of a nasal cannula; etc.) flexible support bridge 2517 can be an element (e.g., additional to central bridge 2518, traversing at least some of central bridge 2518, traversing from one nare to another nare, etc.) contacting the patient's septum thereby providing at least increased comfort to the patient. In exemplary embodiments, flexible support bridge 2517 can "give" and/or "bend" towards central bridge member 2518 when the cannula is worn. The "give" and/or "bending" of flexible support bridge 2517 can smooth transient forces on the nasal septum due to patient movement or cannula movement. The "give" and/or "bending" can also increase surface area of contact with the nasal septum, which in turn can reduce the force on the nasal septum at any one point thereby improving comfort (e.g., as comfort may be adversely affected by increasing point load on the nasal septum).

In exemplary embodiments, flexible support bridge 2517 can restrict the depth of insertion of the nasal nares, for example, as mentioned above, to an optimal and/or desired insertion distance of about 0.1 inches to about 0.6 inches and/or about 0.40 inches. By way of example, this distance can be shorter than the nasal nares length extending from central bridge 2518.

In exemplary embodiments, the nasal cannula nosepiece can include a tab 2519 between the nares (e.g., extending from central bridge 2518) that can allow the nasal cannula connection piece to sit properly on the upper lip. Tab 2519 can provide an additional measure of patient comfort by, for example, orienting the nares so the nares point inwards towards the nostril openings and/or can distribute force on the upper lip over a larger surface area thereby improving patient comfort.

Figure 27:
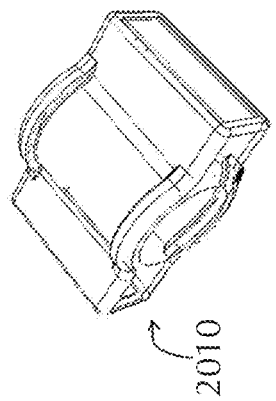
FIG. 27 show exemplary keying elements, in accordance with exemplary embodiments of the present invention.

Referring to FIGS. 20 and 27, in exemplary embodiments, the nasal cannula can include a keying member 2010, described in further detail below. In exemplary embodiments, keying member 2010 can be a bolo and/or can be part of a bolo that can be included that can be used to adjust the length of the cannula section proximal to the nosepiece, for example, to increase patient comfort by ensuring the cannula fits around the head of the wearer.

In exemplary embodiments, the nasal cannula can further include ear pads that can, for example, slide over and/or be built into the cannula tubing at the point where the cannula tubing wraps the ears to improve comfort and/or the ear pads can be foam tube extrusions which may have axial slits so they can slide over the cannula tubing.

Although this exemplary nasal cannula may be described as having certain components, any and all of these components may be optional, may be eliminated, and/or can be combined and/or further separated. Furthermore, the nasal cannula may have any of the other components or materials otherwise described herein.

Cannula Keying

During the purging and/or washout procedure that can be used to clear the nasal cannula of air and other gases prior to NO delivery, air/gases can be purged by flowing NO-containing gas through the nasal cannula. However, due to the reaction of NO and the oxygen in the air, this washout procedure can produce NO2. Accordingly, it can be important that the patient not be wearing the nasal cannula during the purging and/or washout procedure, for example, so that the NO2 cannot be administered to the patient.

Referring back to FIG. 20, one or more embodiments of the present invention can provide a keying element 2010 on the nasal cannula. Such a keying element may be affixed close to the nares of the nasal cannula, such as within 5-25 inches of the nares of the cannula. One or more exemplary embodiment of such a keying element can be seen referring to element 2010 as shown in FIG. 20. The keying element can be provided as a bolo that can sit on a patient's chest and/or neck when the cannula is worn by the patient.

Figure 28:
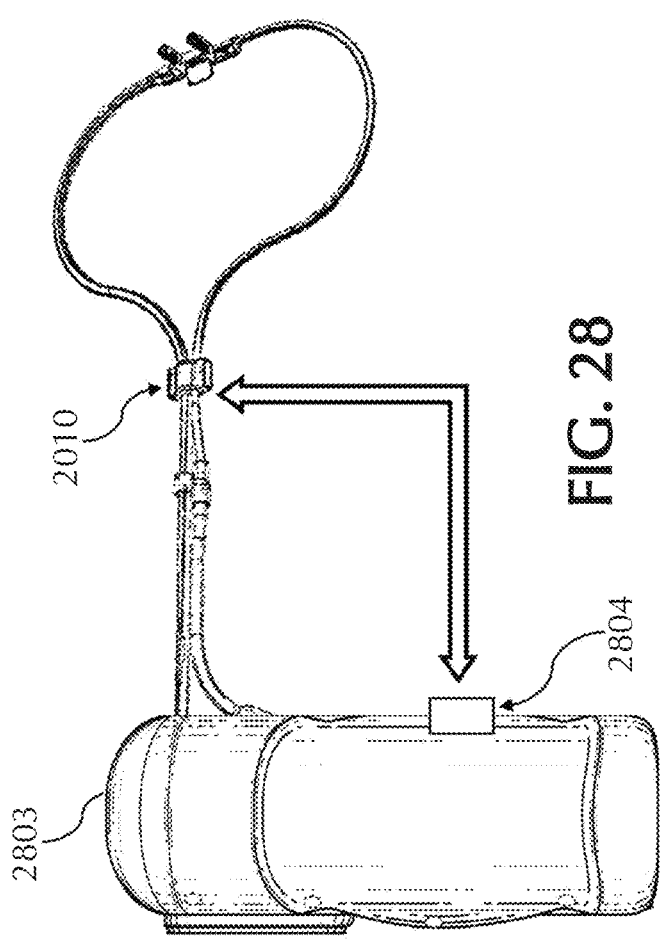
FIG. 28 shows an exemplary NO delivery device with a key slot and a nasal cannula with a keying element, in accordance with exemplary embodiments of the present invention.

Referring to FIG. 28, keying element 2010 may need to be plugged into the NO delivery device 2803 with a key slot or keyhole 2804 and/or this may need to be done during the washout procedure. Due to the proximity of the keying device and the nares, the nares of the nasal cannula cannot be in the nares of the patient's nose when the keying element is plugged into the NO delivery device.

In one or more exemplary implementations of a NO delivery device with a keyhole and a nasal cannula with a keying element, the NO delivery device can perform the following functions:

a. The NO delivery device can prompt the patient to remove the cannula and insert the keying element contained on the cannula into a keyhole in the NO delivery device.

b. The keyhole can detect the presence of the key in the keyhole. Exemplary methods for detecting the presence of the key include, but are not limited to, electronic detection (e.g. light beam detector, actuated switch, IR detection, magnetic detection, etc.) or mechanical detection (e.g. microswitch)

c. The NO delivery device can ensure that the key is in the keyhole before performing the washout procedure and can be programmed to not perform the maneuver if the key is not in the keyhole.

d. The NO delivery device can then perform the washout procedure and inform the user of the completion of the procedure.

e. The NO delivery device can allow the user the remove the key from the keyhole for initiation of NO therapy.

In exemplary embodiments, the keying element and/or key slot can be used to ensure that the patient is not wearing the nasal cannula during the purging and/or washout procedure. In exemplary embodiments, the keying element and/or key slot can be used to ensure authenticity of at least the cannula, expiration of at least the cannula. For example, the keying element and/or key slot can be used to limit the number of cannula uses and/or not allow patients to re-use the cannula. For another example, in the event of a need to ensure patients not use the cannula, the keying element and/or key slot can be used prevent users from using defected cannula.

It will be understood that any of the above teachings (e.g., trampoline, tab, paratube, connection piece, oxygen connection piece, reducer, keying member, keying, bolo, cannula constructs, nosepiece constructs, etc.) can be combined with any of the other pneumatic configurations, cannula configurations, and/or teachings and/or embodiments described herein. For example, the above teachings (e.g., trampoline, tab, paratube, connection piece, oxygen connection piece, reducer, keying member, keying, bolo, cannula constructs, nosepiece constructs, etc.) can be used with mono-lumen cannulas, dual-lumen cannulas, tri-lumen cannulas, quad-lumen cannulas, and/or any other teachings and/or embodiments described herein.

EXAMPLES

Figure 30:
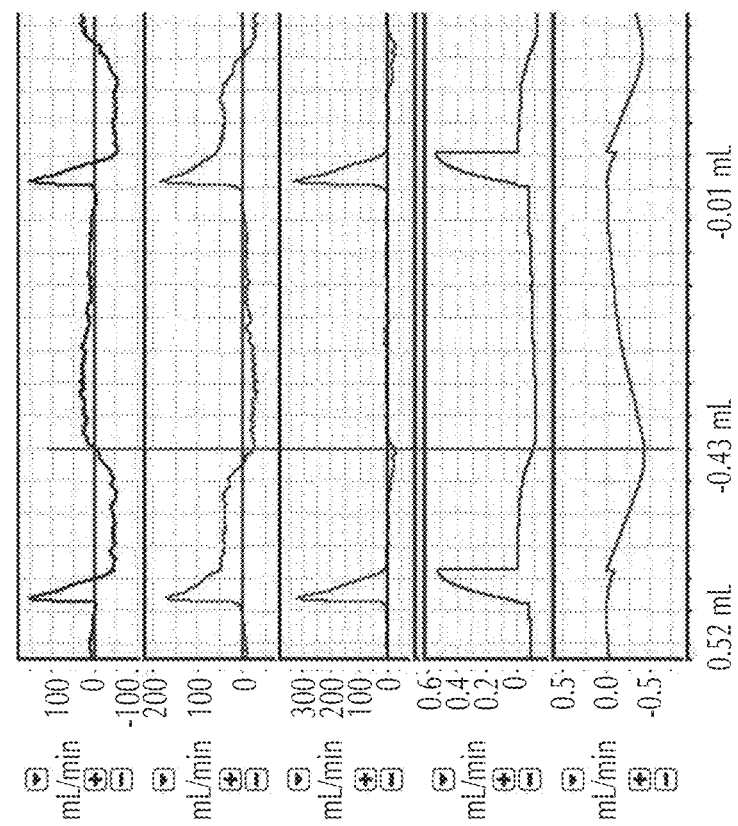
FIG. 30 illustratively depicts exemplary retrograde flows during both inspiratory and expiratory breathing, in accordance with exemplary embodiments of the present invention.
Figure 29:
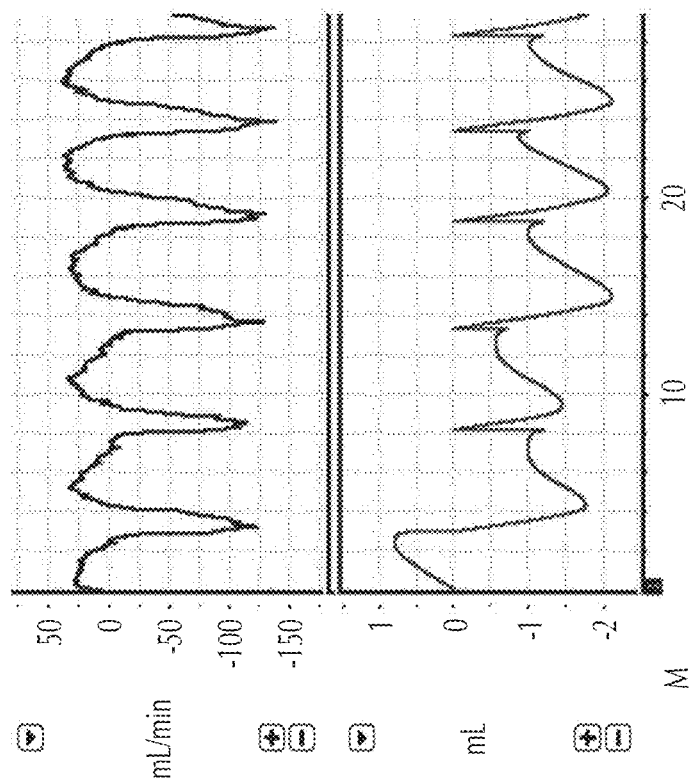
FIG. 29 illustratively depicts exemplary retrograde flows during inspiratory breathing along with pulsed delivery, in accordance with exemplary embodiments of the present invention.
Figure 33B:
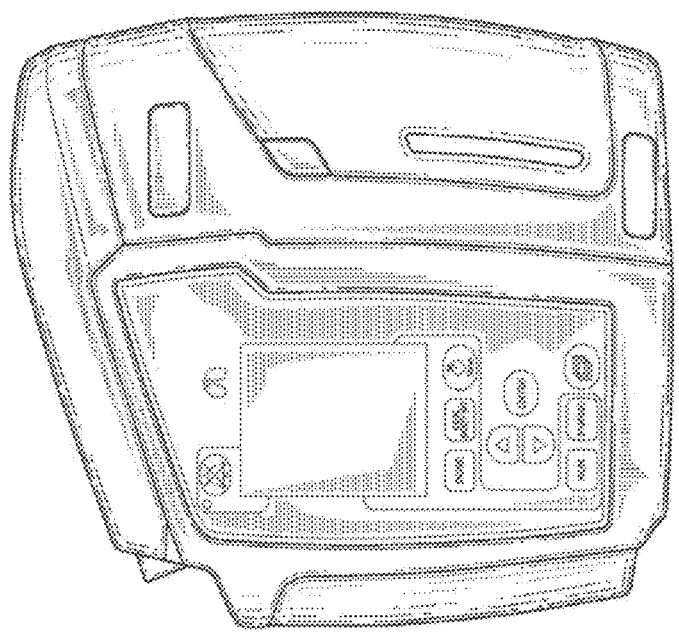
FIG. 33B shows a front view of an exemplary therapeutic gas delivery device, in accordance with exemplary embodiments of the present invention.
Figure 33A:
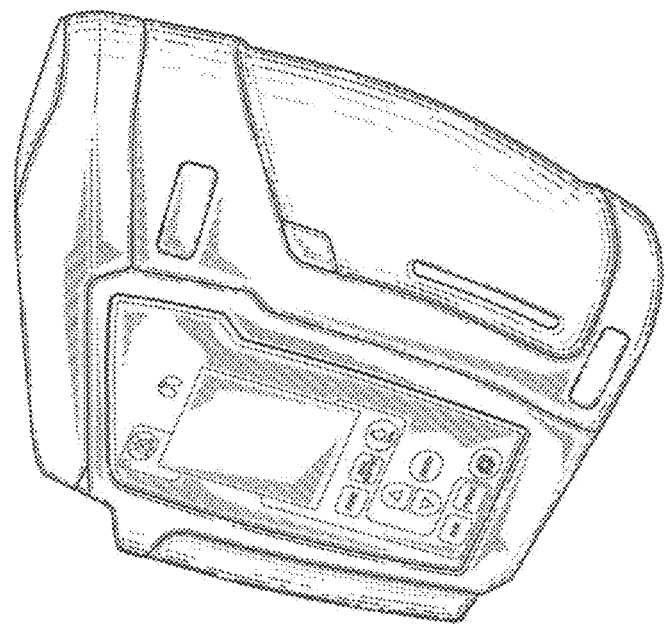
FIG. 33A shows a front top right perspective view of an exemplary therapeutic gas delivery device, in accordance with exemplary embodiments of the present invention.
Figure 33D:
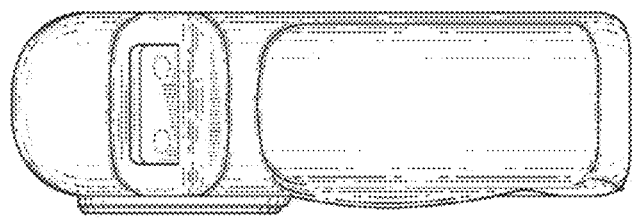
FIG. 33D shows a first side view of an exemplary therapeutic gas delivery device, in accordance with exemplary embodiments of the present invention.
Figure 33E:
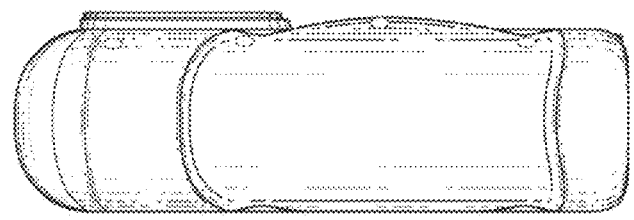
FIG. 33E shows a second side view of an exemplary therapeutic gas delivery device, in accordance with exemplary embodiments of the present invention.
Figure 33G:
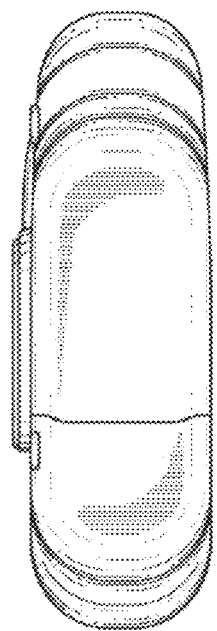
FIG. 33G shows a bottom view of an exemplary therapeutic gas delivery device, in accordance with exemplary embodiments of the present invention.
Figure 33C:
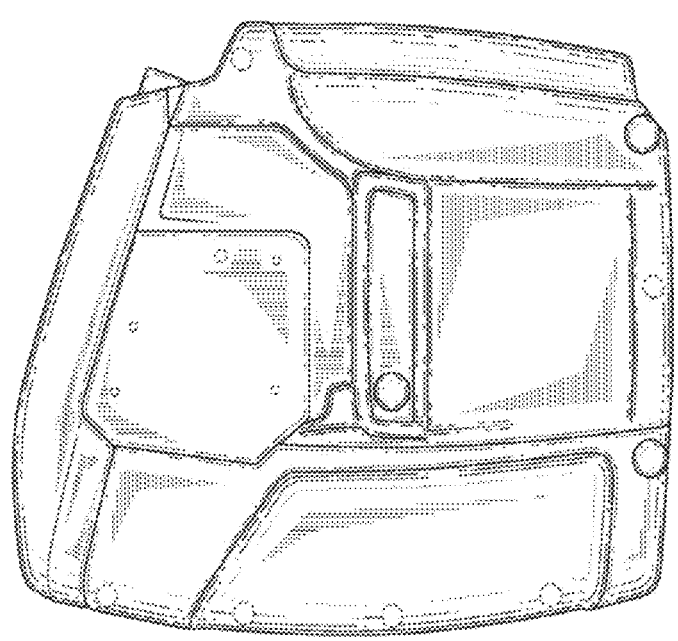
FIG. 33C shows a back view of an exemplary therapeutic gas delivery device, in accordance with exemplary embodiments of the present invention.
Figure 33F:
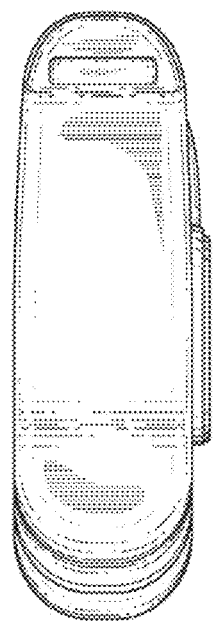
FIG. 33F shows a top view of an exemplary therapeutic gas delivery device, in accordance with exemplary embodiments of the present invention.
Figure 34B:
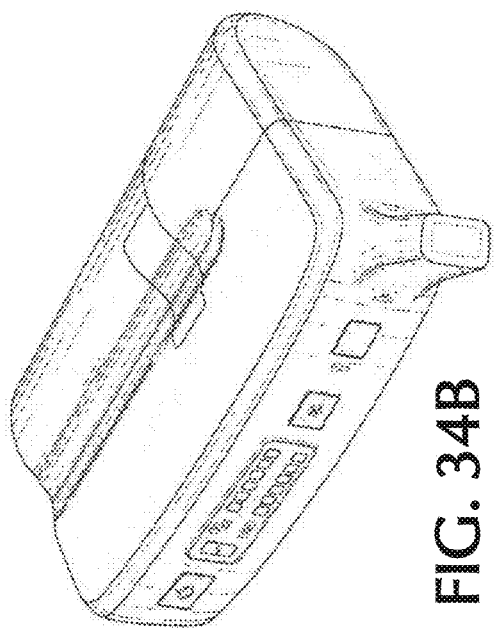
FIG. 34B shows a front top right perspective view of another exemplary therapeutic gas delivery device, in accordance with exemplary embodiments of the present invention.
Figure 34D:
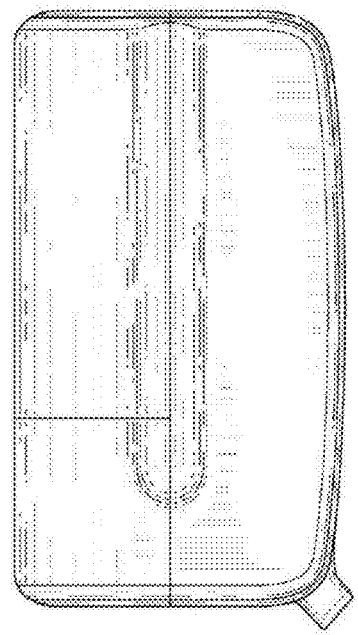
FIG. 34D shows a bottom view of another exemplary therapeutic gas delivery device, in accordance with exemplary embodiments of the present invention.
Figure 34A:
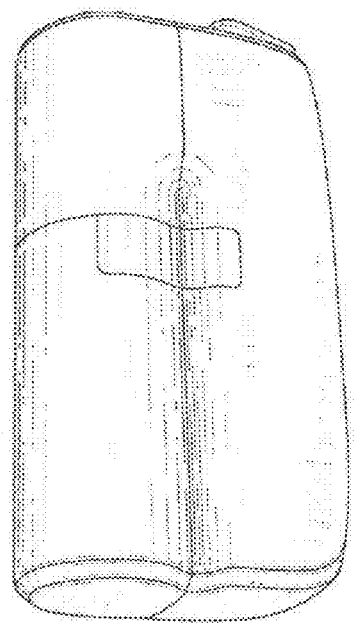
FIG. 34A shows a top left back perspective view of another exemplary therapeutic gas delivery device, in accordance with exemplary embodiments of the present invention.
Figure 34C:
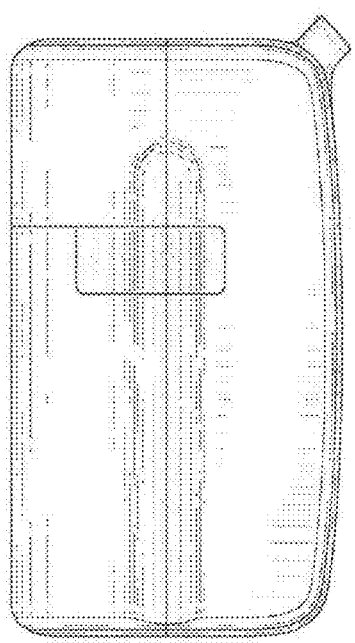
FIG. 34C shows a top view of another exemplary therapeutic gas delivery device, in accordance with exemplary embodiments of the present invention.
Figure 34F:
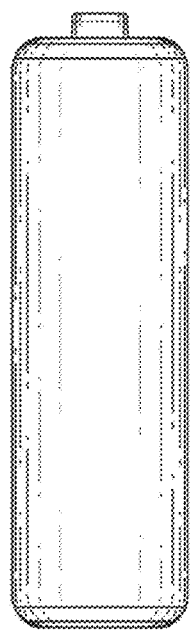
FIG. 34F shows a back view of another exemplary therapeutic gas delivery device, in accordance with exemplary embodiments of the present invention.
Figure 34H:
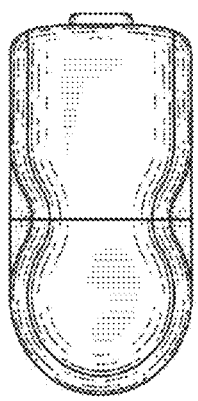
FIG. 34H shows a second side view of another exemplary therapeutic gas delivery device, in accordance with exemplary embodiments of the present invention.
Figure 34E:
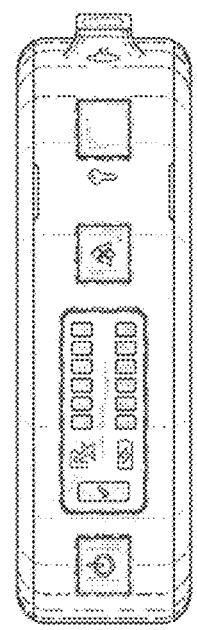
FIG. 34E shows a front view of another exemplary therapeutic gas delivery device, in accordance with exemplary embodiments of the present invention.
Figure 34G:
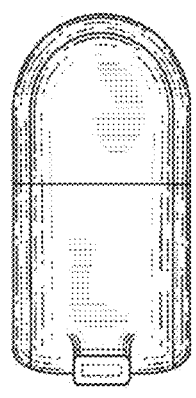
FIG. 34G shows a first side view of another exemplary therapeutic gas delivery device; in accordance with exemplary embodiments of the present invention.

Referring to FIGS. 29-30, an example of retrograde flow during inspiratory breath along with pulsed delivery is shown at FIG. 29 and an example of retrograde flow during both inspiratory and expiratory breath is shown at FIG. 30.

Referring to FIGS. 31 and 32A, 32B, and 32C, the retrograde flow for various nasal cannula configurations was tested. Typical nasal cannulas that deliver to both nares result in significant retrograde flow as shown in Test 1 of FIG. 31. The nasal cannula configuration of Test 1 is shown in FIG. 32A. For Test 2, the interconnect between the two nares was occluded to increase the distance between the nares to approximately 19 inches in the hopes that would eliminate the retrograde flow. The nasal cannula configuration of Test 2 is shown in FIG. 32B. As shown in Test 2 of FIG. 31, while the total volume of retrograde flow could be reduced, it was not eliminated. Further occluding the pathway with a 7 foot distance between the nares, as shown in FIG. 32C, had minimal further impact, as shown in Test 3 of FIG. 31. Surprisingly, it was found that the only way tested that completely eliminated the retrograde flow was when separate circuits were used for the NO delivery to each of the nares (i.e. a dual channel delivery system).

The document attached to U.S. Provisional Application No. 61/856,367, filed Jul. 19, 2013 as Appendix 1, titled "Exploratory Evaluation of Nitrogen Dioxide Formation in Candidate Nitric Oxide Delivery Lumena," examined the concentration of NO2 anticipated to be present in the iNO delivery lumen of tri-lumen cannulas made of various materials. Appendix 1 attached to U.S. Provisional Application No. 61/856,367, filed Jul. 19, 2013 is incorporated by reference herein in its entirety; to the extent it is not inconsistent with the present invention. The experimental technique involved the flowing of 2440 ppm nitric oxide (balance nitrogen) gas through multiple tubes (of three material types) arranged in parallel such that proximal (based on the circuit without the tubes) and distal readings of the effluent NO2 content could be taken using a CAPs NO2 bench. Parallel tubes were used to improve the signal-to-noise ratio (i.e. to magnify the NO2 signal strength) of the data and a final mathematical calculation of individual tube NO2 change was obtained. The flow of nitric oxide through the parallel tubing banks was set to equate to a residence time of 7.57 min/tube (e.g., based on a 50 kg patient with dosing set to 0.003 mg/kg*hr with an iNO delivery tube of 84 inches length and 0.076 inches inner diameter). The "per tube" expected NO2 rise for the three material types tested is shown in below.

| Per Tube Delivered NO2 Levels | |
| --- | --- |
| Tubing Material | Per tube NO2 level |
| Polyvinyl Chloride | 12.7 ppm |
| Silicone | 10.9 ppm |
| Polyurethane | 6.8 ppm |

Methods of Treatment

The invention herein can reduce retrograde flow, ensure accurate dose delivery, and/or minimize NO2 formation and used in conjunction with a delivery device can be used for the treatment and or prevention of Pulmonary hypertension secondary to COPD and/or Pulmonary hypertension as PAH and/or Pulmonary hypertension secondary to IPF and/or Pulmonary hypertension secondary to sarcoidosis.

For safe and effective use the disclosed cannula may be used with the disclosed delivery device, and the like, and/or nitric oxide. One skilled in the art will appreciate that using a cannula other than the disclosed cannula along with the disclosed delivery device, and the like, and/or nitric oxide may increase safety risks and/or reduce and/or eliminate effective use. Accordingly, the cannula of present invention may be necessary for delivering nitric oxide for PAH, IPF, and/or COPD.

Any of the nasal cannulas described herein can be used in nitric oxide therapy to treat appropriate diseases. For example, the cannulas can be for pulsed NO therapy to treat chronic obstructive pulmonary disease (COPD) or pulmonary arterial hypertension (PAH). For these diseases, the delivery of the appropriate dose amounts and appropriate dose timing may be very important. For COPD, the NO may need to be pulsed early in inspiration, such as the first half of inspiration. If NO is, for example, not delivered in the right amount or at the right time, reversal of hypoxic vasoconstriction can occur, which could worsen the patient's condition. Furthermore, the dose amount can be very important for PAH because sudden discontinuation of therapy can lead to serious events such as rebound hypertension. Thus, significant dilution of the NO dose should be minimized for these diseases. Any of the cannula materials, configurations or methods described herein can be used to minimize dilution of the NO dose during NO therapy.

In exemplary embodiments, lumens (e.g., tubes) of the cannula can carry backwards towards the patient and/or can be affixed to each other so as to produce a substantially singular element umbilical between the cannula nosepiece and the device, which can provide a cross-section. It will be understood that when describing a plurality of lumens (e.g., two lumens, three lumens, four lumens, etc.) all of the lumens can be included in a single cannula.

In exemplary embodiments, elements of the cannula can be manufactured using any of the techniques disclosed herein and/or using techniques known in the art. For example, cannula lumens (e.g., tubes), nosepiece, key member, connectors, reducers, any combination and/or further separation thereof, and/or any element of cannulas described herein can be manufacturing using extrusion techniques, molding techniques, and/or using any other manufacturing technique.

It will be understood that the each lumen the nasal cannula and/or collective nasal cannula lumen cross-section can be any shape such as, but not limited to, to circular, parabolic, ellipsoidal, square, rectangular, triangular, and/or any other cross-section and/or or any other regular or irregular shape to minimize dose dilution. For ease, at times the geometry and/or cross-section is described as circular, parabolic, and/or ellipsoidal and/or the cross-section is described as a diameter, inner diameter, or the like. This is merely for ease and is in no way meant to be a limitation. When one or more cross-sectional areas are not circular, then the ratio of inner diameters can be the square root of the ratio of the surface areas of the two lumina sections.

It will be understood that any of the above can be used for pulsed and/or non-pulsed delivery of a therapeutic gas (e.g., NO). For example, any of the above embodiments referencing pulsed delivery of a therapeutic gas, when applicable, can be used with non-pulsed delivery of a therapeutic gas, and vice versus. For ease, at times, reference may be made to pulsed or non-pulsed. This is merely for ease and is in no way meant to be a limitation.

Reference throughout this specification to "one embodiment," "certain embodiments," "one or more embodiments," "exemplary embodiment," "exemplary embodiments," and/ or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment," "exemplary embodiment," "exemplary embodiments," and/or "in an embodiment" in various places throughout this specification are not necessarily referring to the same embodiment of the invention. Furthermore, the particular features, structures, materials, or characteristics can be combined in any suitable manner in one or more embodiments.

It will be understood that any of the steps described can be rearranged, separated, and/or combined without deviated from the scope of the invention. For ease, steps are, at times, presented sequentially. This is merely for ease and is in no way meant to be a limitation.

Further, it will be understood that any of the elements and/or embodiments of the invention described can be rearranged, separated, and/or combined without deviated from the scope of the invention. For ease, various elements are described, at times, separately. This is merely for ease and is in no way meant to be a limitation.

Although the disclosure herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A nasal cannula for therapeutic gas delivered to a patient in need thereof, comprising:
    a first lumen, a second lumen, and a third lumen;
        wherein the first lumen is a first therapeutic gas lumen for delivering a first therapeutic gas to a patient in need thereof,
        wherein the second lumen is a triggering lumen, and
        wherein the third lumen is a second therapeutic gas lumen for delivering a second therapeutic gas to the patient; and
    a cannula nosepiece allowing separate flow paths to the patient for at least one of (i) the first therapeutic gas lumen, (ii) the triggering lumen, and (iii) the second therapeutic gas lumen,
    wherein the first therapeutic gas lumen comprises a material selected from the group consisting of polyvinylidene chloride (PVDC) and ethylene vinyl alcohol (EVOH),
    wherein the first therapeutic gas lumen comprises a co-extrusion of polyvinyl chloride (PVC) and EVOH or a co-extrusion of PVC and PVDC.

2. The nasal cannula of claim 1, wherein the nasal cannula (i) reduces dilution of one or more of the first and second therapeutic gases delivered to the patient or (ii) is configured to be placed in fluid communication with at least one system to deliver one or more of the first and second therapeutic gases to the patient, or both.

3. The nasal cannula of claim 1, wherein the nasal cannula at least one of inhibits mixing of nitric oxide and oxygen and reduces delivery of nitrogen dioxide to the patient.

4. The nasal cannula of claim 1, wherein the first therapeutic gas is nitric oxide and the second therapeutic gas is oxygen, and wherein the first therapeutic gas lumen for delivering nitric oxide is smaller than the second therapeutic gas lumen for delivering oxygen and the triggering lumen.

5. The nasal cannula of claim 1, wherein the first therapeutic gas is nitric oxide and the first therapeutic gas lumen for delivering nitric oxide is about six feet to about eight feet in length having an inner diameter of about 0.01 inches to about 0.10 inches.

6. The nasal cannula of claim 1, wherein the first therapeutic gas is nitric oxide and the cannula nosepiece comprises a nitric oxide flow path having an inner diameter that is smaller than an inner diameter of the first therapeutic gas lumen.

7. The nasal cannula of claim 1, wherein the first therapeutic gas is nitric oxide and the cannula nosepiece comprises a nitric oxide flow path having a volume that is less than about 10% of a minimum pulse volume of a pulse of nitric oxide.

8. The nasal cannula of claim 1, wherein the cannula comprises a wall material having a low oxygen transmission rate that is between $$0.001 \frac{(cm^3)(mil)}{(24 \text{ hrs})(100 \text{ in}^2)(ATM)} \text{ and } 10 \frac{(cm^3)(mil)}{(24 \text{ hrs})(100 \text{ in}^2)(ATM)}.$$

9. The nasal cannula of claim 1, wherein the cannula is further comprising a fourth lumen:
the fourth lumen being another first therapeutic gas lumen for delivering the first therapeutic gas to the patient; and
wherein the first lumen delivers the first therapeutic gas to one nostril of the patient and the fourth lumen delivers the first therapeutic gas to another nostril of the patient.

10. The nasal cannula of claim 1, further comprising one or more of: (i) at least one check valve in fluid communication with the first therapeutic gas lumen, (ii) a cannula key, (iii) a scavenging material, and (iv) a flexible support bridge.

11. A nasal cannula for therapeutic gas delivered to a patient in need thereof, comprising:
a first lumen, a second lumen, and a third lumen;
wherein the first lumen is a first therapeutic gas lumen for delivering a first therapeutic gas to a patient,
wherein the second lumen is a triggering lumen for triggering release of a pulse of the first therapeutic gas, and
wherein the third lumen is a second therapeutic gas lumen for delivering a second therapeutic gas to the patient;
the first therapeutic gas lumen, the triggering lumen, and the second therapeutic gas lumen aggregating at a cannula nosepiece, the cannula nosepiece allowing separate flow paths to the patient for each of the first therapeutic gas lumen, the triggering lumen, and the second therapeutic gas lumen; and
the first therapeutic gas lumen having an inner diameter that is one or more of (i) smaller than an inner diameter of the second therapeutic gas lumen and an inner diameter of the triggering lumen and (ii) larger than an inner diameter of the flow path for the first therapeutic gas lumen at the cannula nosepiece,
wherein the first therapeutic gas lumen comprises a material selected from the group consisting of polyvinylidene chloride (PVDC) and ethylene vinyl alcohol (EVOH),
wherein the first therapeutic gas lumen comprises a co-extrusion of polyvinyl chloride (PVC) and EVOH or a co-extrusion of PVC and PVDC.

12. The nasal cannula of claim 11, wherein the nasal cannula (i) reduces dilution of one or more of the first and second therapeutic gases delivered to the patient or (ii) is configured to be placed in fluid communication with at least one system to deliver one or more of the first and second therapeutic gases to the patient, or both.

13. The nasal cannula of claim 11, wherein the nasal cannula at least one of inhibits mixing of nitric oxide and oxygen and reduces delivery of nitrogen dioxide to the patient.

14. The nasal cannula of claim 11, wherein the first therapeutic gas is nitric oxide and the first therapeutic gas lumen for delivering nitric oxide is about six feet to about eight feet in length having an inner diameter of about 0.01 inches to about 0.10 inches.

15. The nasal cannula of claim 11, wherein the first therapeutic gas is nitric oxide and the cannula nosepiece comprises a nitric oxide flow path having a volume that is less than about 10% of a minimum pulse volume of a pulse of nitric oxide.

16. The nasal cannula of claim 11, wherein the cannula comprises a wall material having a low oxygen transmission rate that is between $$0.001 \frac{(cm^3)(mil)}{(24 \text{ hrs})(100 \text{ in}^2)(ATM)} \text{ and } 10 \frac{(cm^3)(mil)}{(24 \text{ hrs})(100 \text{ in}^2)(ATM)}.$$

17. The nasal cannula of claim 1, wherein the co-extrusion further comprises a tie layer.

18. The nasal cannula of claim 11, wherein the co-extrusion further comprises a tie layer.

* * * * *